(12) United States Patent  
Alami et al.

(10) Patent No.: US 12,172,965 B2  
(45) Date of Patent: Dec. 24, 2024

(54) DRUG CONJUGATE COMPRISING QUINOLINE DERIVATIVES

(71) Applicants: UNIVERSITE PARIS-SACLAY, Saint-Aubin (FR); CENTRE NATIONAL DE LA RECHERCHE SCIENTIFIQUE, Paris (FR)

(72) Inventors: Mouad Alami, Bussy Saint Georges (FR); Abdallah Hamze, Massy (FR); Olivier Provot, Sartrouville (FR); Ilhem Khelifi, Le Raincy (FR); Vincent Blanchard, Pontfaverger Moronvilliers (FR); Nada Makky-Ibrahim, Massy (FR)

(73) Assignees: UNIVERSITE PARIS-SACLAY, Gif-sur-Yvette (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 820 days.

(21) Appl. No.: 17/276,706

(22) PCT Filed: Sep. 17, 2019

(86) PCT No.: PCT/EP2019/074909  
§ 371 (c)(1),  
(2) Date: Mar. 16, 2021

(87) PCT Pub. No.: WO2020/058290  
PCT Pub. Date: Mar. 26, 2020

(65) Prior Publication Data  
US 2022/0023435 A1 Jan. 27, 2022

(30) Foreign Application Priority Data  
Sep. 17, 2018 (FR) ...................... 18 58366

(51) Int. Cl.  
*A61K 47/68* (2017.01)  
*A61K 47/54* (2017.01)  
(Continued)

(52) U.S. Cl.  
CPC .......... *C07D 215/42* (2013.01); *A61K 47/545* (2017.08); *A61K 47/6803* (2017.08); *A61P 35/00* (2018.01); *C07D 215/48* (2013.01)

(58) Field of Classification Search  
CPC .............. A61K 47/6803; A61K 47/545; A61K 31/4706; A61K 47/6817; A61K 47/6889;  
(Continued)

(56) References Cited

U.S. PATENT DOCUMENTS 7,381,761 B2 6/2008 Stark  
8,535,678 B2 9/2013 Law et al.  
(Continued)

FOREIGN PATENT DOCUMENTS

CN 101472945 A 7/2009  
CN 105899537 A 8/2016  
(Continued)

OTHER PUBLICATIONS

International Search Report for PCT/EP2019/074909 dated Dec. 2, 2019, 7 pages.  
Written Opinion of the ISA for PCT/EP2019/074909 dated Dec. 2, 2019, 5 pages.  
Zhou et al., "Design, synthesis and biological evaluation of 4-anilinoquinoline derivatives as novel potent tubulin depolymerization agents", European Journal of Medicinal Chemistry, vol. 138, Jul. 22, 2017, pp. 1114-1125 (12 pages).  
Khelifi et al., "Design, synthesis and anticancer properties of IsoCombretaQuinolines as potent tubulin assembly inhibitors", European Journal of Medicinal Chemistry, vol. 127, Nov. 9, 2016, pp. 1025-1034 (10 pages).  
French Search Report for FR 1 858 366 dated May 28, 2019, 2 pages.  
(Continued)

*Primary Examiner* — Karen A. Canella  
*Assistant Examiner* — Sydney Van Druff  
(74) *Attorney, Agent, or Firm* — NIXON & VANDERHYE

(57) ABSTRACT

Disclosed are compounds having the formula (I):

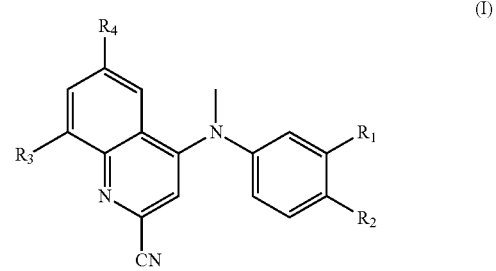

wherein $R_1$ represents a group: —$NH_2$, —$NHCOR_a$, —$NHCOOR_b$, —($C_2$-$C_6$)alkenylene-CO—NH—OH, —($C_2$-$C_6$)alkynylene-CO—NH—OH or —OH; $R_2$ represents a group: —$OCH_3$, —$OCH_2CH_3$, —$SCH_3$, —$SCH_2CH_3$ or —$OCHF_2$; $R_3$ represents a hydrogen atom or a group: —$CH_3$, —CN, —F, —Cl or —$OR_c$; $R_4$ represents a hydrogen atom or a group: —$CH_3$, —CN, —F, —Cl or —$OR_d$; $R_a$ represents a group: —($C_1$-$C_5$)alkyl or —$CF_3$; $R_b$ represents a group: —($C_1$-$C_5$)alkyl or —$CF_3$; $R_c$ represents a group: —($C_1$-$C_5$)alkyl or —$CF_3$; and $R_d$ represents a group: —($C_1$-$C_5$)alkyl or —$CF_3$; in the state of a base or acid or acid salts or base salts or in the form of hydrate or of solvate. Also disclosed are drug conjugates including such compounds.

24 Claims, 3 Drawing Sheets

(51) Int. Cl.
*A61P 35/00* (2006.01)
*C07D 215/42* (2006.01)
*C07D 215/48* (2006.01)

(58) Field of Classification Search
CPC ..... A61P 35/00; C07D 215/48; C07D 215/42; C07D 215/44; C07D 207/452; C07D 401/12
See application file for complete search history.

(56) References Cited

U.S. PATENT DOCUMENTS

| | | |
|---|---|---|
| 2006/0074187 A1 | 4/2006 | Stark et al. |
| 2011/0256157 A1 | 10/2011 | Howard et al. |
| 2012/0225089 A1 | 9/2012 | Bouchard et al. |
| 2014/0227180 A1 | 8/2014 | Govindan et al. |
| 2017/0035761 A1 | 2/2017 | Alami |
| 2019/0023645 A1 | 1/2019 | Alami |

FOREIGN PATENT DOCUMENTS

| | | |
|---|---|---|
| CN | 105899538 A | 8/2016 |
| EP | 1 391 213 | 2/2004 |
| EP | 1 912 677 | 10/2013 |
| EP | 3 129 368 | 2/2017 |
| FR | 3 019 819 | 10/2015 |
| WO | 2011/001052 | 1/2011 |
| WO | 2014/164534 | 10/2014 |
| WO | 2015/155262 | 10/2015 |
| WO | 2017118822 A2 | 7/2017 |
| WO | WO-2017198756 A1 * | 11/2017 |
| WO | 2018/178277 | 10/2018 |

OTHER PUBLICATIONS

Japanese Search Report, issued in Japanese Patent Application No. 2021-514607 dated Jun. 22, 2023.
Khelifi et al., "N, N-bis-heteroaryl methylamines: Potent antimitotic and highly cytotoxic agents", European Journal of Medicinal Chemistry, vol. 168, 2019, pp. 176-188.
Naret et al., "1,1-Diheterocyclic Ethylenes Derived from Quinaldine and Carbazole as New Tubulin-Polymerization Inhibitors: Synthesis, Metabolism, and Biological Evaluation", Journal of Medicinal Chemistry, vol. 62, 2019, pp. 1902-1916.
Jackson, "Processes for Constructing Homogeneous Antibody Drug Conjugates", Organic Process Research & Development, vol. 20, 2016, pp. 852-866.
Sanderson et al., "In vivo Drug-Linker Stability of an Anti-CD30 Dipeptide-Linked Auristatin Immunoconjugate", Clinical Cancer Research, vol. 11, Jan. 11, 2005, pp. 843-852.
Chari et al., "Antibody-Drug Conjugates: An Emerging Concept in Cancer Therapy", Angewandte Chemie International Edition, vol. 53, 2014, pp. 3796-3827.
Moolten et al., "Antitumor Effects of Antibody-Diphtheria Toxin Conjugates: Use of Hapten-Coated Tumor Cells as an Antigenic Target", Journal of the National Cancer Institute, vol. 49, No. 4, Oct. 1972, pp. 1057-1062.
Levy et al., "The Specific Cytotoxic Effects of Daunomycin Conjugated to Antitumor Antibodies", Cancer Research, vol. 35, May 1975, pp. 1182-1186.
Liu et al., "Eradication of large colon tumor xenografts by targeted delivery of maytansinoids", Proc. Natl. Acad. Sci. USA, Medical Sciences, vol. 93, Aug. 1996, pp. 8618-8623.
Lode et al., "Targeted Therapy with a Novel Enediyene Antibiotic Calicheamicin theta(I)1, Effectively Suppresses Growth and Dissemination of Liver Metastases a Syngeneic Model of Murine Neuroblastoma", Cancer Research, vol. 58, Jul. 15, 1998, pp. 29525-2928.
Hinman et al., "Preparation and Characterization of Monoclonal Antibody Conjugates of the Calicheamicins: A Novel and Potent Family of Antitumor Antibiotics", Cancer Research, vol. 53, Jul. 15, 1993, pp. 3336-3342.

Govindan et al., "Milatuzumab-SN-38 Conjugates for the Treatment of CD74 Cancers", Molecular Cancer Therapeutics, vol. 12(6), Jun. 2013, pp. 968-978.
Stein et al., "CD74: A New Candidate Target for the Immunotherapy of B-Cell Neoplasms", Clinical Cancer Research 2007, vol. 13 (18 Suppl.), Sep. 15, 2007, pp. 5556s-5563s.
Kung Sutherland et al., "SGN-CD33A: a novel CD33-targeting antibody-drug conjugate using a pyrrolobenzodiazepine dimer is active in models of drug-resistant AML", Blood, vol. 122, No. 8, Aug. 22, 2013, pp. 1455-1463.
Miller et al., "Abstract B126: Potent antigen-specific anti-tumor activity observed withantibody-drug conjugates (ADCs) made using a new class of DNA-crosslinking agents", Mol. Cancer Ther. 2009, vol. 8 (12 Suppl.), B126, Monoclonal Antibodies, Total No. pp. 1.
Verma et al., "The cryptophycins as potent payloads for antibody drug conjugates", Bioorganic & Medicinal Chemistry Letters, vol. 25, 2015, pp. 864-868.
Laguzza et al., "New Antitumor Monoclonal Antibody-Vinca Conjugates LY203725 and Related Compounds: Design, Preparation, and Representative in Vivo Activity", Journal of Medicinal Chemistry, vol. 32, No. 3, 1989, pp. 548-555.
Uadia et al., "Tumor and Tissue Distribution of a Methotrexate-Anti-EL4 Immunoglobulin Conjugate in EL4 Lymphoma-bearing Mice", Cancer Research, vol. 44, Oct. 1984, pp. 4263-4266.
Casi et al., "Antibody-drug conjugates: Basic concepts, examples and future perspectives", Journal of Controlled Release, vol. 161, 2012, pp. 422-428.
Wu et al., "Arming antibodies: prospects and challenges for immunoconjugates" Nature Biotechnology, vol. 23, No. 9, Sep. 2005, pp. 1137-1146.
Pettit et al., "Isolation, Structure, and Synthesis of Combretastatins A-1 and B-1, Potent New Inhibitors of Microtubule Assembly, Derived from Combretum caffrum", Journal of Natural Products, vol. 50, No. 1, Jan.-Feb. 1987, pp. 119-131.
Dark et al., "Combretastatin A-4, an Agent That Displays Potent and Selective Toxicity toward Tumor Vasculature", Cancer Research, vol. 57, May 15, 1997, pp. 1829-1834.
Grosios et al., "In vivo and in vitro evaluation of combretastatin A-4 and its sodium phosphate prodrug" British Journal of Cancer, vol. 81(8), 1999, pp. 1318-1327.
Soussi et al., "IsoCombretaQuinazolines: Potent Cytotoxic Agents with Antitubulin Activity", Chem. Med. Chem., vol. 10(8), 2015, Total No. pp. 5.
Toki et al., "Protease-Mediated Fragmentation of p-Amidobenzyl Ethers: A New Strategy for the Activation of Anticancer Prodrugs", Journal of Organic Chemistry, vol. 67, No. 6, 2002, pp. 1866-1872.
Bolu et al., "Combretastatin A-4 Conjugated Anti-Angiogenic Micellar Drug Delivery Systems Using Dendron-Polymer Conjugates", Molecular Pharmaceutics, vol. 13, 2016, Total No. pp. 34.
Nani et al., "Near-IR Light-Mediated Cleavage of Antibody-Drug Conjugates Using Cyanine Photocages", Angewandte Chemie International Edition, vol. 54, 2015, pp. 13635-13638.
Shen et al., "Disulfide Spacer between Methotrexate and Poly (D-lysine): A Pobe for Exploring the Reductive Process in Endocytosis", The Journal of Biologoical Chemistry, vol. 260, No. 20, Sep. 15, 1985, pp. 10905-10908.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., vol. 13, No. 4, 2002, pp. 855-869.
Lu et al., "Linkers Having a Crucial Role in Antibody-Drug Conjugates", International Journal of Molecular Sciences, vol. 17, 561, 2016, pp. 1-22.
McCombs et al., "Antibody Drug Conjugates: Design and Selection of Linker, Payload and Conjugation Chemistry", The American Association of Pharmaceutical Scientists Journal, vol. 17, No. 2, Mar. 2015, Total No. pp. 13.
Ducry et al., "Antibody-Drug Conjugates: Linking Cytotoxic Payloads to Monoclonal Antibodies", Bioconjugate Chem., vol. 21, 2010, pp. 5-13.
Jain et al., "Current ADC Linker Chemistry", Pharm. Res., vol. 32, 2015, pp. 3526-3540.

(56) References Cited

OTHER PUBLICATIONS

Dimitrov, "Therapeutic Antibodies: Methods and Protocols", Methods in Molecular Biology, Springer Science, vol. 525, 2009, Total No. pp. 591.
Badescu et al., "A New Reagent for Stable Thiol-Specific Conjugation", Bioconjugate Chem., vol. 25, 2014, pp. 460-469.
Still et al., "Chemical behavior of an α-azidosulfide, and the related sulfoxide and sulfone, in the tetrahydrothiophene series", Canadian Journal of Chemistry, vol. 62, 1984, pp. 586-590.
Kazane et al., "Site-specific DNA-antibody conjugates for specific and sensitive immuno-PCR", PNAS, vol. 19, No. 10, Mar. 6, 2012, pp. 3731-3736.
Ban et al., "Tyrosine Bioconjugation through Aqueous Ene-Type Reactions: A Click-Like Reaction for Tyrosine", Journal of the American Chemical Society, vol. 132, No. 5, 2010, pp. 1523-1525.
Zhou et al., "Bioconjugation by Native Chemical Tagging of C—H Bonds", Journal of the American Chemical Society, vol. 135, 2013, pp. 12994-12997.
Zeglis et al., "Enzyme-Mediated Methodology for the Site-Specific Radiolabeling of Antibodies Based on Catalyst-Free Click Chemistry", Bioconjugate Chemistry, vol. 24, 2013, pp. 1057-1067.
Tolcher, "BR96-doxorubicin: been there, done that!", J. Clin. Oncol., Comment, Dec. 1, 2000, vol. 18, 1 page.
Saleh et al., "Phase I Trial of the Anti-Lewis Y Drug Immunoconjugate BR96-Doxorubicin in Patients With Lewis Y-Expressing Epithelial Tumors", Journal of Clinical Oncology, vol. 18, No. 11, Jun. 2000, pp. 2282-2292.
Tolcher et al., "Randomized Phase II Study of BR96-Doxorubicin Conjugate in Patients With Metastatic Breast Cancer", Journal of Clinical Oncology, vol. 17, No. 2, Feb. 1999, pp. 478-484.

\* cited by examiner

|  |  | IC$_{50}$ (HCT116) nM |
|---|---|---|
| 4f |  | 2 |
| 4j |  | 12 |
| 4g |  | 5.7 |
| 4k |  | 3.4 |

| | |
|---|---|
| Mal-Val-Cit-PABC-ICQN-1 (cleavable) (VB179) | |
| Mal-Val-Cit-PABC-ICQO-1 (VB185) | |
| Mal-PEG4-Val-Cit-PABC-ICQN-1 (VB199) | |
| Mal-PEG4-Val-Cit-PABC-ICQO-1 (VB279 & VB288) | |

FIGURE 2A

| | |
|---|---|
| Mal-Val-Cit-PABC-NI313 (VB277) |  |
| Mal-ICQN-1 (non cleavable) (VB284) |  |
| MCC-ICQN-1 (non cleavable) (VB289) |  |

DRUG CONJUGATE COMPRISING QUINOLINE DERIVATIVES

CROSS-REFERENCE TO RELATED APPLICATIONS

This application is the U.S. national phase of International Application No. PCT/EP2019/074909 filed Sep. 17, 2019 which designated the U.S. and claims priority to FR 18 58366 filed Sep. 17, 2018, the entire contents of each of which are hereby incorporated by reference.

BACKGROUND OF THE INVENTION

Field of the Invention

The present invention relates to novel natural product-derived combretastatin-based compounds that are useful as payloads (also referred to as toxins), in particular in drug-conjugates. The present invention in addition relates to new compositions of combretaquinolines, including those which may be used as payloads, payload-linkers, and drug-conjugates, and in methods that use these payloads, payload-linkers, and drug-conjugates, in order to treat pathologies such as, for example, cancer, an inflammatory or infectious disease.

Description of the Related Art

For many types of cancers, conventional chemotherapy still remains the only effective form of treatment. Chemotherapy essentially works on the basis of a cytotoxic effect: a toxin kills cancer cells, thus halting tumour growth. Chemotherapeutic agents primarily damage and destroy cells with a high level of cell-division activity. However, these treatments need to be improved in order to better target and destroy the malignant cells while minimising unintended collateral toxicity to normal tissues. In fact, even at the present time, since these medicinal products also damage healthy cells, patients suffer from serious adverse events or effects. A number of highly cytotoxic medicinal products are of limited clinical utility because they are equally aggressive against normal cells as they are against malignant tumour cells. Healthy tissues may be significantly affected by cytotoxic agents. Since these medicinal products do not explicitly distinguish between normal cells and tumour cells, thereby leading to adverse effects, the medicinal products are often dosed at minimal levels, which tends to diminish the efficacy thereof. This is the reason why it is important to find a way to specifically target cell tumours.

Improving the delivery of drugs and other agents to the target cells, tissues and tumours in order to achieve maximal efficacy and minimal toxicity has been the focus of considerable research over very many years. Modern anti-cancer therapies now target the cancer more precisely using large molecules such as antibodies. Antibodies are an important, naturally occurring part of the immune system, being large molecules that are specifically able to bind to the cell surface of an "intruder" (for example, a virus) and in this way eliminate it. However antibodies, often not curative, need to be combined with chemotherapeutic agents.

Although numerous attempts have been made to develop effective methods for importing biologically active molecules into cells, both in vivo and in vitro, none has proved to be entirely satisfactory. It is often difficult, inefficient or ineffective to optimise the association of the drug with its intracellular target while also minimising the intercellular redistribution of the drug, for example to neighbouring cells.

The concepts of antibody conjugates and drugs ("Antibody Drug Conjugates" also referred to as ADC) seek to overcome these limitations. They are composed of 3 key elements: an antibody (designed to selectively target the tumour of interest), a toxic payload (a cytotoxic compound that will kill the tumour, referred to as "payload" in the art) and the linker (used for conjugating the toxic payload to the antibody). The main advantage of such constructs lies in the significant enhancement of the therapeutic window: increase in the half-life and the specificity of the toxic payload, reducing the off-target toxicity and effects. The use of ADCs has been the subject of extensive in-depth studies over the past three decades (Moolten et al. (1972), J Natl Cancer Inst. 49 (4): 1057-62, Chari et al, (2014) Angewandte Chemie Int. Ed. 53: 3796-3827; Jackson, (2016) Org. Process Res. Dev. 2016, 20: 852-866). A number of ADCs have already been approved and marketed (Kadcyla from Roche and Adcetris from Seattle Genetics).

Payloads (or toxins) used in ADCs include bacterial toxins such as diphtheria toxin (Levy et al. (1975) Cancer Res. 35(5):1 182-6), plant toxins such as ricin, small molecule toxins such as maytansinoids (EP 1391213; Liu et al., (1996) Proc. Natl. Acad. Sci. USA 93:8618-8623), calicheamicin (Lode et al. (1998) Cancer Res. 58:2925-2928; Upeslacis et al., (1993) Cancer Res. 53, 3336-3342), auristatins (Sanderson et al. (2005) Clin. Cancer Res. 11:843-52), SN-38 or irinotecan analogues (Govidan et al. (2013) Mol. Cancer. Ther. 12:968-78, US 2014/0227180A1, Goldenberg et al. (2007), Clin. Cancer Res. 13, 5556s-5563s), pyrrolobenzodiazepins (US 2011/0256157A1, Kung Sutherland et al. Blood (2013) 122:1455-1463, Chari et al., (2009) Mol. Cancer Ther. 8, B126.) or cryptophycines (WO 2011/001052A1, Verma et al. (2015) Bioorg. Med. Chem. Lett. 25:864-8, US 2012/0225089). At present, more than 60% of all ADCs currently in the process of clinical evaluation carry toxins related to Monomethyl Auristatin E and F (tubulin inhibitors MMAE, MMAF). MMAE could be considered by the person skilled in the art as the reference standard payload against which to make a comparison.

The conjugation of drugs to antibodies, either directly or via linking agents ("linkers"), either directly or via linkers, involves taking into account a variety of factors, including the identity and location of the chemical group for conjugation of the drug, the mechanism of drug release, and the structural elements that provide for drug release, and the structural modification to the released free drug. In addition, if the drug is to be released after antibody internalisation, the mechanism of release of the drug must be consonant with the intracellular trafficking of the conjugate. Therefore, while a certain number of different drug classes have been tried as payloads, only a few drug classes have proved efficacious as antibody drug conjugates, because of limited effectiveness, selectivity and/or stability thereof (Tolcher et al. (2000) J Clin. Oncol. 18:4000, Laguzza et al (1989) J. Med. Chem. 32:548-555, Uadia P, (1984). Cancer Res. 44:4263-4266). It turns out that compounds, in order to effectively be eligible as conjugates, should present a level of cytotoxicity that is below the nanomolar IC50 level (Casi and Neri, (2012) J. Control Release. 20; 161 (2):422-8; Wu and Senter (2005) Nat. Biotechnol. 23(9):1 137-46). Ideal payloads should escape from the multi-drug resistance mechanism (MDR). In the case of MMAE, which is subject to MDR, some tumours are able to develop a mechanism of resistance (Chen et al., 2015). The few payloads accessible are not effective against the large spectrum of cancer indications.

Because of these limitations, there is a clinical demand for new payloads that have differentiated modes of action, improved selectivity and toxicity profile and are not subject to MDR. For these reasons, combretastatins have been considered as potential toxic payload.

In fact, Combretastatin was isolated from the native African tree *Combretum caffrum* and the like in the 1980s, and was verified to have tubulin polymerisation inhibitory activity (Pettit GR (1987), J Nat Prod 50:1 19-131). Combretastatin A-4 (or CA-4) and analogues are cytotoxic and selectively disrupt tumoral vasculature or prevent its neoformation (Dark et al. (1997) Cancer Res 57, 1829-1834, Grosios K, et al (1999) Br J Cancer 81: 1318-1327). This this structurally very simple stilbene CA-4 includes several drawbacks such as a low water-solubility and a chemical instability of the Z-configured double bond, which isomerises during storage, administration and metabolism. Another drawback of CA-4 is its insufficient cytotoxicity. These problems have been overcome by the development of new derivatives using nitrogen-containing heterocycles such as quinazolines and quinolones (Soussi MA et al (2015) Chem. Med Chem. 10(8): 1392-402; I. Khelifi, et al, (2017), European Journal of Medicinal Chemistry 127:1025-1034). With these derivatives, the 3,4,5-trimethoxyphenyl group, considered to be responsible for the effects of neurotoxicity or cardiotoxicity, has been eliminated. However, none of these compounds could be used as a payload.

Combretastatins have been cited to be potentially used as payloads in some patents, but without exemplification or supporting data: (EP 1 912 677 B1 "PSMA antibody-drug conjugates"); WO 2014/164534 ("Site-specific antibody-drug conjugation through glycoengineering"); U.S. Pat. No. 8,535,678 B2 ("Anti-CD70 antibody-drug conjugates and their use for the treatment of cancer and immune disorders"). On the other hand, combretastatins have been evaluated as potential payloads in the context of a few studies, but without any clinical applications thus far due to their limited potency, stability issues and unfavourable metabolisation profiles acknowledged by the authors themselves (Toki et al (2002) J. Org. Chem. 67, 1866-1872, Bolu et al (2016) Mol. Pharmaceutics, 13, 1482-1490, R. Nani et al (2015) Angew. Chem. Int. Ed. Engl. 9; 54(46): 13635-13638). The only example of the use of combretastatin derivatives as payloads comes from the patent application describing the new isoNH2CombretaQuinolines (iso-amino-combretaquinolines) (PCT/EP2018/058168). However, the resulting ADC Trastuzumab-VC-PAB-ICQO-I gave an IC50 value of 27 µg/mL against the cell line SKBR3. Such a level of cytotoxicity is 3 logs lower than the ng/mL which is expected from an ADC and is not sufficient for the purposes of therapeutic use. In other words, although these derivatives have shown promising properties as autonomous derivatives, they seem to lose their cytotoxicity when conjugated. In addition, the process of conjugation of these derivatives has proved difficult and could be the subject of innovative improvements.

In conclusion, most conjugation attempts have failed so far, even with the new iso-combretaquinoline derivatives.

SUMMARY OF THE INVENTION

The invention therefore seeks to solve one or more of the technical problems mentioned above.

In particular, the object of the present invention is to provide a compound that is useful as a payload (toxic payload or toxin) which exhibits toxicity, stability and a metabolisation profile, that is eligible as a payload, in particular usable in a drug-conjugate.

The object of the invention is to provide a new payload that has a differentiated mode of action, an improved selectivity and toxicity profile, and is not subject to the phenomenon of multi-drug resistance.

After prolonged research and in a surprising manner, the present inventors discovered novel compounds having a structure that enables their use in an antibody-drug conjugate.

Thus, according to a first aspect, the present invention relates to compounds having the formula (I):

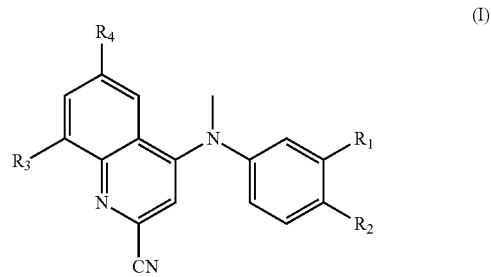

wherein:
$R_1$ represents a group: —$NH_2$, —$NHCOR_a$, —NHCO—$OR_b$, —($C_2$-$C_6$)alkenylene-CO—NH—OH, —($C_2$-$C_6$)alkynylene-CO—NH—OH or —OH;
$R_2$ represents a group: —$OCH_3$, —$OCH_2CH_3$, —$SCH_3$, —$SCH_2CH_3$ or —$OCHF_2$;
$R_3$ represents a hydrogen atom or a group: —$CH_3$, —CN, —F, —Cl or —$OR_c$;
$R_4$ represents a hydrogen atom or a group: —$CH_3$, —CN, —F, —Cl or —OR a;
$R_a$ represents a group: —($C_1$-$C_5$)alkyl or —$CF_3$;
$R_b$ represents a group: —($C_1$-$C_5$)alkyl or —$CF_3$;
$R_c$ represents a group: —($C_1$-$C_5$)alkyl or —$CF_3$; and
$R_d$ represents a group: —($C_1$-$C_5$)alkyl or —$CF_3$;
in the following state: base or acid, or salts of acids or salts of bases; or in the form of a hydrate or a solvate.

The inventors have discovered that these compounds present improved efficacy against cancer, in particular against resistant tumour cells. In addition, they have a high level of chemical stability and are not subject to any isomerisation therefore having no tendency to inactivation.

According to a second aspect, the present invention relates to compounds having the formula (II):

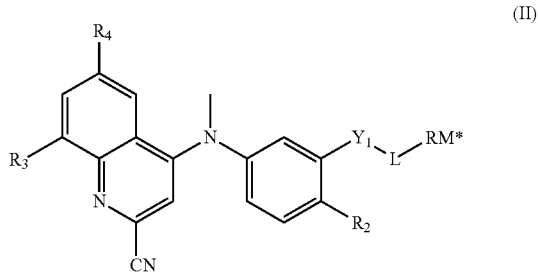

wherein:
$Y_1$ represents —O—, —NH—, —NHCO—, —$NHCOR_a$—, —NHCOO—, —$NHCOOR_b$—, —(C$_2$-C$_6$)alkenylene-CO—NH—O— or —(C$_2$-C$_6$) alkenylene-CO—NH—O—;

R$_2$ represents a group: —OCH$_3$, —OCH$_2$CH$_3$, —SCH$_3$, —SCH$_2$CH$_3$ or —OCHF$_2$;

R$_3$ represents a hydrogen atom or a group: —CH$_3$, —CN, —F, —Cl or —OR; and preferably a hydrogen atom;

R$_4$ represents a hydrogen atom or a group: —CH$_3$, —CN, —F, —Cl or —OR; and preferably a hydrogen atom;

R$_a$ represents a group: —(C$_1$-C$_5$)alkylene- or —CF$_2$—;
R$_b$ represents a group: —(C$_1$-C$_5$)alkylene- or —CF$_2$—;
R$_c$ represents a group: —(C$_1$-C$_5$)alkyl or —CF$_3$;
R$_d$ represents a group: —(C$_1$-C$_5$)alkyl or —CF$_3$;

L represents a linking agent (linker);

RM* is selected from RM and RM', wherein RM is a reactive functional group that is able to form a covalent bond with a targeting agent moiety, in particular with an antibody moiety or a functional fragment thereof, and wherein RM' is an RM moiety carrying at least one protecting group;

in the following state: base or salts of bases; or in the form of a hydrate or a solvate.

According to a third aspect, the present invention relates to antibody-drug conjugates having the formula (III):

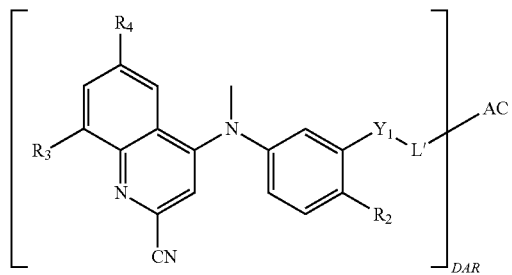

wherein:

Y$_1$ represents —O—, —NH—, —NHCO—, —NHCOR$_a$—, —NHCOO—, —NHCOOR$_b$—, —(C$_2$-C$_6$)alkenylene-CO—NH—O— or —(C$_2$-C$_6$) alkenylene-CO—NH—O—;

R$_2$ represents a group: —OCH$_3$, —OCH$_2$CH$_3$, —SCH$_3$, —SCH$_2$CH$_3$ or —OCHF$_2$;

R$_3$ represents a hydrogen atom or a group: —CH$_3$, —CN, —F, —Cl or —OR; and preferably a hydrogen atom;

R$_4$ represents a hydrogen atom or a group: —CH$_3$, —CN, —F, —Cl or —OR; and preferably a hydrogen atom;

R$_a$ represents a group: —(C$_1$-C$_5$)alkylene- or —CF$_2$—;
R$_b$ represents a group: —(C$_1$-C$_5$)alkylene- or —CF$_2$—;
R$_c$ represents a group: —(C$_1$-C$_5$)alkyl or —CF$_3$;
R$_d$ represents a group: —(C$_1$-C$_5$)alkyl or —CF$_3$;

L represents a linking agent (linker);

AC represents a targeting agent moiety, in particular an antibody moiety or a functional fragment thereof; and wherein the DAR (drug-to-antibody [ie targeting agent] ratio) varies between 1 and 8, and preferably between 2 and 4.

As illustrated in the experimental part, and in an unexpected manner, the inventors have shown that such compounds are very effective, compared to known payloads, and have very good inhibitory activities against numerous cancer cells.

In particular, the compounds having the formula (I) are released from the compounds having the formula (III) in vivo, preferably at the target site.

Other features, aspects and advantages of the invention will become apparent upon reading the detailed description which follows.

Definitions

In the context of the present invention, the following definitions are used:

"C$_t$-C$_z$" denotes a carbon chain which can have from t to z carbon atoms where t and z can take, for example, the values from 1 to 25; for example C$_1$-C$_3$ is a carbon chain which can have from 1 to 3 carbon atoms.

An alkyl denotes a linear or branched, monovalent saturated aliphatic group, which can for example comprise from 1 to 25 carbon atoms, and preferably from 1 to 5 carbon atoms. By way of examples, mention may be made of methyl, ethyl, propyl, isopropyl, butyl, isobutyl, tert-butyl groups, etc.

An alkylene denotes a linear or branched, divalent saturated alkyl group which can for example comprise from 1 to 25 carbon atoms.

An alkenylene denotes an aliphatic hydrocarbon group comprising one carbon-carbon double bond, either linear or branched, with the other bonds being able to be single bonds or other double bonds, and being able for example to comprise from 1 to 25 carbon atoms, and preferably from 2 to 6 carbon atoms. By way of examples, mention may be made of the groups ethenylene (—CH═CH—), I-propenylene, 2-propenylene, I-butenylene, 2-butenylene, 3-butenylene, etc.

An alkynylene denotes an aliphatic hydrocarbon group comprising a carbon-carbon triple bond, either linear or branched, with the other bonds being able to be single bonds, double bonds or other triple bonds, and being able for example to comprise from 1 to 25 carbon atoms, and preferably from 2 to 6 carbon atoms. By way of examples, mention may be made of the groups ethynylene, I-propynylene, 2-propynylene, etc.

A —CF$_2$— group denotes a divalent alkyl group in which the hydrogen atoms have been substituted by two fluorine atoms.

A cycloalkylene denotes a bivalent non-aromatic ring, either monocyclic or polycyclic, which may comprise from 3 to 12 carbon atoms. Byway of examples, mention may be made of cyclopropylene, cyclobutylene, cyclopentylene, cyclohexylene, cycloheptylene, etc.

A cycloalkenylene denotes a bivalent non-aromatic ring, either monocyclic or polycyclic, which may comprise from 3 to 12 carbon atoms, and comprising one or more unsaturations. By way of examples, mention may be made of cyclopentenylene and cyclohexenylene.

A heterocycloalkylene denotes a bivalent non-aromatic ring, either monocyclic or polycyclic, which may comprise from 3 to 12 carbon atoms and at least one heteroatom selected from O, N or S.

A heterocycloalkenylene denotes a bivalent non-aromatic ring, either monocyclic or polycyclic, which may comprise from 3 to 12 carbon atoms and at least one heteroatom selected from O, N or S, and comprising one or more unsaturations.

An arylene denotes a totally or partially aromatic, bivalent ring, which may comprise from 3 to 20 carbon atoms, for example phenylene.

A heteroarylene denotes a totally or partially aromatic, bivalent ring, which may comprise from 3 to 20 carbon atoms, and at least one heteroatom selected from O, N or S.

According to the invention, the term "substituted" is understood to indicate the fact that one or more hydrogen is replaced by one or more groups, for example selected from among the groups: alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, sulfate, sulfonate, sulfamoyl, sulfonamido, nitro, azido, haloalkyl, in particular perfluoroalkyl (such as trifluoromethyl), haloalkoxy, alkylsulfanyl, alkylsulfinyl, alkylsulfonyl, alkylsulfonylamino, arylsulfonoamino, phosphate, phosphonate, phosphinate, alkylcarboxy, alkylcarboxamide oxo, hydroxy, mercapto, amino (optionally mono- or di-substituted, for example by an alkyl, aryl, or heteroaryl), imino, carboxamide, carbamoyl (optionally mono- or di-substituted, for example by an alkyl, aryl, or heteroaryl), amidino, aminosulfonyl, acylamino, aroylamino, (thio)ureido, (arylthio)ureido, alkyl(thio)ureido, cycloalkyl(thio)ureido, aryloxy, aralkoxy, or —O($CH_2$)$_n$—OH, —O($CH_2$)$_n$—$NH_2$, —O($CH_2$)$_n$COOH, —($CH_2$)$_n$COOH, —C(O)O($CH_2$)$_n$R, —($CH_2$)$_n$N(H)C(O)OR, or —N(R)S(O)$_2$R, wherein n is a number between 1 and 4 and R is independently selected by a hydrogen or a group selected from among -alkyl, -alkenyl, -alkynyl, -cycloalkyl, -cycloalkenyl, -heterocycloalkyl, -heterocycloalkenyl, -aryl and -heteroaryl, where appropriate the group or groups themselves being able to be substituted.

The term "a reactive functional group" is understood to refer to a functional group that is capable of forming a covalent bond with another compound.

A moiety denotes a part of a compound.

The term "functional fragment" is understood to refer to a part of a compound comprising a reactive functional group, possibly protected.

The term "protecting group" is understood to refer to a functional group introduced into the molecule from a chemical functional group in order to mask all or part of its reactivity. For example, it may be an imide, amide, carbamate, imine, enamine, sulfonylated derivative, N-sulfenylated-, N-alkylated-, or N-silylated derivative, diol, carbonylated derivative, acetal, ether, benzyl ether, silyl ether, ester, etc.

The term "pharmaceutically acceptable" is understood to refer to that which may be used in the preparation of a pharmaceutical composition, which is generally safe, non-toxic and neither biologically nor otherwise undesirable and which is acceptable for human and/or veterinary pharmaceutical use.

The term "salts of acids or bases (acid or base salts)" is understood to refer to salified acids or bases, for example an acid addition salt may be formed with inorganic acids such as hydrochloric, sulfuric or phosphoric acid, or with organic acids such as acetic acid or benzoic acid. The base salts may be formed with an inorganic base such as aluminum hydroxide, calcium hydroxide, potassium hydroxide, sodium carbonate and sodium hydroxide, or an organic base such as diethanolamine, ethanolamine, N-methylglucamine, triethanolamine or tromethamine.

The term "hydrate or solvate" is understood to refer to forms of associations or combinations with one or more molecules of water or with a solvent.

Compounds Having the Formula (I)

As indicated above, the object of the present invention relates to compounds having the formula (I):

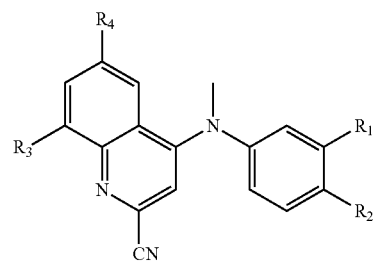

(I)

wherein:
R$_1$ represents a group: —$NH_2$, —NHCOR$_a$, —NHCOOR$_b$, —($C_2$-$C_6$)alkenylene-CO—NH—OH, —($C_2$-$C_6$)alkynylene-CO—NH—OH or —OH;
R$_2$ represents a group: —OCH$_3$, —OCH$_2$CH$_3$, —SCH$_3$, —SCH$_2$CH$_3$ or —OCHF$_2$;
R$_3$ represents a hydrogen atom or a group: —CH$_3$, —CN, —F, —Cl or —OR$_c$;
R$_4$ represents a hydrogen atom or a group: —CH$_3$, —CN, —F, —Cl or —OR$_d$;
R$_a$ represents a group: —($C_1$-$C_5$)alkyl or —CF$_3$;
R$_b$ represents a group: —($C_1$-$C_5$)alkyl or —CF$_3$;
R$_c$ represents a group: —($C_1$-$C_5$)alkyl or —CF$_3$; and
R$_d$ represents a group: —($C_1$-$C_5$)alkyl or —CF$_3$;
in the following state: base or acid, or salts of acids or salts of bases; or in the form of a hydrate or a solvate.

Preferably, R$_3$ represents a hydrogen atom.
Preferably, R$_4$ represents a hydrogen atom.

According to one preferred embodiment, the compound having the formula (I) indeed has the formula (Ia):

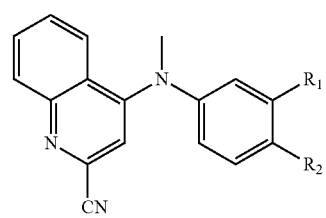

(Ia)

wherein:
R$_1$ represents a group: —$NH_2$, —NHCOR$_a$, —NHCOOR$_b$, —($C_2$-$C_6$)alkenylene-CO—NH—OH, —($C_2$-$C_6$)alkynylene-CO—NH—OH or —OH;
R$_2$ represents a group: —OCH$_3$, —OCH$_2$CH$_3$, —SCH$_3$, —SCH$_2$CH$_3$ or —OCHF$_2$;
R$_a$ represents a group: —($C_1$-$C_5$)alkyl or —CF$_3$; and
R$_b$ represents a group: —($C_1$-$C_5$)alkyl or —CF$_3$;
in the following state: base or acid, or salts of acids or salts of bases; or in the form of a hydrate or a solvate.

Preferably, R$_2$ represents a group: —OCH$_3$, —OCH$_2$CH$_3$, or —OCHF$_2$, and preferably an —OCH$_3$ group.

Preferably, R$_1$ represents a group: —$NH_2$, —NHCOR$_a$, —NHCOOR$_b$, or —OH, in particular R$_1$ represents an —$NH_2$ or —OH group, and preferably an —$NH_2$ group.

According to an even more preferred embodiment, the compound is selected from:

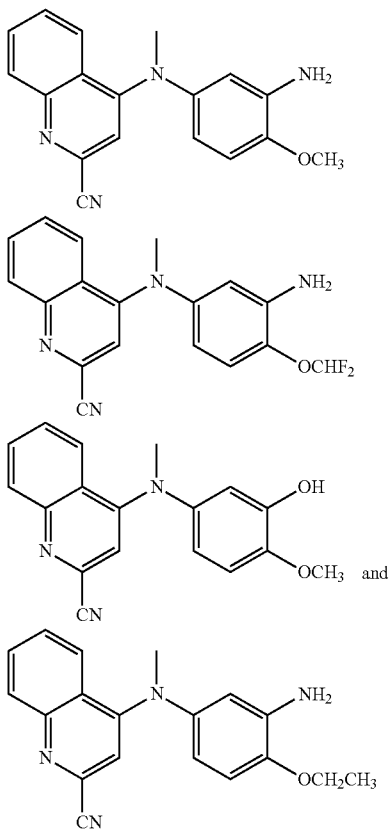

According to one preferred embodiment, the compound having the formula (I) indeed has the formula (Ib):

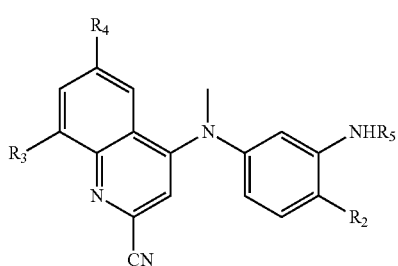

wherein:
- R$_5$ represents a hydrogen atom, a group: —COR$_a$, or —COOR$_b$;
- R$_2$ represents a group: —OCH$_3$, —OCH$_2$CH$_3$, —SCH$_3$, —SCH$_2$CH$_3$ or —OCHF$_2$;
- R$_3$ represents a hydrogen atom or a group: —CH$_3$, —CN, —F, —Cl or —OR$_c$, and preferably a hydrogen atom;
- R$_4$ represents a hydrogen atom or a group: —CH$_3$, —CN, —F, —Cl or —OR$_d$, and preferably a hydrogen atom;
- R$_a$ represents a group: —(C$_1$-C$_5$)alkyl or —CF$_3$;
- R$_b$ represents a group: —(C$_1$-C$_5$)alkyl or —CF$_3$;
- R$_c$ represents a group: —(C$_1$-C$_5$)alkyl or —CF$_3$; and
- R$_d$ represents a group: —(C$_1$-C$_5$)alkyl or —CF$_3$;

in the following state: base or acid, or salts of acids or salts of bases; or in the form of a hydrate or a solvate.

Preferably, R$_1$ represents a group: —(C$_2$-C$_6$)alkenylene-CO—NH—OH or —(C$_2$-C$_6$)alkynylene-CO—NH—OH, and preferably R$_1$ represents a group —CH=CH—CO—NH—OH, —CH=CH—CH$_2$—CH$_2$—CO—NH—OH or —C≡C—CH$_2$—CH$_2$—CO—NH—OH.

According to one preferred embodiment, the compound having the formula (I) indeed has the formula (Ic):

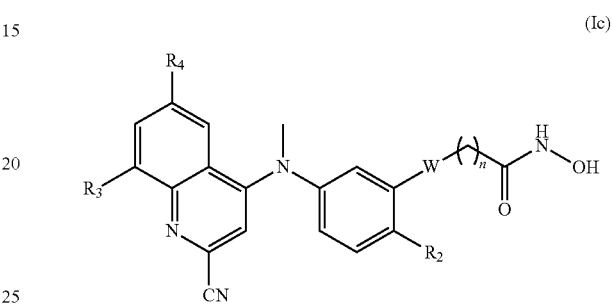

wherein:
- W represents —CH=CH— or —C≡C—;
- n is 0, 1, 2, 3 or 4, and preferably n is 0 or 2;
- R$_2$ represents a group: —OCH$_3$, —OCH$_2$CH$_3$, —SCH$_3$, —SCH$_2$CH$_3$ or —OCHF$_2$;
- R$_3$ represents a hydrogen atom or a group: —CH$_3$, —CN, —F, —Cl or —OR$_c$, and preferably a hydrogen atom;
- R$_4$ represents a hydrogen atom or a group: —CH$_3$, —CN, —F, —Cl or —OR$_d$, and preferably a hydrogen atom;
- R$_c$ represents a group: —(C$_1$-C$_5$)alkyl; and
- R$_d$ represents a group: —(C$_1$-C$_5$)alkyl or —CF$_3$;

in the following state: base or acid, or salts of acids or salts of bases; or in the form of a hydrate or a solvate.

According to one even more preferred embodiment, the compound is selected from:

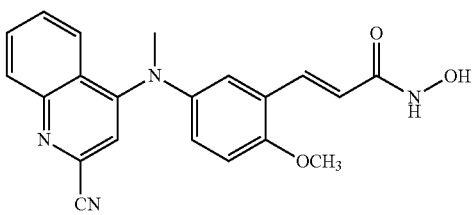

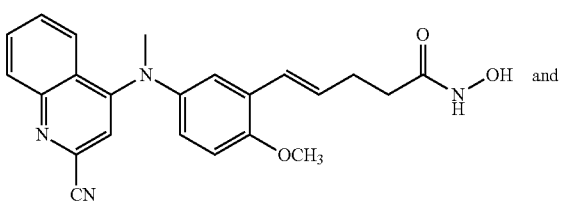

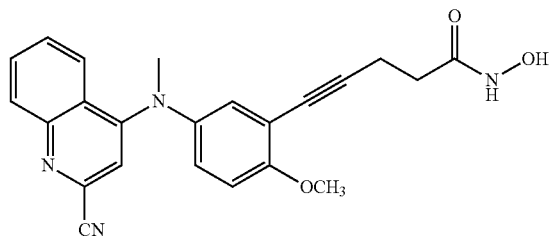

Preparation Method for Preparing Compounds Having the Formula (I)

The present invention relates to a preparation method for preparing a compound having the formula (I) according to the invention, wherein $R_1$ represents an —$NH_2$ or —OH group, characterised in that:

a compound having the formula (A):

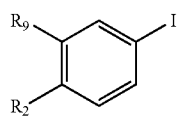

(A)

wherein $R_2$ is as defined in the formula (I) described above and $R_9$ represents a —$NO_2$ or —O-Benzoyl group, is subjected to an amination reaction so as to form a compound having the formula (B):

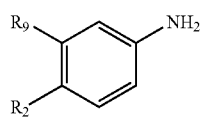

(B)

wherein $R_2$ is as defined in the formula (I) described above and $R_9$ represents a —$NO_2$ or —O-Benzoyl group;

a compound having the formula (C):

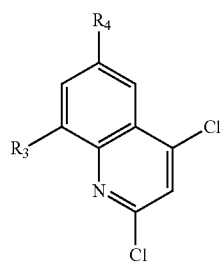

(C)

wherein $R_3$ and $R_4$ are as defined in the formula (I) described above, is subjected to a cyanidation reaction so as to form a compound having the formula (D):

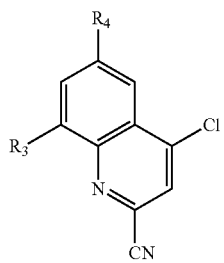

(D)

wherein $R_3$ and $R_4$ are as defined in the formula (I) described above;

the compound having the formula (B) is brought into contact with the compound having the formula (D), so as to form, by an aromatic nucleophilic substitution reaction, the compound having the formula (E):

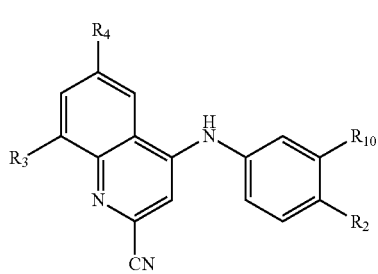

(E)

wherein $R_3$, $R_4$ and $R_2$ are as defined in the formula (I) described above, and $R_{10}$ represents a —$NO_2$ or —O-Benzoyl group;

the compound having the formula (E) is subjected to a methylation reaction, then to a reduction or deprotection reaction so as to form the compound having the formula (I):

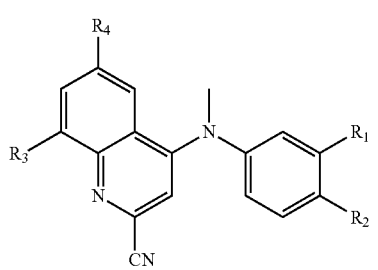

(I)

wherein $R_3$, $R_4$ and $R_2$ are as defined in the formula (I) described above, and $R_1$ represents an —$NH_2$ or —OH group, with $R_a$ and $R_b$ being as defined in the formula (I) described above.

The present invention also relates to a preparation method for preparing a compound having the formula (I) according to the invention, wherein $R_1$ represents an —$NH_2$ group, characterised in that:

a compound having the formula (F):

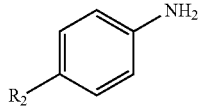
(F)

wherein R$_2$ is as defined in the formula (I) described above, is subjected to a nitration reaction so as to form a compound having the formula (G):

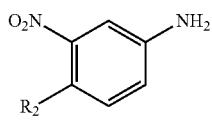
(G)

wherein R$_2$ is as defined in the formula (I) described above;
a compound having the formula (H):

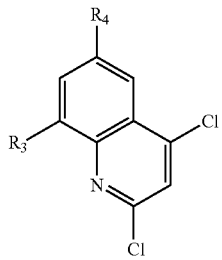
(H)

wherein R$_3$ and R$_4$ are as defined in the formula (I) described above, is subjected to a cyanidation reaction so as to form a compound having the formula (D):

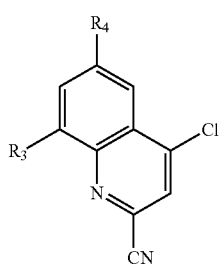
(D)

wherein R$_3$ and R$_4$ are as defined in the formula (I) described above;
the compound having the formula (G) is brought into contact with the compound having the formula (J), so as to form, by a coupling reaction in the presence of palladium, the compound having the formula (K):

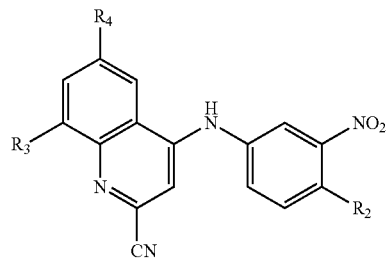
(K)

wherein R$_3$, R$_4$ and R$_2$ are as defined in the formula (I) described above;
the compound having the formula (K) is subjected to a methylation reaction, then to a reduction reaction so as to form the compound having the formula (L):

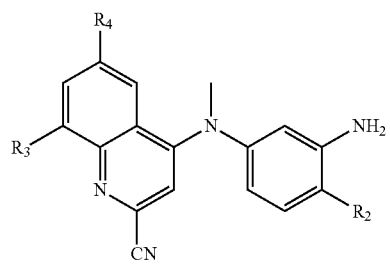
(L)

wherein R$_3$, R$_4$ and R$_2$ are as defined in the formula (I) described above.

The present invention also relates to a preparation method for preparing a compound according to the invention, wherein R$_1$ represents a group: —C2-C6-alkenylene-CO—NH—OH or —C$_2$-C$_6$-alkynylene-CO—NH—OH, characterised in that:

a compound having the formula (M):

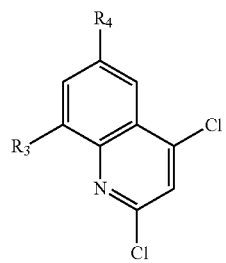
(M)

wherein R$_3$ and R$_4$ are as defined in the formula (I) described above, is subjected to a cyanidation reaction so as to form a compound having the formula (N):

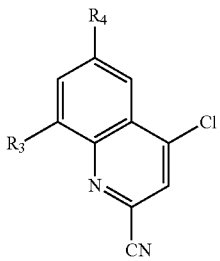

(N)

wherein R$_3$ and R$_4$ are as defined in the formula (I) described above;

the compound having the formula (N) is brought into contact with a compound having the formula (O):

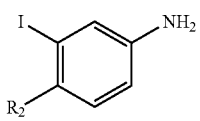

(O)

wherein R$_2$ is as defined in the formula (I) described above, so as to form, by an aromatic nucleophilic substitution reaction, followed by a methylation reaction, the compound having the formula (P):

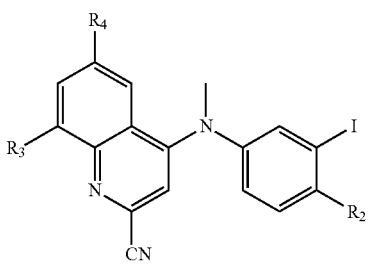

(P)

wherein R$_3$, R$_4$ and R$_2$ are as defined in the formula (I) described above;

the compound having the formula (P) is subjected to an organometallic coupling reaction with a group: —C$_2$-C$_6$-alkenylene-CO—NH—O-(2-tetrahydropyranyl) or —C$_2$-C$_6$-alkynylene-CO— NH—O-(2-tetrahydropyranyl), then to a deprotection reaction, so as to form the compound having the formula (I):

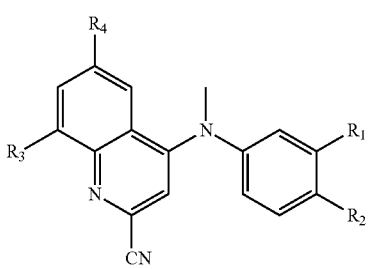

(I)

wherein R$_3$ and R$_4$ and R$_2$ are as defined in the formula (I) described above, and R$_1$ represents a group: —C$_2$-C$_6$-alkenylene-CO—NH—OH or —C$_2$-C$_6$-alkynylene-CO—NH—OH.

According to one preferred embodiment, the present invention relates to a preparation method for preparing a compound according to the invention, wherein R$_1$ represents an NH$_2$ or —OH group, characterised in that:

a compound having the formula (B):

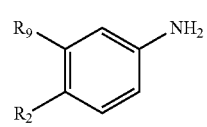

(B)

wherein R$_2$ is as defined in the formula (I) described above and R$_9$ represents a —NO$_2$ or —O-Benzoyl group; is brought into contact with a compound having the formula (D):

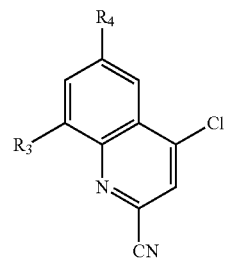

(D)

wherein R$_3$ and R$_4$ are as defined in the formula (I) described above; so as to form, by an aromatic nucleophilic substitution reaction, or by a coupling reaction in the presence of a catalyst, in particular a palladium based catalyst, the compound having the formula (E):

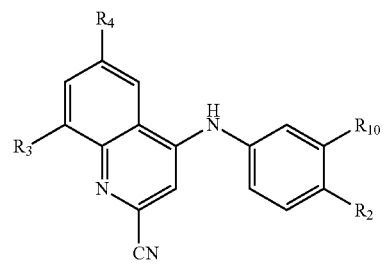

(E)

wherein R$_3$, R$_4$ and R$_2$ are as defined in the formula (I) described above, and R$_{10}$ represents a —NO$_2$ or —O-Benzoyl group;

the compound having the formula (E) is subjected to a methylation reaction, then to a reduction or deprotection reaction, so as to form the compound having the formula (I):

(I)

wherein R₃, R₄ and R₂ are as defined in the formula (I) described above, and R₁ represents an —NH₂ or —OH group, with $R_a$ and $R_b$ being as defined in the formula (I) described above.

According to one preferred embodiment, the present invention relates to a preparation method for preparing a compound (Ic), characterised in that:

the compound having the formula (N):

(N)

wherein R₃ and R₄ are as defined in the formula (Ic) described above; is brought into contact with a compound having the formula (O):

(O)

wherein R₂ is as defined in the formula (Ic) described above, so as to form, by an aromatic nucleophilic substitution reaction, followed by a methylation reaction, the compound having the formula (P):

(P)

wherein R₃, R₄ and R₂ are as defined in the formula (Ic) described above;

the compound having the formula (P) is subjected to an organometallic coupling reaction with a group: —(C₂-C₆)alkenylene-CO—NH—O-(2-tetrahydropyranyl) or —(C₂-C₆)alkynylene-CO—NH—O-(2-tetrahydropyranyl), then to a deprotection reaction, so as to form the compound having the formula (Ic):

(Ic)

wherein, ⌇, n, R₃, R₄ and R₂ are as defined in the formula (Ic) described above.

Preferably, the couplings brought about by aromatic nucleophilic substitution are effected in an acid medium, in particular in the presence of hydrochloric acid.

In particular, they are brought about in a polar aprotic solvent, more particularly in dioxane.

Advantageously, the couplings are brought about at a temperature of between 120° C. and 160° C., in particular between 130° C. and 150° C., in particular at reflux of the solvent.

Advantageously, the steps of couplings are carried out for a period of between 10 hours and 14 hours, in particular between 11 hours and 13 hours, preferably for a period of 12 hours.

In particular, the coupling reactions may be carried out in the presence of a coupling agent, such as diisopropylcarbodiimide (DIC), dicyclohexylcarbodiimide (DCC), 1-(3-dimethylaminopropyl)-3-ethylcarbodiimide (EDC), carbonyldiimidazole (CDI), 2-(1H-benzotriazole-1-yl)-2,1,3,3-tetramethyluronium hexafluorophosphate (HBTU), 2-(1H-benzotriazole-1-yl)-1,1,3,3-tetramethyluronium tetrafluoroborate (TBTU), O-(7-aza=benzotriazol-1-yl)-1,1,3,3-tetramethyluronium hexafluorophosphate (HATU), (benzotriazol-1-yloxy)tripyrrolidinophosphonium hexafluorophosphate (PyBOP) or propylphosphonic anhydride, optionally combined with a coupling agent such as N-hydroxy succinimide (NHS), N-hydroxybenzotriazole (HOBt), 3,4-dihydro-3-hydroxy-4-oxo-1,2,3-benzotriazole (HOBt), 1-hydroxy-7-azabenzotriazole (HOAt), N-hydroxysulfosuccinimide (sulfo NHS), dimethylaminopyridine (DMAP), diisopropylethylamine (DIEA) or N-methylmorpholine (NMM).

The steps of alkylation, preferably of methylation, in particular of an amine, are reactions that are well known to the person skilled in the art who possesses all the knowledge required for execution thereof. For example, they may be brought about by reacting the amine with a —(C₁-C₅)alkyl halide in the presence of a base, in particular a carbonate. The —(C₁-C₅)alkyl halide may preferably be a —(C₁-C₅) alkyl iodide, a —(C₁-C₅)alkyl bromide, or a —(C₁-C₅)alkyl chloride. More particularly, the alkylation steps are carried out in a polar aprotic solvent, more preferably in dimethylformamide. Preferably, the alkylation steps are carried out at room temperature.

The reactions of amination, cyanidation, reduction or deprotection, or even nitration are reactions that are well known to the person skilled in the art who possesses all the knowledge required for execution thereof.

In particular, the amination step can be carried out at a temperature of between 60° C. and 100° C., in particular between 70° C. and 90° C., in particular in the presence of solid iron and hydrochloric acid.

The preparation methods according to the invention may also optionally comprise a step of salification of the compound formed, in order to provide a pharmaceutically acceptable salt, in particular in the presence of a pharmaceutically acceptable acid or base.

The present invention also relates to intermediate compounds, selected from:

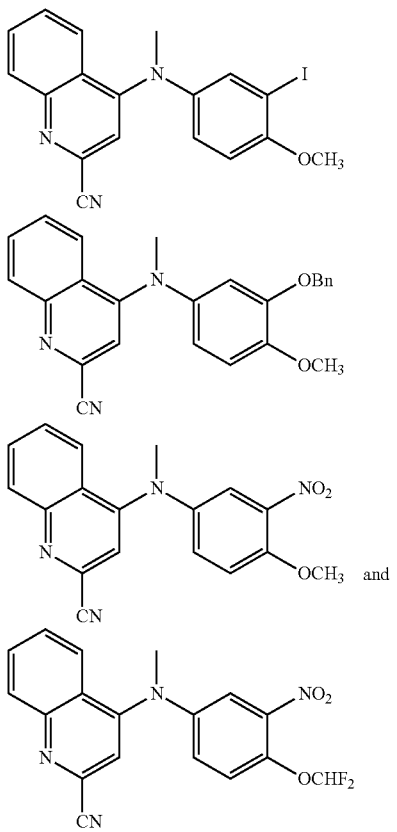

The present invention also relates to the use of such intermediate compounds, for the preparation of compounds having the formula (I) mentioned above.

Compounds Having the Formula (II)

According to another of its aspects, the present invention relates to compounds having the formula (II):

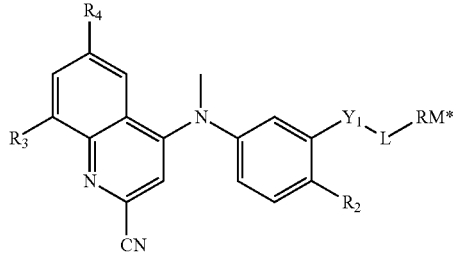

wherein:
- $Y_1$ represents —O—, —NH—, —NHCO—, —NHCOR$_a$—, —NHCOO—, —NHCOOR$_b$—, —(C$_2$-C$_6$)alkenylene-CO—NH—O— or —(C$_2$-C$_6$)alkenylene-CO—NH—O—;
- $R_2$ represents a group: —OCH$_3$, —OCH$_2$CH$_3$, —SCH$_3$, —SCH$_2$CH$_3$ or —OCHF$_2$;
- $R_3$ represents a hydrogen atom or a group: —CH$_3$, —CN, —F, —Cl or —OR$_c$; and preferably a hydrogen atom;
- $R_4$ represents a hydrogen atom or a group: —CH$_3$, —CN, —F, —Cl or —OR$_d$; and preferably a hydrogen atom;
- $R_a$ represents a group: —(C$_1$-C$_5$)alkylene- or —CF$_2$—;
- $R_b$ represents a group: —(C$_1$-C$_5$)alkylene- or —CF$_2$—;
- $R_c$ represents a group: —(C$_1$-C$_5$)alkyl;
- $R_d$ represents a group: —(C$_1$-C$_5$)alkyl or —CF$_3$;
- L represents a linking agent (linker);
- RM* is selected from RM and RM', wherein RM is a reactive functional group that is able to form a covalent bond with a targeting agent moiety, in particular with an antibody moiety or a functional fragment thereof, and wherein RM' is an RM moiety carrying at least one protecting group;

in the following state: base or salts of bases; or in the form of a hydrate or a solvate.

According to a first preferred embodiment, the L-RM* group is selected from among:

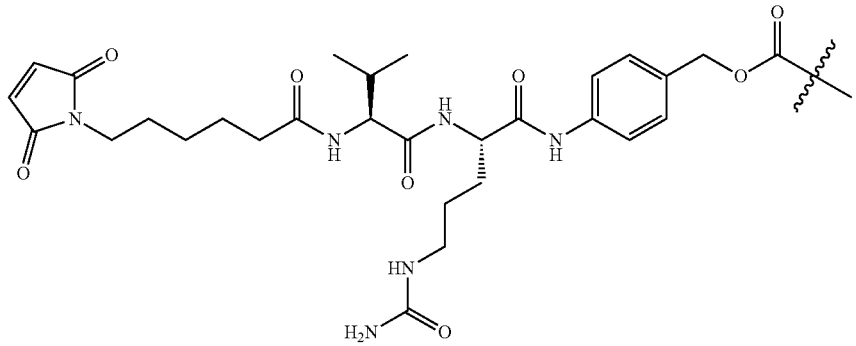

-continued
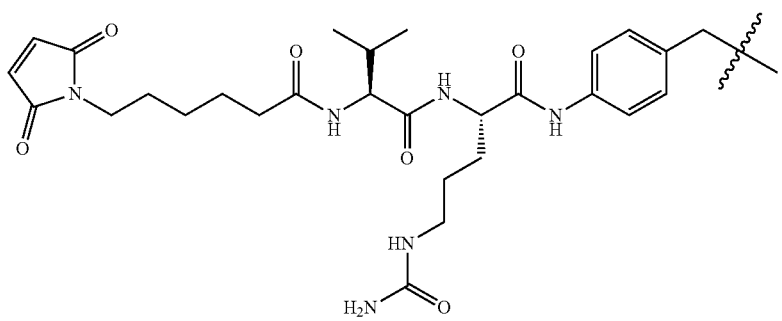
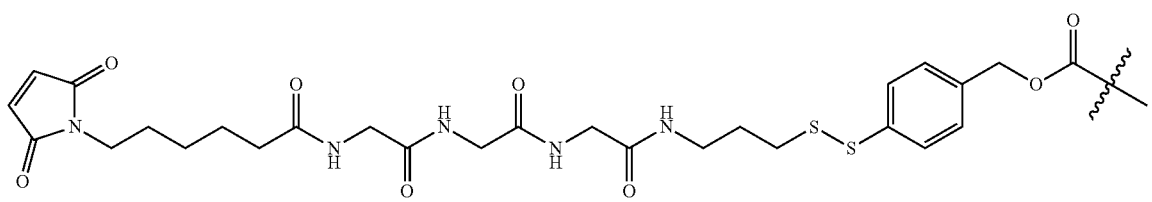
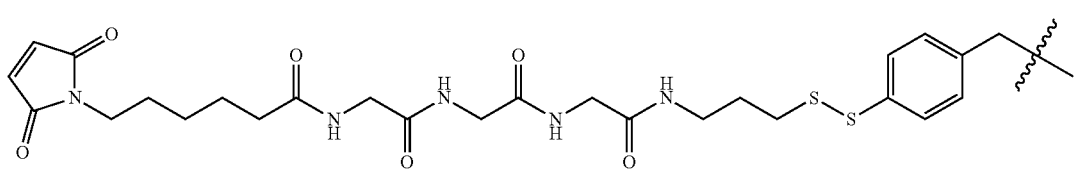
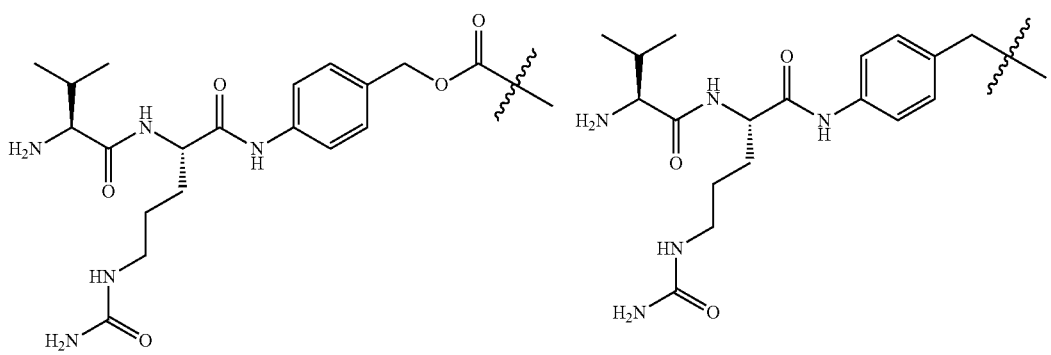
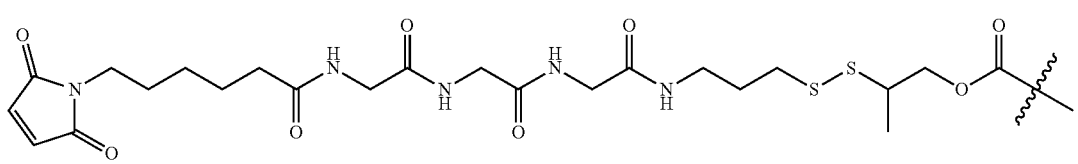
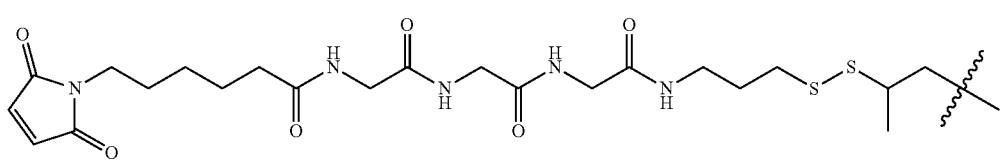
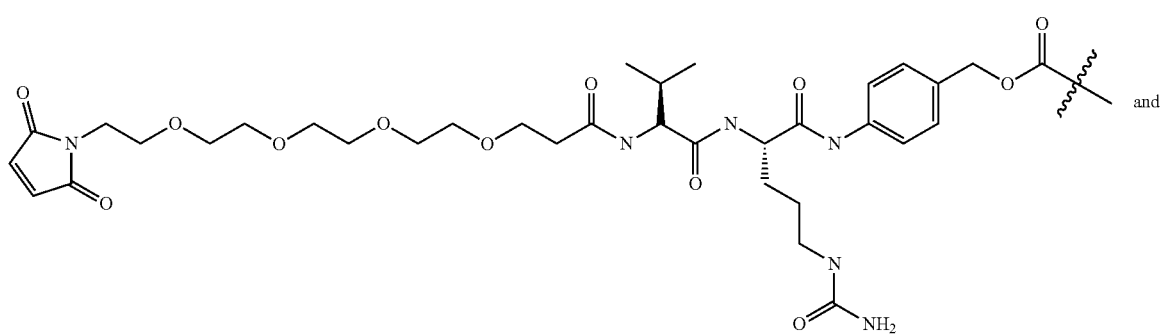
and

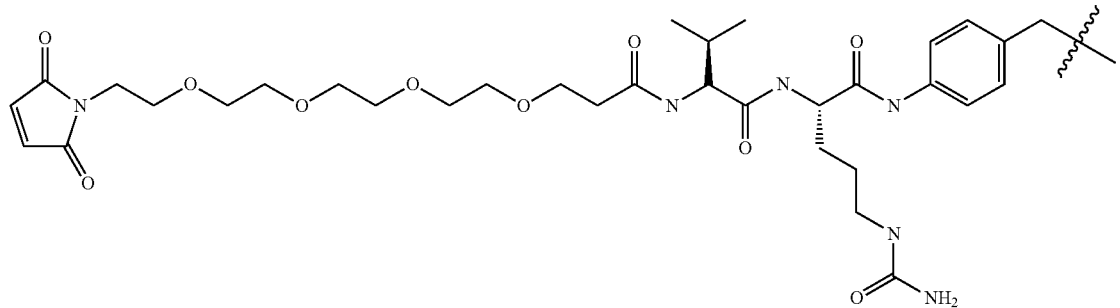
According to another preferred embodiment, the compound is selected from among:
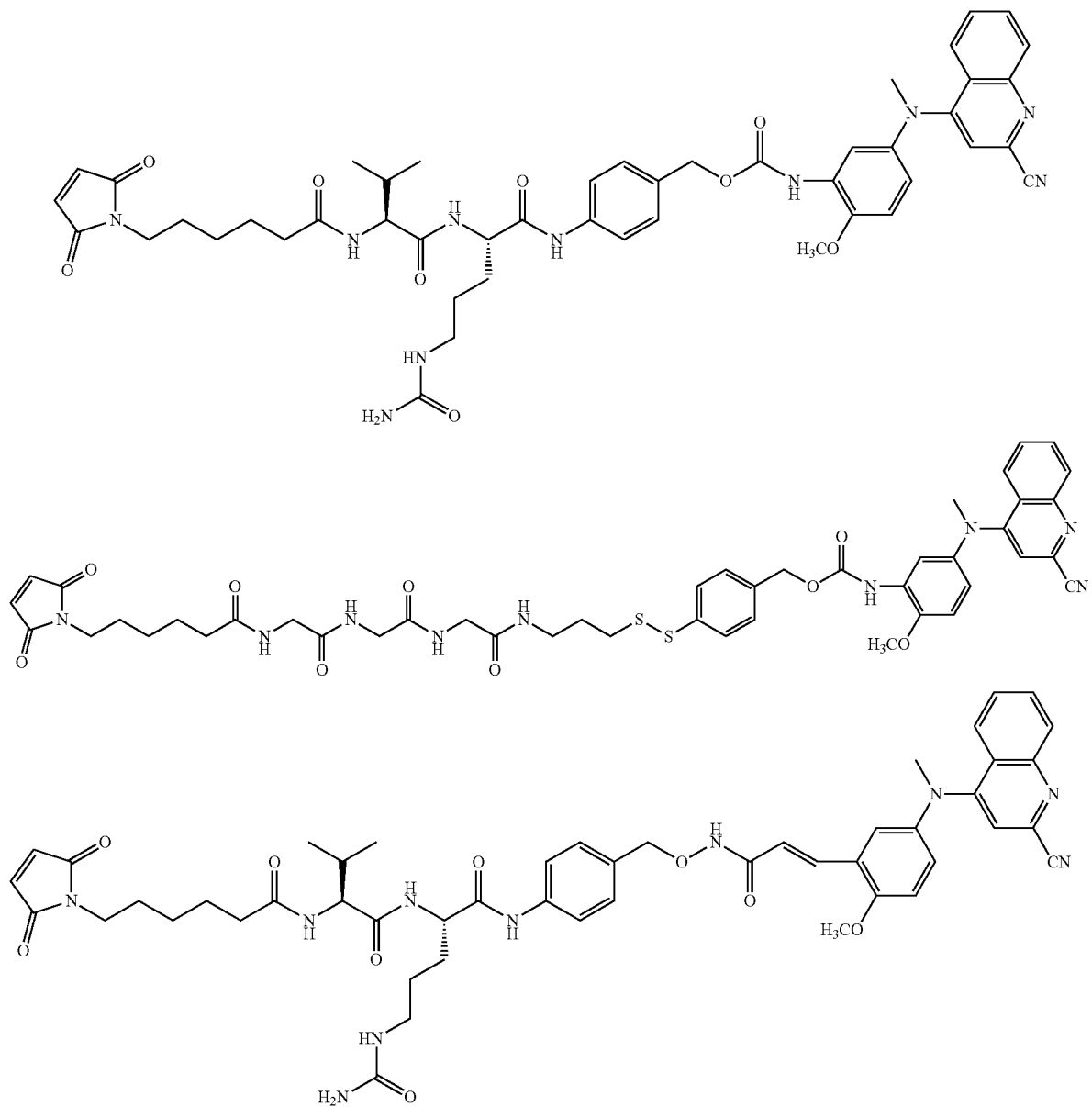

-continued

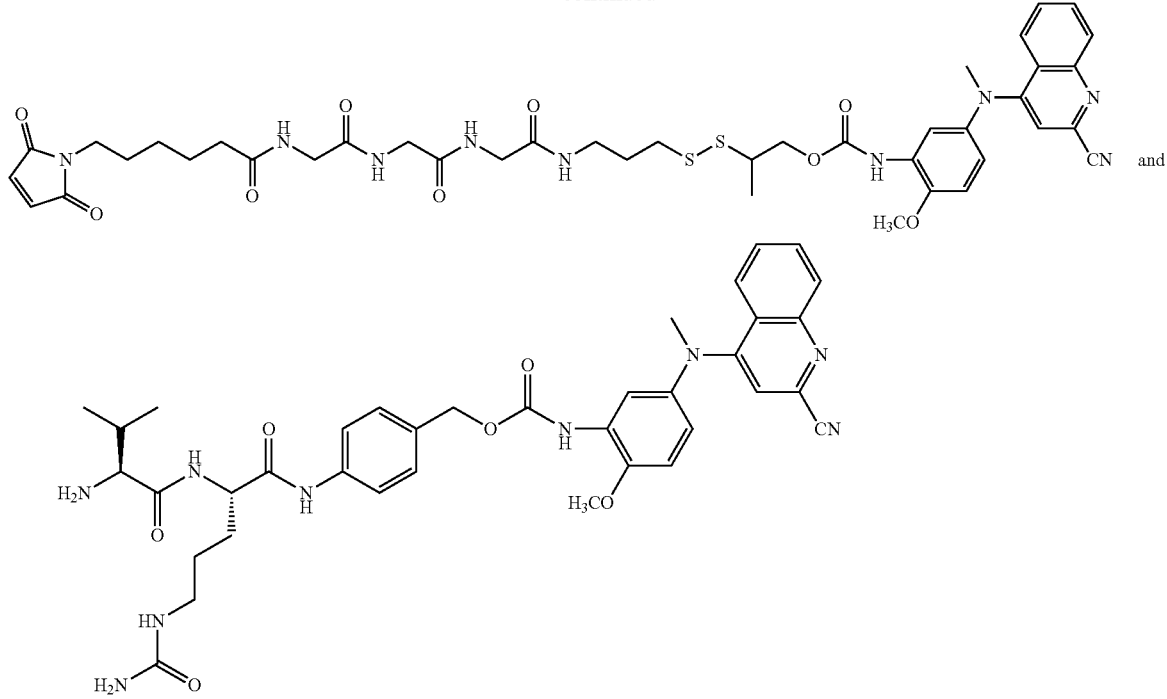

and

Linking Agent (Linker)

A linking agent or "linker" according to the present invention is a compound that links two constituent components, each one being attached to one end of the linking agent.

In the case where the linking agent is a covalent bond, direct binding of the toxic compound ("payload") to the targeting agent, such as an antibody, can reduce the ability of the payload to interact with the targeted molecule within the cell.

According to preferred embodiments, the linker increases the distance between the two components, in particular between the payload and the targeting agent, and thus attenuates steric interference between them.

In particular, the linker has a continuous chain comprising from 1 to 30 atoms in its backbone, the length of the linker being defined as the lowest number of atoms or bonds between the payload and the targeting agent.

According to one particular embodiment, the linker is selected from among the groups $C_1$-$C_{20}$-alkylene, $C_1$-$C_{20}$-heteroalkylene, $C_2$-$C_{20}$-alkenylene, $C_2$-$C_2O$— heteroalkenylene, $C_2$-$C_{20}$-alkynylene, $C_2$-$C_{20}$-heteroalkynylene, cycloalkylene, heterocycloalkylene, arylene, heteroarylene, aralkylene, or heteroaralkylene, optionally substituted. The linker may contain one or more elements such as a carboxamide, an ester, an ether, a thioether, a disulfide, a urea, a thiourea, a hydrocarbon moiety, or one of the derivatives thereof. The linker may contain one or more of these structural elements. Each of these elements may be present in the linker one or more times, for example two, three, four, five or even six times.

According to one particular embodiment, the linker may comprise a disulfide bond.

It is understood that the linker must be attached in one single step or in multiple steps, for example two, successive steps, to the payload and to the targeting agent. To this end, the linker has two groups, in particular at the proximal and distal ends, which can (i) form a covalent bond with a group that is present in one of the components to be linked, in particular a group that is activated on the payload or on the targeting agent, or (ii) which is or can be activated so as to form a covalent bond on a group of the payload.

Thus, according to one preferred embodiment, the chemical groups present at the ends of the linker, resulting from the coupling reaction, are selected from among esters, ethers, urethanes, peptide bonds, etc.

According to one particular embodiment, the linker L is a linear chain comprising from 1 to 20 atoms, selected independently of one another from C, O, N and S, in particular comprising from 2 to 18 atoms, more particularly between 5 and 16 atoms, and preferably between 6 and 15 atoms.

According to one particular embodiment, at least 60% of the atoms of the linear chain are carbon atoms. In particular, the atoms of the linear chain are linked by single bonds.

According to one particular embodiment, the linker L is a group selected from among alkylene, heteroalkylene, alkenylene, heteroalkenylene, alkynylene, heteroalkynylene, cycloalkylene, heterocycloalkylene, arylene, heteroarylene, aralkylene, or heteroaralkylene, comprising from 1 to 4 heteroatoms selected from N, O, and S, the said linker being optionally substituted.

According to one particular embodiment, the linker L comprises at least one of the following groups: a disulfide (—SS—), an ether (—O—), a thioether (—S—), an amine (—NH—), an ester (—O—C(=O)— or —C(=O)—O—), a carboxamide (—NH—C(=O)— or C(=O)—NH—), a urethane (—NH—C(=O)—O— or —O—C(=O)—NH—), or a urea moiety (—NH—C(=O)—NH—).

According to one particular embodiment of the present invention, the linker L comprises a number m of groups selected from among alkylene, alkenylene, alkynylene, cycloalkylene, heteroalkylene, heteroalkenylene, heteroalkynylene, heterocycloalkylene, arylene, heteroarylene, aralkylene, and heteroaralkylene, each of these groups possibly being substituted, and a number n of groups selected independently of one another from at least one of the following groups: a disulfide (—SS—), an ether (—O—), a thioether (—S—), an amine (—NH—), an ester (—O—C(=O)— or —C(=O)—O—), a carboxamide (—NH—C(=O)— or C(=O)—NH—), a urethane (—NH—C(=O)—O— or —O—C(=O)—NH—), or a urea moiety (—NH—C(=O)—NH—), m being equal to n+I. In particular, m is 2 and n is 1, or m is 3 and n is 2. More particularly, the linker comprises 2 or 3 unsubstituted alkylene groups, and 1 or 2, respectively, disulfide, ether, thioether, amine, ester, carboxamide, urethane or urea moiety linked to unsubstituted alkylene groups.

According to one particular embodiment, the carbon atoms in the linear chain independently form part of optionally substituted methylene groups (—CH$_2$—). In particular, the optional substituents are independently selected from halogens and the —(C$_1$-C$_6$)alkyl groups, especially methyl.

In particular, the linker L is a stable linking agent, that is to say that it is stable (i) in the presence of enzymes, and (ii) in an intracellular reducing environment.

According to one particular embodiment, the stable linker does not contain (i) a cleavable enzymatic substructure and/or (ii) a disulfide group. In particular, the linker has a length ranging up to 12 atoms, in particular a length ranging from 2 to 10 atoms, more particularly from 4 to 9, and even more particularly from 6 to 8.

According to one other particular embodiment, the linker is a cleavable linking agent, that is to say (i) that it is cleavable by chemical cleavage, or (ii) that it is a reducible linking agent.

According to one embodiment, the linking agent is cleavable by reduction, that is to say that it can be cleaved in an intracellular reducing environment. In particular, it may be a linker containing disulfide groups, resulting in the intracellular release of the payload conjugated to the targeting agent after internalisation by the intracellular reducing environment (Shen et al., (1985), *J Biol. Chem.* 260: 10905-10908).

According to one particular embodiment, the linking agent comprises a disulfide bond, in particular a —CMe$_2$-S—S—CMe$_2$- moiety. According to other embodiments, the linker is attached to a thiol group of a targeting agent moiety through a disulfide bond.

According to other embodiments, the linker is cleavable by chemical cleavage, in particular by hydrolysis or proteolysis. In particular, the chemical cleavage is catalyzed by an enzyme, that is to say, the linker may be cleaved by an enzyme, in particular a lysosomal peptidase, such as Cathepsin B, resulting in an intracellular release of the payload conjugated to the targeting agent after internalisation (Dubowchik et al., (2002) *Bioconjug Chem.* 13:855-69). According to one particular embodiment, the cleavable linker comprises a dipeptide selected from Phenylalanyl-lysine (Phe-Lys), Valyl-lysine (Val-Lys), Phenylalanyl-alanine (Phe-Ala), Valyl-alanine (Val-Ala), Phenylalanyl-citrulline (Phe-Cit) and valine-citrulline (Val-Cit). In particular, the cleavable linker in addition comprises a p-aminobenzyl (PAB) spacer between the dipeptides and the payload.

According to one embodiment, the linker comprises a hydrazone group. In this particular embodiment, the cleavage occurs by hydrolysis in the lysosome.

According to one embodiment, the linker is a self-immolative linking agent, that is to say that it comprises a cleavable bond. In particular, after cleavage, a fragmentation occurs which removes a part of the linker that remains attached to the payload after the said cleavage. In particular, the linker may comprise a group: -(cleavable bond)-X-phenyl-CH$_2$—O—C(=O)—, in which the carbonyl group is attached to the amino group that is attached to the phenyl ring in the compounds according to the invention, the compound according to the invention that comprises a free amino group being released.

According to one preferred embodiment, the linking agent is selected from the following compounds:

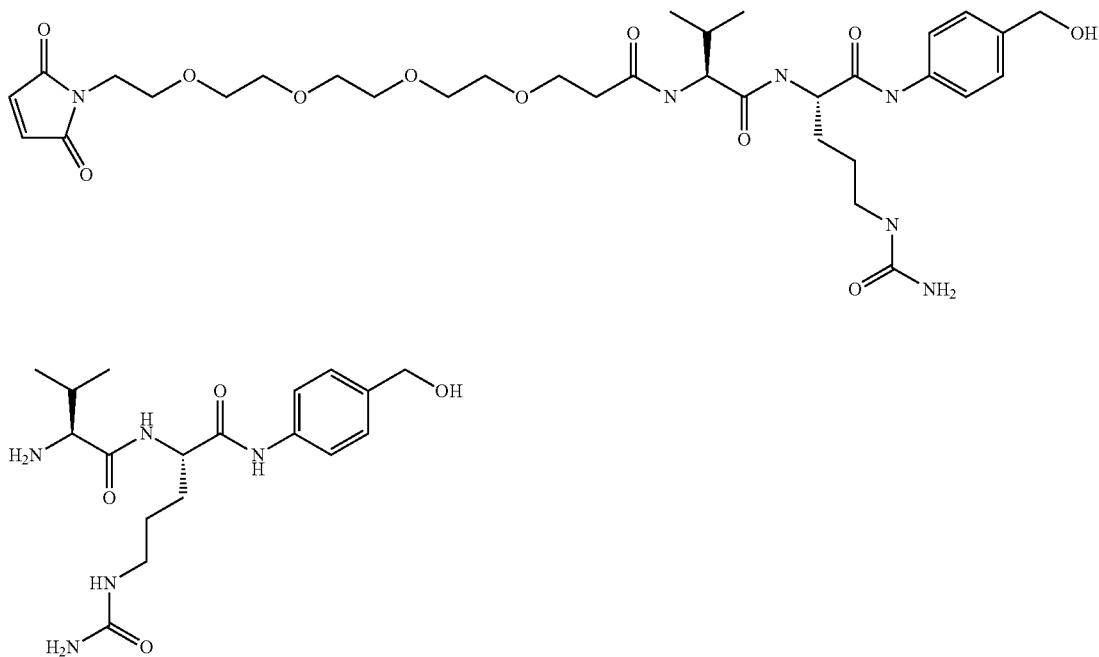

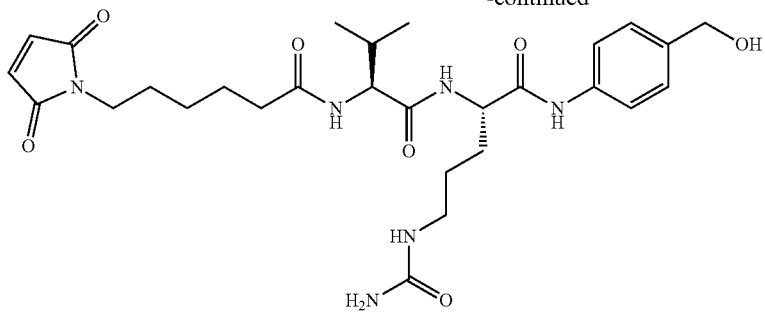

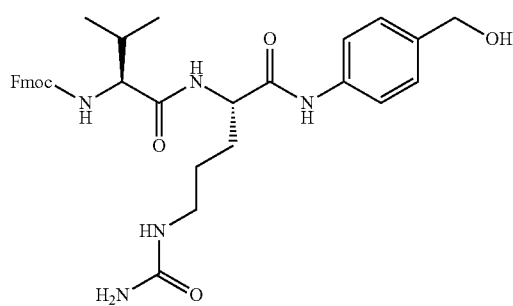

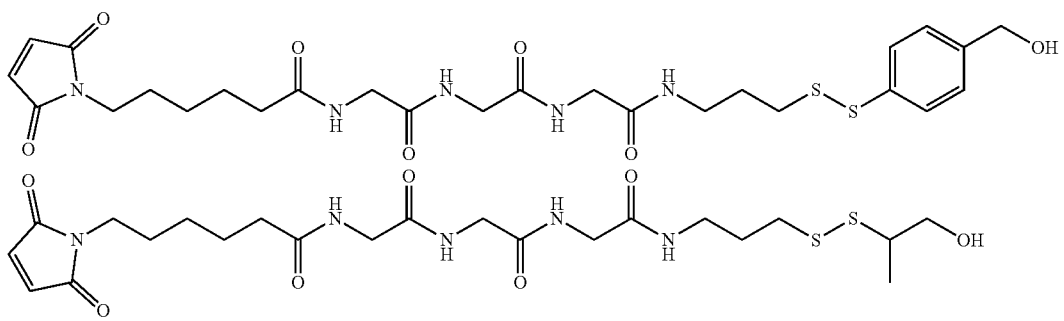

By way of linkers that are suitable for the present invention, mention may also be made of the linkers described in Jun Lu et al. ("Linker shaving a crucial role in antibody-drug conjugates", *Int. J. Mol. Sci.* 2016, 17, 561), Jessica R. McCombs and Shawn C. Owen ("*Antibody drug conjugates: Design and selection of linker, payload and conjugation chemistry*", *The AAPS Journal*, vol. 17, No. 2, March 2015, 339), Laurent Ducry and Bernhard Stmmp ("*Antibody-drug conjugates: linking cytotoxic payloads to monoclonal antibodies*", *Bioconjugate Chem.* 2010, 21, 5-13), and Nareshkumar Jain et al. ("*Current ADS linker chemistry*, *Pharm. Res.* 2015, 32: 3526-3540).

Antibody-Drug Conjugates

The present invention also relates to antibody-drug conjugates that comprise the compounds as defined above.

According to yet another of its aspects, the present invention relates to antibody-drug conjugates having the formula (III):

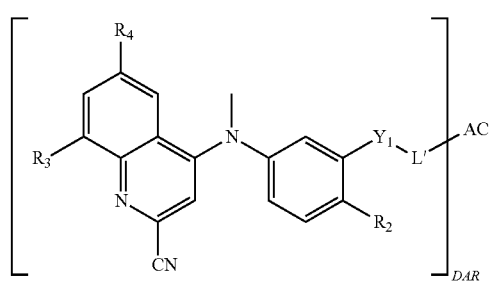

(III)

wherein:

$Y_1$ represents —O—, —NH—, —NHCO—, —NHCOR$_a$—, —NHCOO—, —NHCOOR$_b$—, —(C$_2$-C$_6$)alkenylene-CO—NH—O— or —(C$_2$-C$_6$)alkenylene-CO—NH—O—;

$R_2$ represents a group: —OCH$_3$, —OCH$_2$CH$_3$, —SCH$_3$, —SCH$_2$CH$_3$ or —OCHF$_2$;

R$_3$ represents a hydrogen atom or a group: —CH$_3$, —CN, —F, —Cl or —OR; and preferably a hydrogen atom;

R$_4$ represents a hydrogen atom or a group: —CH$_3$, —CN, —F, —Cl or —OR; and preferably a hydrogen atom;

R$_a$ represents a group: —(C$_1$-C$_5$)alkylene- or —CF$_2$—;

R$_b$ represents a group: —(C$_1$-C$_5$)alkylene- or —CF$_2$—;

R$_c$ represents a group: —(C$_1$-C$_5$)alkyl;

R$_d$ represents a group: —(C$_1$-C$_5$)alkyl or —CF$_3$;

L' represents a linking agent (linker);

AC represents a targeting agent moiety, in particular an antibody moiety or a functional fragment thereof; and wherein the DAR (drug-to-antibody [targeting agent] ratio) varies between 1 and 8, and preferably between 2 and 4.

Targeting Agent

The term "targeting agent" is understood to refer to a molecule that has an affinity for a biological target. The targeting agent has the function of directing the cytotoxic compound to the biological target.

The term "biological target" is understood to refer to an antigen, or a group of antigens, preferably located on the surface of cancer cells. These antigens, for example, may be a growth factor receptor, a mutated "tumour suppressor" oncogene product or gene, an angiogenesis-related molecule, or an adhesion molecule.

In particular, the targeting agent is selected from among a ligand, a protein, an antibody, for example a monoclonal antibody, a protein or antibody fragment, a peptide, an oligonucleotide, or an oligosaccharide.

Preferably, it is an antibody (or immunoglobulin) or an antibody fragment.

By way of antibodies that are suitable for the present invention, in particular mention may be made of the immunoglobulins IgA, IgD, IgE, IgG and IgM.

The antibodies may be monoclonal antibodies, polyclonal antibodies, recombinant antibodies, chimeric antibodies, humanised antibodies or optimised antibodies, for example antibodies with modified glycosylation or antibodies having a variant Fc region exhibiting an optimised binding affinity with one or more Fc receptors. In particular, it is a monoclonal antibody.

More particularly, the antibody may be selected from:

anti-nuclear antibodies, comprising anti-SSA/Ro (anti-Sjögren's-syndrome-related antigen A or anti-Ro) auto-antibodies, anti-La/SS-B (Anti-Sjögren's syndrome type B) auto-antibodies, anti-centromere antibodies, anti-neuronal nuclear antibody-type 2, anti-dsDNA (anti-double stranded DNA), anti-RNP (anti-ribonucleoprotein), anti-Smith, anti-topoisomerase antibody, anti-histone antibodies, anti-p62 antibodies, and anti-sp100 antibodies;

anti-glycoprotein 210 antibodies;

anti-transglutaminase antibodies, comprising anti-tTG (anti-tissue transglutaminase) antibodies and anti-eTG (anti-epidermal transglutaminase) antibodies;

anti-ganglioside antibodies;

anti-actin antibodies;

anti-CCP (anti-cyclic citrullinated peptides) antibodies, liver and kidney microsome type 1 antibodies;

anti-thrombin antibodies;

anti-neutrophil cytoplasmic antibodies (ANCA) comprising anti-myeloperoxidase (MPO), anti-proteinase 3 (PR3), anti-lactoferrin, anti-elastase, bacterial inducing protein (BPI), anti-cathepsin G;

the anti-glomerular basement membrane (alpha-3 chain of type IV collagen), the anti-phospholipase A2 receptor (PLA2R);

anti-rheumatoid factor antibodies;

anti-smooth muscle antibody, comprising anti-actin antibodies, anti troponin antibodies, and anti-tropomyosin antibodies;

anti-mitochondrial antibodies, including anti-cardiolipin antibodies, anti-sulfite oxidase antibodies, anti-sarcosine dehydrogenase antibodies and anti-glycogen phosphorylase antibodies;

anti-SRP (signal recognition particle) antibodies;

anti-VGCC (voltage-gated calcium channel) antibodies;

anti-VGKC antibodies (voltage-gated potassium channel);

anti-synthetase antibodies comprising anti-PL7, -PL12, -JO1, -EJ, and -JO antibodies;

and anti-terminal complement antibodies, including anti-factor H autoantibodies, anti-Cl inhibitor, anti-C1q, anti-C3, anti-factor B, anti-C3bBb (C3 convertase from the alternative complement pathway), anti-C4b2a (C3 convertase from the classical complement pathway).

By way of allo-antibodies, mention may be made of human platelet antigen antibodies (HPA) and anti-IgA antibodies.

By way of human therapeutic antibodies, mention may be made of those antibodies selected from the group comprising Panitumumab, Actoxumab, Adalimumab, Adecatumumab, Alirocumab, Anifrolumab, Atinumab, Atorolimumab, Belimumab, Bertilimumab, Bezlotoxumab, Bimagrumab, Briakinumab, Brodalumab, Canakinumab, Carlumab, Cixutumumab, Conatumumab, Daratumumab, Denosumab, Drozitumab, Duligotumab, Dupilumab, Dusigitumab, Efungumab, Eldelumab, Enoticumab, Evolocumab, Exbivirumab, Fasinumab, Fezakinumab, Figitumumab, Flanvotumab, Foralumab, Foravirumab, Fresolimumab, Fulranumab, Ganitumab, Gantenerumab, Glembatumumab vedotin, Golimumab, Guselkumab, Icrucumab, Inclacumab, Intetumumab, Ipilimumab, Iratumumab, Lerdelimumab, Lexatumumab, Libivirumab, Lirilumab, Lucatumumab, Mapatumumab, Mavrilimumab, Metelimumab, Morolimumab, Namilumab, Narnatumab, Nebacumab, Necitumumab, Nesvacumab, Nivolumab, Ofatumumab, Olaratumab, Orticumab, Oxelumab, Panitumumab, Panobacumab, Parsatuzumab, Patritumab, Placulumab, Pritumumab, Radretumab, Rafivirumab, Ramucirumab, Raxibacumab, Regavirumab, Rilotumumab, Robatumumab, Roledumab, Sarilumab, Secukinumab, Seribantumab, Sevirumab, Sirukumab, Stamulumab, Tabalumab, Teprotumumab, Ticilimumab (=tremelimumab), Tovetumab, Tralokinumab, Tremelimumab, Tuvirumab, Urelumab, Ustekinumab, Vantictumab, Vesencumab, Votumumab, Zalutumumab, Zanolimumab, Ziralimumab.

By way of murine therapeutic antibodies, mention may be made of those antibodies selected from the group comprising Abagovomab, Afelimomab, Anatumomab mafenatox, Blinatumomab, Detumomab, Dorlimomab aritox, Edobacomab, Edrecolomab, Elsilimomab, Enlimomab pegol, Epitumomab cituxetan, Faralimomab, Gavilimomab, Ibritumomab tiuxetan, Imciromab, Inolimomab, Lemalesomab, Maslimomab, Minretumomab, Mitumomab, Moxetumomab pasudotox, Muromonab-CD3, Nacolomab tafenatox, Naptumomab estafenatox, Nerelimomab, Odulimomab, Oregovomab, Pemtumomab, Racotumomab, Solitomab, Taplitumomab paptox, Telimomab aritox, Tenatumomab, Tositumomab, Vepalimomab and Zolimomab aritox.

By way of chimeric therapeutic antibodies, mention may be made of those antibodies selected from the group comprising Abciximab, Amatuximab, Basiliximab, Bavituximab, Brentuximab vedotin, Cetuximab, Clenoliximab, Ecromeximab, Ensituximab, Futuximab, Galiximab, Girentuximab, Gomiliximab, Indatuximab ravtansine, Infliximab, Keliximab, Lumiliximab, Pagibaximab, Priliximab, Pritoxaximab, Rituximab, Setoxaximab, Siltuximab, Teneliximab, Ublituximab, Vapaliximab, Volociximab and Zatuximab.

By way of humanised therapeutic antibodies, mention may be made of those antibodies selected from the group comprising Afutuzumab, Alacizumab pegol, Alemtuzumab, Anrukinzumab, Apolizumab, Aselizumab, Atlizumab (=tocilizumab), Bapineuzumab, Benralizumab, Bevacizumab, Bivatuzumab mertansine, Blosozumab, Cantuzumab mertansine, Cantuzumab ravtansine, Caplacizumab, Cedelizumab, Certolizumab pegol, Citatuzumab bogatox, Clazakizumab, Clivatuzumab tetraxetan, Concizumab, Crenezumab, Dacetuzumab, Daclizumab, Dalotuzumab, Demcizumab, Eculizumab, Efalizumab, Elotuzumab, Enavatuzumab, Enokizumab, Epratuzumab, Erlizumab, Etaracizumab, Etrolizumab, Farletuzumab, Felvizumab, Ficlatuzumab, Fontolizumab, Gemtuzumab ozogamicin, Gevokizumab, Ibalizumab, Imgatuzumab, Inotuzumab ozogamicin, Itolizumab, Ixekizumab, Labetuzumab, Lambrolizumab, Lampalizumab, Lebrikizumab, Ligelizumab, Lintuzumab, Lodelcizumab, Lorvotuzumab mertansine, Margetuximab, Matuzumab, Mepolizumab, Milatuzumab, Mogamulizumab, Motavizumab, Natalizumab, Nimotuzumab, Ocaratuzumab, Ocrelizumab, Olokizumab, Omalizumab, Onartuzumab, Oportuzumab monatox, Ozanezumab, Ozoralizumab, Palivizumab, Pascolizumab, Pateclizumab, Perakizumab, Pertuzumab, Pexelizumab, Pidilizumab, Pinatuzumab vedotin, Polatuzumab vedotin, Ponezumab, Quilizumab, Ranibizumab, Reslizumab, Romosozumab, Rontalizumab, Rovelizumab, Ruplizumab, Samalizumab, Sibrotuzumab, Sifalimumab, Simtuzumab, Siplizumab, Solanezumab, Sonepcizumab, Sontuzumab, Suvizumab, Tacatuzumab tetraxetan, Tadocizumab, Talizumab, Tanezumab, Tefibazumab, Teplizumab, Tildrakizumab, Tigatuzumab, Tocilizumab (=atlizumab), Toralizumab, Trastuzumab, Tregalizumab, Tucotuzumab celmoleukin, Urtoxazumab, Vatelizumab, Vedolizumab, Veltuzumab, Visilizumab and Vorsetuzumab mafodotin.

Preferably, it is a humanised therapeutic antibody, and more preferably Trastuzumab.

DAR

A conjugate generally comprises an average number of cytotoxic compounds (payload) of between 1 and 8, preferably between 2 and 4, linked to the targeting agent (this is the degree of grafting or "drug-to-antibody [ie targeting agent] ratio"(or "DAR")).

This number may notably vary depending on the nature of the targeting agent, the payload, or the conditions used during the conjugation.

In the case where the targeting agent is an antibody, the DAR may be determined for example by Ultraviolet (UV) spectroscopy or by deconvolution of the High-Resolution Mass Spectrometry HRMS spectrum of the conjugate.

The DAR assessed by UV spectroscopy is referred to as DAR (UV), as indicated in the method presented by Antony S. Dimitrov ((ed), LLC, 2009, "Therapeutic Antibodies and Protocols", vol. 525, 445, Springer Science). This method consists in measuring the absorbance of a solution of the conjugate after the separation step at two wavelengths WL1 and WL2. The molar extinction coefficients obtained from the naked antibody and from the payload before conjugation are used. The absorbances of the conjugate solution at WL1 and WL2, ($A_{WL1}$) and ($A_{WL2}$) are measured either on the corresponding UV peak of the size exclusion chromatography (SEC) spectra or using a standard UV spectrophotometer. The absorbances may be expressed in the following form:

$$A_{WL1}=(c_D \times e_{D\ WL1})+(c_A \times e_{A\ WL1})$$

$$A_{WL2}=(c_D \times e_{D\ WL2})+(c_A \times e_{A\ WL2})$$

in which:
$c_D$ and $c_A$ represent, respectively, the concentrations in the solution of the part of the conjugate relating to the payload and the part of the conjugate relating to the antibody;
$e_{D\ WL1}$ and $e_{D\ WL2}$ represent, respectively, the molar extinction coefficients of the payload prior to conjugation at the wavelengths WL1 and WL2;
$e_{A\ WL1}$ and $e_{A\ WL2}$ represent, respectively, the molar extinction coefficients of the naked antibody at the wavelengths WL1 and WL2.

The term "naked antibody" is understood to refer to the antibody to which no payload is attached, that is to say the antibody prior to conjugation.

Solving these two equations results in the following:

$$c_D=[(e_{A\ WL1} \times A_{WL2})-(e_{A\ WL2} \times A_{WL1})]/[(e_{D\ WL2} \times e_{A\ WL1})-(e_{A\ WL2} \times e_{D\ WL1})] c_A=[A_{WL1}-(c_D \times e_{D\ WL1})]/e_{A\ WL1}$$

The DAR(UV) then corresponds to $C_D/C_A$.

Alternatively, the DAR may be calculated by deconvolution of the HRMS spectrum of the conjugate and is then referred to as DAR (HRMS).

Preparation and Conjugation Method

The present invention also relates to a preparation method for preparing a compound having the formula (II) as defined above, characterised in that it includes a reaction step of reacting a compound having the formula (I) as defined above, with a compound having the formula X-L"-RM* wherein:
X represents a group that is capable of reacting with an $R_1$ group as defined above;
L" represents a linking agent (linker);
RM* is selected from RM and RM', wherein RM is a reactive functional group that is able to form a covalent bond with a targeting agent moiety, in particular with an antibody moiety or a functional fragment thereof, and wherein RM' is an RM moiety carrying at least one protecting group;
wherein the reaction between the —$R_1$ moiety of the compound having the formula (I) and the compound having the formula X-L"-RM* results in the formation of a —$Y_1$-L-RM* moiety.

According to one preferred embodiment, wherein RM* is RM, the method in addition includes a deprotection step of deprotecting an RM' moiety resulting in an RM group.

Preferably, the method includes a reaction step of reacting a compound having the formula (II) as defined above with a targeting agent moiety.

The conjugation to the targeting agent moiety may be achieved via coupling of a compound construct having the formula (I)-L-RM to the free amino groups present in the targeting agent moiety. According to such an embodiment, the RM group may be selected from an activated carboxylic acid derivative, such as an N-hydroxy succinimide ester, or an activated carbonic acid derivative, such as an isothiocyanate.

The conjugation to the targeting agent moiety may also be achieved via coupling of a compound construct having the formula (I)-L-RM to the free thiol groups present in the targeting agent moiety. According to such an embodiment, the RM group may be selected from a haloacetyl group, an RM group comprising a acceptor-substituted alkene (Michael system), in particular a maleimide group or a propenoyl group (Badescu et al., 2014, Bioconjugate Chem., 25: 460-469), a maleimide group substituted at position 3 or disubstituted at positions 3 and 4 by the leaving groups X, in particular selected from Cl, Br, and aryl-S—, in particular phenyl-S—.

According to one particular embodiment, the thiol group is part of a single, uncoupled cysteine residue present in the wild-type targeting agent moiety. According to one other particular embodiment, the thiol group is part of a single, uncoupled cysteine residue that has been generated from a wild type targeting agent moiety, in particular by recombinant genetic engineering, for example by insertion into the wild type sequence, by removing of a second cysteine that is forming a disulfide bridge with the first cysteine residue in the wild type targeting agent moiety, or by replacement of a non-cysteine residue. According to one other embodiment, the thiol group is generated by reduction of a disulfide bond between two cysteines present in the wild type targeting agent moiety.

The conjugation to the targeting agent moiety may also be achieved via coupling of a compound construct having the formula (I)-L-RM to two free thiol groups present in the targeting agent moiety. According to such an embodiment, the RM group may be selected from a maleimide group disubstituted at positions 3 and 4 with the leaving groups X, in particular selected from Cl, Br, and aryl-S—, in particular phenyl-S—.

According to one embodiment, the two thiol groups each form part of a single, uncoupled cysteine residue present in the wild type targeting agent moiety. According to one other particular embodiment, the thiol groups form part of two single, uncoupled cysteine residues that have been generated from a wild type targeting agent moiety, in particular by recombinant genetic engineering, for example by insertion into the wild type sequence, by removing of a second cysteine that is forming a disulfide bridge with the first cysteine residue in the wild type targeting agent moiety, or by replacement of a non-cysteine residue. According to one other embodiment, the two thiol groups are generated by reduction of a disulfide bond between two cysteines present in the wild type targeting agent moiety. By the reacting of such two thiol groups with a disubstituted maleimide, the thiol groups are bridged, thereby mimicking the disulfide bridge that was originally present.

According to one particular embodiment, a free thiol group may be generated by thiolation of free amino groups present in the targeting agent moiety, in particular by the reacting of such free amino groups with a thiolation agent selected from 2-iminothiolane (Still et al., 1984, *Can. J. Org. Chem.* 62:586) and a derivative of acylthioacetic acid (X—C(=O)—CH$_2$—SAcyl), such as an N-hydroxy succinimide ester of acetylthioacetic acid.

The conjugation to the targeting agent moiety may be achieved via coupling to unnatural amino acids introduced by genetic engineering, for example by the introduction of p-acetyl phenylalanine and subsequent oxime ligation (Kazane et al, (2012) *Proc. Natl. Acad. Sci. USA,* 109: 3731-3736).

The conjugation to the targeting agent moiety may be achieved via coupling of cyclic diazodicarboxamides to the phenyl ring of tyrosine residues in the targeting agent moiety (Ban et al, (2010) *J Am. Chem. Soc.* 13:1523-5).

The conjugation to the targeting agent moiety may be achieved via 1,3-dipolar cycloaddition ("click chemistry").

According to one embodiment, the targeting agent moiety comprises a double or a triple bond and the compound construct having the formula (I)-L-RM comprises a 1,3-dipole, in particular an azide group. In particular, the targeting agent moiety is first reacted with a dibenzocyclooctyne-N-hydroxysuccinimide ester or an azadibenzocyclooctyne-Nhydroxysuccinimide ester (Zhou et al, (2013) *J Am Chem Soc.* 135: 12994-7).

According to one other embodiment, the targeting agent moiety comprises a 1,3-dipole, in particular an azide group, and the compound construct having the formula (I)-L-RM comprises a double or a triple bond. In particular, the targeting agent moiety is a glycosylated antibody which is first caused to react with a molecule containing an azide by an enzyme catalysed reaction (SiteClick; Zeglis et al, (2013) *Bioconjug Chem.* 24: 1057-67). According to one other embodiment, the azido group is incorporated via the unnatural amino acid p-azido-phenylalanine (Kazane et al, (2012) *Proc. Natl. Acad. Sci. USA,* 109: 3731-3736).

Pharmaceutical Use

The present invention also relates to a pharmaceutical composition comprising an antibody-drug conjugate as defined above, in association with a pharmaceutically acceptable carrier.

In particular, a pharmaceutical composition according to the invention may comprise at least one pharmaceutically acceptable excipient.

The pharmaceutical composition may include one or more pharmaceutically acceptable diluents, carriers, excipients, fillers, binders, lubricants, glidants, disintegrants, absorbents, and/or preservatives.

The invention also relates to the pharmaceutical compositions according to the invention for the use thereof as a medicinal product, in particular intended for treating cancer.

The present invention also relates to an antibody-drug conjugate as defined above, or a pharmaceutical composition as defined above, for the use thereof as a medicinal product.

The present invention also relates to an antibody-drug conjugate as defined above or a pharmaceutical composition as defined above, for the use thereof for killing or inhibiting cell growth.

The present invention also relates to an antibody-drug conjugate as defined above or a pharmaceutical composition as defined above, for the use thereof in the treatment of cancer.

Among the cancers, mention may be made, without any limitation, of various leukemias, for example chronic myeloid leukemia, lymphomas, sarcomas, melanoma, liver cancer, pancreatic cancer, lung cancer, cancer of the stomach, esophageal cancer, kidney cancer, pleural cancer, thyroid cancer, skin cancer, cervical cancer, breast cancer, ovarian cancer, colorectal cancer, testicular cancer, prostate cancer, bladder cancer, brain cancer, rectal cancer, or bone cancer.

In particular, mention may be made of colorectal cancer, lung cancer, in particular non-small cell cancer, cancer of the stomach, pancreatic cancer, chronic myeloid leukemia, breast cancer, and ovarian cancer, and more particularly breast cancer.

In particular, the patient in need of treatment is a mammal, especially a human.

The present invention also describes a treatment method for the treatment of cancer, that comprises the administering of an effective amount of at least one antibody-drug conjugate according to the invention, in particular to a patient in need thereof.

According to one particular embodiment, the pharmaceutical compositions according to the invention are used in the form of a systemically administered medicament.

Thus, the pharmaceutical compositions according to the invention may be intended for administration by the parenteral route. The term parenterals, is intended to include injectables and infusions.

The injectables may be formulated either in the form of ampoules or in the form of ready-to-use injectables, for example ready-to-use syringes or single-use syringes, or indeed even in puncturable vials for multiple withdrawal. The administration of injectables can be done in the form of subcutaneous (s.c.), intramuscular (i.m.), intravenous (i.v.) or intracutaneous (i.e.) application. In particular, it is possible to produce the appropriate injectable formulations in the form of a suspension of crystals, solutions, nanoparticles or colloidal dispersion systems, such as for example hydrosols.

The injectable compositions can in addition be produced in the form of concentrates, which may be dissolved or dispersed with isotonic aqueous diluents. The infusions can also be prepared in the form of isotonic solutions, fatty emulsions, liposomal formulations and microemulsions. Similar to the injectables, infusion preparations may also be prepared in the form of concentrates for dilution. Injectable formulations can also be applied in the form of permanent infusions in the context of both hospital in-patient and ambulatory therapy, for example by means of mini-pumps.

It is possible to add to parenteral drug compositions, for example albumin, plasma, diluents, surfactants, organic diluents, pH influencing substances, complexing substances or polymeric substances, in particular as substances for influencing the adsorption of the conjugates according to the invention to proteins or polymers, or they can also be added with the aim of reducing the adsorption of the conjugates of the invention to materials such as injection instruments or packaging materials, for example plastic or glass.

The compounds according to the invention comprising a targeting agent moiety can be bound to microcarriers or to parenteral nanoparticles, for example to finely dispersed particles based on poly(meth)acrylates, polylactates, polyglycolates, polyamino acids or polyether urethanes. Parenteral compositions can also be modified as depot preparations, for example on the basis of the "multiple unit principle", if the conjugates of the present invention are introduced in finely dispersed, or in suspension form, respectively, or in the form of a suspension of crystals in the medicament or on the basis of the "single unit principle" if the conjugate of the invention is enclosed in a formulation, for example in a tablet or a rod which is subsequently implanted. These implants or drug depots in single unit and multiple unit formulations often consist of so-called biodegradable polymers, for example polyesters of lactic acid and glycolic acid, polyether urethanes, polyamino acids, poly(meth)acrylates or polysaccharides.

The adjuvants and carriers added during the preparation of the pharmaceutical compositions according to the present invention formulated as parenteral products are in particular selected from sterilised water (aqua sterilisata), pH value influencing substances such as organic or inorganic acids or bases or the salts thereof, buffering substances for adjusting the pH values, substances for isotonisation such as sodium chloride, sodium hydrogen carbonate, glucose and fructose, surfactants and emulsifiers, such as partial esters of fatty acids of polyoxyethylene sorbitans (for example, Tween®) or fatty acid esters of polyoxyethylenes (for example, Cremophor @), fatty oils such as peanut oil, soybean oil or castor oil, synthetic esters of fatty acids such as ethyl oleate, isopropyl myristate and neutral oil (for example, Miglyol®), as well as polymeric adjuvants such as gelatin, dextran, polyvinylpyrrolidone, additives which increase the solubility of organic solvents, such as propylene glycol, ethanol, N,N-dimethylacetamide, propylene glycol or complex forming substances such as citrate and urea, preservatives such as benzoic acid hydroxypropyl ester and methyl ester, benzyl alcohol, antioxidants such as sodium sulfite and stabilisers such as EDTA.

According to one preferred embodiment, during the formulating of the pharmaceutical compositions according to the present invention, the method includes adding thickening agents so as to prevent the setting of the conjugates of the invention, or surfactants and polyelectrolytes so as to ensure the resuspendability of sediments and/or complex forming agents such as EDTA. It is also possible to obtain complexes of the active ingredient with various polymers. Examples of such polymers are polyethylene glycol, polystyrene, carboxymethyl cellulose, Pluronics® or a polyethylene glycol sorbitol fatty acid ester. The conjugates of the invention can also be incorporated into liquid formulations in the form of inclusion compounds, for example with cyclodextrins. According to one particular embodiment, dispersing agents can be added as additional adjuvants. For the production of lyophilisates, agents such as mannite, dextran, sucrose, human albumin, lactose, polyvinylpyrrolidone (PVP) or varieties of gelatin can be used.

For parenteral administration, the composition may be in the form of an aqueous suspension or a solution which may contain suspending agents and/or wetting agents. The composition is advantageously sterile. It may be in the form of an isotonic solution (in particular in relation to blood).

The compounds according to the invention may be used in a pharmaceutical composition at a dose ranging from 0.01 mg to 1000 mg per day, administered in a single dose once a day or in multiple doses during the day.

The dose administered daily is advantageously between 5 mg and 500 mg, and more advantageously between 10 mg and 200 mg.

However, it may be necessary to use doses outside these ranges, which the person skilled in the art would be able to appreciate.

According to one particular embodiment of the invention, the compounds in order for use thereof according to the invention, are administered in combination with another active ingredient, in particular an anti-cancer compound, whether or not cytotoxic.

Thus, the pharmaceutical composition according to the present invention may also comprise another active ingredient.

Thus, the pharmaceutical composition according to the invention comprises at least one antibody-drug conjugate as defined above and at least one other active ingredient by way of a combination product for simultaneous or separate use or for use spread out over a period of time, which can in particular be used for the treatment of cancer.

Throughout the entire description, including the claims, the term "comprising a" is to be understood as being synonymous with "comprising at least one", unless otherwise specified. The expressions "between . . . and . . . " and "ranging from . . . to . . ." are to be understood as inclusive of limits, unless otherwise specified.

In the description and the examples, the temperature is expressed in degrees Celsius unless otherwise indicated, and the pressure is atmospheric pressure, unless otherwise indicated.

The invention is illustrated in greater detail by means of the non-limiting examples presented here below.

BRIEF DESCRIPTION OF THE DRAWINGS

FIGS. 2A and 2B are renderings of TABLE 8 below, in which color is used to further describe the content.

DESCRIPTION OF THE PREFERRED EMBODIMENTS

Examples

Figure 1:
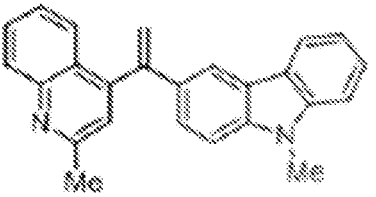
FIG. 1 is a rendering of TABLE 4 below, in which color is used to further describe the content.
Figure 1:
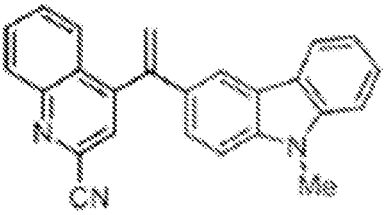
Figure 1:
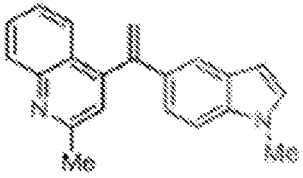
Figure 1:
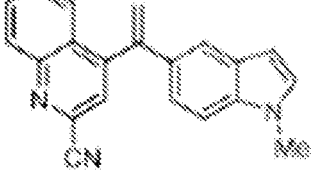

Example 1: Preparation of 4-((3-amino-4-methoxyphenyl)(methyl)amino) quinoline-2-carbonitrile 1.1 General Schematic Representation

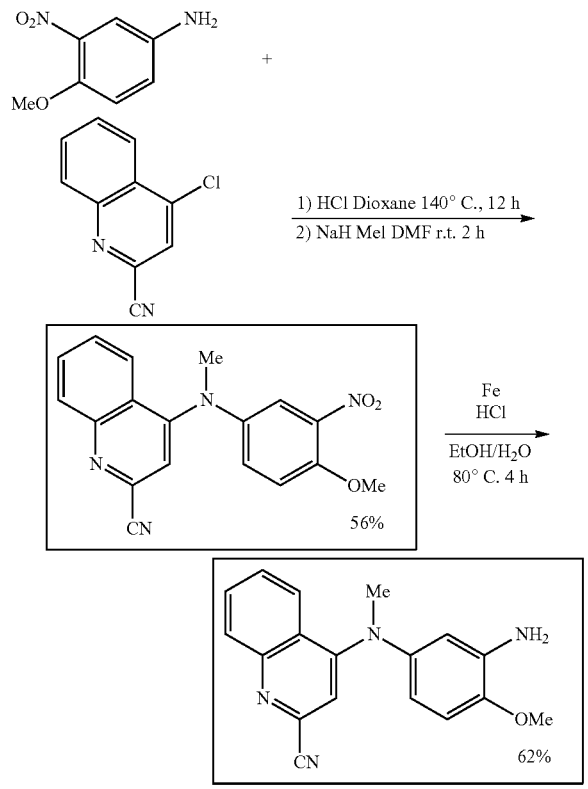

1.2 Preparation of 4-((4-methoxy-3-nitrophenyl)(methyl)amino)quinoline-2-carbonitrile In a sealed tube the chlorinated heterocyclic compound and the aromatic amine derivative are successively added in 2 ml of dioxane.

One drop of HCl is then added to the mixture and the reaction medium is heated to 140° C., with agitation, for a period of 12 hours.

The mixture is cooled, and thereafter neutralised with $NaOH_{aq}$. (5N) and the mixture is extracted with ethyl acetate (3×10 mL).

The combined organic phases are dried over $Na_2SO_4$ and concentrated under vacuum. The crude reaction mixture is dissolved in a Dimethylformamide (DMF) solution (5 mL) containing NaH at 0° C. To this mixture $CH_3I$ is added drop by drop and the reaction medium is placed at ambient temperature, under agitation, for a period of 2 hours.

The crude reaction mixture is concentrated and purified by means of chromatography on a silica column.

4-((4-methoxy-3-nitrophenyl)(methyl)amino) quinoline-2-carbonitrile is obtained in solid form with a yield of 56%.

The melting temperature measured is 219.9-220.5° C.

Characterisation $^1$H NMR (300 MHz, $CDCl_3$) δ: 8.11 (d, J=8.5 Hz, 1H); 7.71 (t, J=8.5 Hz, 1H); 7.61 (d, J=8.5 Hz, 1H); 7.58 (d, J=2.7 Hz, 1H); 7.42 (t, J=8.5 Hz, 1H); 7.34 (s, 1H); 7.05 (dd, J=9.1 Hz, J=2.8 Hz, 1H); 6.98 (d, J=9.1 Hz, 1H); 3.94 (s, 3H); 3.52 (s, 3H).

Characterisation $^{13}$C NMR (75 MHz, $CDCl_3$) δ: 153.9; 150.0; 149.3; 142.1; 139.9; 134.3; 130.9; 130.8; 128.2; 127.4; 124.5; 123.6; 118.4; 117.6; 114.9; 114.5; 56.9; 42.9.

Characterisation HRMS $C_{18}H_{15}N_4O_3$: 335.1144 (calculated); 335.1150 (observed).

Characterisation IR neat $v_{max}/cm^{-1}$: 2363, 2340, 1679, 1625, 1603, 1460, 1275.

1.3 Preparation of 4-((3-amino-4-methoxyphenyl)(methyl)amino) quinoline-2-carbonitrile In a 25 mL bicol, the nitro compound is added to an ethanol/water mixture [8/2]. The reaction medium is heated to 80° C. and solid iron (10 equivalents) and 3 drops of HCl are added to the reaction medium. The whole mixture is heated to 80° C., under agitation, until the nitro compound is completely reduced.

The crude reaction mixture is cooled to ambient temperature and filtered on filter paper. The filtrate is concentrated and purified by means of chromatography on a silica column and the reduced product is thus obtained.

The 4-((3-amino-4-methoxyphenyl)(methyl)amino) quinoline-2-carbonitrile is obtained in solid form with a yield of 62%.

The melting temperature measured is 84.9-92.6° C.

Characterisation $^1$H NMR (300 MHz, $CDCl_3$) δ: 7.98 (d, J=8.4 Hz, 1H); 7.59 (t, J=9.2 Hz, 2H); 7.26 (d, J=8.3 Hz, 1H); 6.68 (d, J=8.5 Hz, 1H); 6.46 (d, J=2.5 Hz, 1H); 6.36 (dd, J=8.5 Hz, J=2.5 Hz, 1H); 3.88 (s, 2H); 3.84 (s, 3H); 3.42 (s, 3H).

Characterisation $^{13}$C NMR (75 MHz, $CDCl_3$) δ: 154.5; 149.7; 144.9; 143.5; 137.5; 134.0; 130.1; 129.9; 126.7; 125.6; 123.0; 118.2; 113.6; 111.0; 110.9; 110.7; 55.7; 43.8.

Characterisation HRMS $C_{18}H_{17}N_4O$: 305.1402 (calculated); 305.1399 (observed).

Characterisation IR neat $v_{max}/cm^{-1}$: 3475, 3377, 2960, 2837, 2236, 1570, 1502, 1264.

Characterisation (liquid chromatography/mass spectrometry) LC-MS: t.r. 15.36.

Purity: 95.47%.

Example 2: Preparation of 4-(3-iodo-4-methoxyphenyl)(methyl)amino) quinoline-2-carbonitrile 2.1 Preparation of 4-(3-iodo-4-methoxyphenyl)amino)quinoline-2-carbonitrile

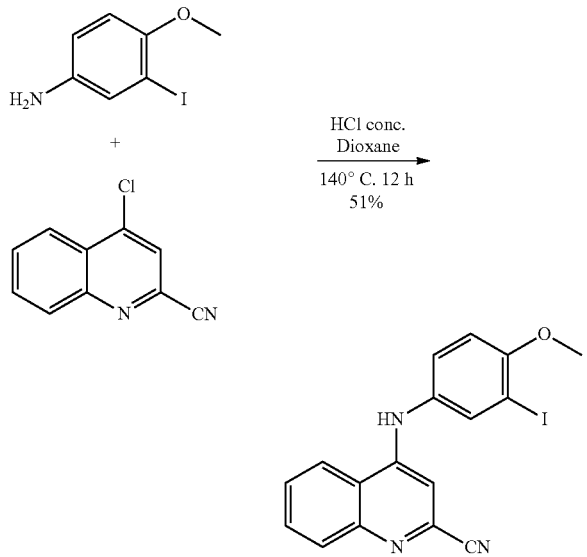

In a sealed tube the following are mixed: 4-chloroquinoline-2-carbonitrile (376 mg, 2.00 mmol, 1 equivalent), and 3-iodo-4-methoxyaniline (500 mg, 2.00 mmol), dioxane (10 mL) and concentrated HCl (5 drops).

The mixture is heated overnight at 140° C.

After the reaction medium has cooled, the mixture is neutralised to neutral pH and extracted with ethyl acetate. The organic phases are dried over MgSO₄.

The crude residue is purified by means of chromatography on silica gel (cyclohexane:ethyl acetate 0→30%)

The 4-(3-iodo-4-methoxyphenyl)amino)quinoline-2-carbonitrile is isolated in the form of a yellow solid with a yield of 51%.

Characterisation ¹H NMR (300 MHz, CDCl₃) δ: 8.11 (d, J=8.5 Hz, 1H); 7.92 (d, J=7.7 Hz, 1H); 7.86-7.74 (m, 2H); 7.71-7.60 (m, 1H); 7.33 (dd, J=8.3; 2.7 Hz, 1H); 7.00-6.88 (m, 2H); 6.73 (s, 1H); 3.98 (s, 3H).

Characterisation Electrospray Ionisation-High Resolution Mass Spectrometry (ESI⁺) HRMS: m/z for C₁₇H₁₃N₃OI [M+H]⁺ 402.0103 (calculated); 402.0113 (found).

2.2 Preparation of 4-((3-iodo-4-methoxyphenyl)(methyl)amino)quinoline-2-carbonitrile

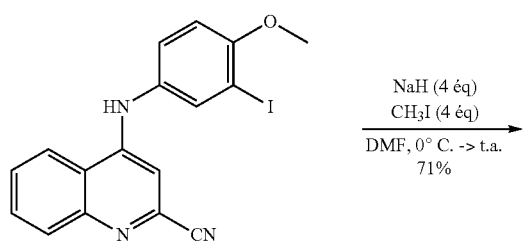

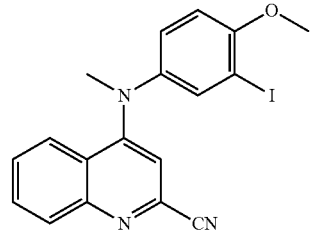

NaH (70.0 mg, 2.17 mmol) is added to a solution of 4-((3-iodo-4-methoxyphenyl)amino)quinoline-2-carbonitrile (219 mg, 0.54 mmol) in Dimethylformamide (DMF) (5 mL) at 0° C. CH₃I (305 mg, 2.17 mmol) is then added drop by drop. The mixture is agitated for a period of 30 minutes at 0° C.

The mixture is brought to ambient temperature, diluted with water and then extracted with ethyl acetate and dried over MgSO₄.

The crude residue is purified by means of chromatography on silica gel (cyclohexane:ethyl acetate 0→40%)

The compound 4-((3-iodo-4-methoxyphenyl)(methyl)amino)quinoline-2-carbonitrile is isolated in the form of a yellow solid with a yield of 71%.

Characterisation ¹H NMR (300 MHz, CDCl₃) δ: 8.08 (d, J=8.4 Hz, 1H); 7.79-7.51 (m, 3H); 7.48-7.21 (m, 2H); 6.92 (dd, J=8.7; 2.7 Hz, 1H); 6.73 (d, J=8.8 Hz, 1H); 3.88 (s, 3H); 3.48 (s, 3H).

Characterisation ¹³C NMR (75 MHz, CDCl₃) δ: 155.49; 154.17; 149.84; 144.02; 134.25; 134.19; 130.56; 130.29; 127.41; 125.07; 124.27; 123.06; 117.91; 112.35; 111.28; 86.64; 56.66; 43.64.

Characterisation (ESI⁺) HRMS: m/z C₁₈H₁₅N₃OI [M+H]⁺ 416.02 260 (calculated); 416.0267 (found).

Characterisation IR (neat): 1571, 1562, 1482, 1430, 1279, 1109, 808, 766, 713, 603 cm⁻¹.

Melting point=175-180° C.

Example 3: Preparation of (E)-5-(5-((2-cyanoquinolin-4-yl)(methyl) amino)-2-methoxyphenyl)-N-hydroxypent-4-enamide 3.1 Preparation of N-((tetrahydro-2H-pyran-2-yl)oxy)pent-4-enamide

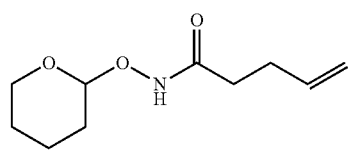

One equivalent of carboxylic acid is mixed with one equivalent of NHTHP in Dichloromethane (DCM). One equivalent of (Dicyclohexylcarbodiimide) DCC is subsequently added. The mixture is agitated overnight at ambient temperature and then washed with a saturated bicarbonate solution and water. The residue is purified by means of chromatography on silica gel (cyclohexane:ethyl acetate 1:1).

N-((tetrahydro-2H-pyran-2-yl)oxy)pent-4-enamide in the form of a white solid is obtained with a yield of 86%.

Characterisation ¹H NMR (300 MHz, DMSO) δ: 10.93 (s, 1H); 5.78 (dq, J=10.6; 6.6 Hz, 1H); 5.00 (dd, J=21.1; 13.7

Hz, 2H); 4.80 (s, 1H); 3.92 (m, 1H); 3.50 (m, 1H); 2.24 (m, 2H); 2.08 (m, 2H); 1.69-1.51 (m, 6H).

3.2 Preparation of (E)-5-(5-((2-cyanoquinolin-4-yl)(methyl)amino)-2-methoxyphenyl)-N-hydroxypent-4-enamide

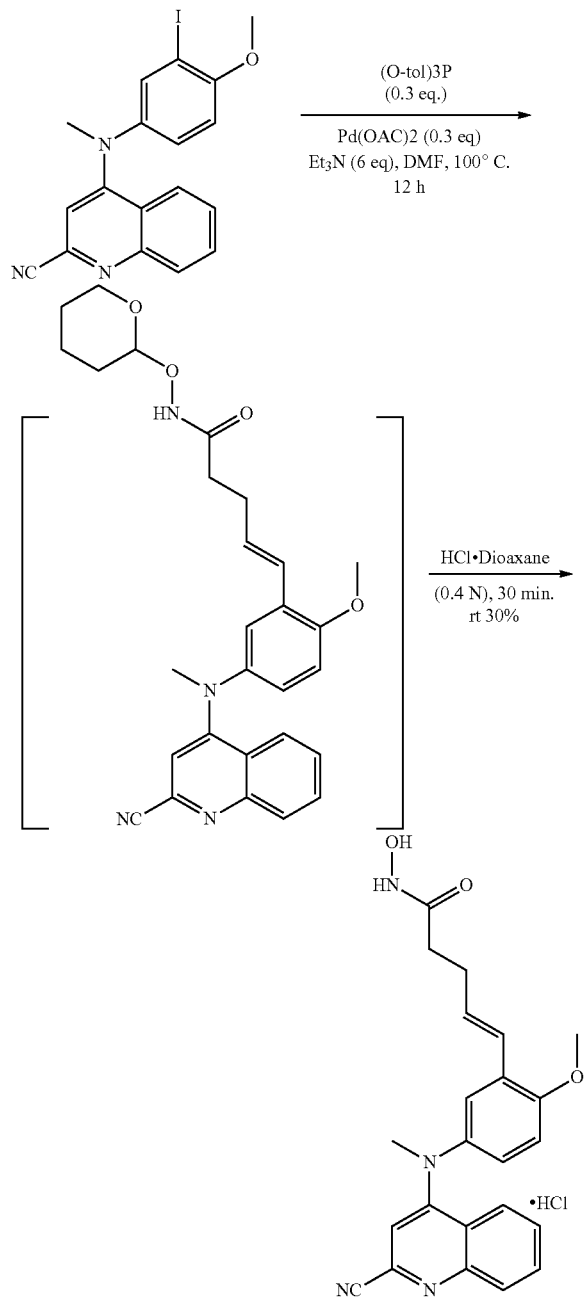

In a sealed tube purged with argon gas, the following are added: 4-((3-iodo-4-methoxyphenyl)(methyl)amino)quinoline-2-carbonitrile as prepared in Example 2 above (30.0 mg, 0.072 mmol), N-((tetrahydro-2H-pyran-2-yl)oxy)pent-4-enamide (42.0 mg, 0.20 mmol), tri(o-tolyl)phosphine (7.20 mg, 0.023 mmol), Pd(OAC)$_2$ (6.0 mg, 0.026 mmol), EtN$_3$ (49.0 mg, 0.48 mmol) and DMF (1 mL); the mixture is degassed and heated overnight at 100° C.

The reaction medium is brought to ambient temperature, diluted with DCM and thereafter filtered through celite, the filtrate is then evaporated. The formation of the intermediate compound (see schematic above) is confirmed by Liquid Chromatography/Mass Spectrometry (LC/MS), and the compound is used in the subsequent step without purification.

A solution of 4N HCl in dioxane (0.5 mL) is added to a solution of the intermediate compound (see schematic above) in anhydrous dioxane (1 mL). The mixture is agitated for a period of 30 minutes at ambient temperature and subsequently evaporated at ambient temperature and then purified by high performance liquid chromatography (HPLC) using a gradient of acetonitrile in water. After lyophilisation, the compound (E)-5-(5-((2-cyanoquinolin-4-yl)(methyl)amino)-2-methoxyphenyl)-N-hydroxypent-4-enamide is obtained in the form of a yellow solid with a yield of 30%.

Characterisation (ESI$^+$) HRMS: m/z C$_{23}$H$_{23}$N$_4$O$_3$ [M+H]$^+$: 403.1770 (calculated); 403.1768 (found).

Characterisation IR (neat): 2947, 1641, 1569, 1491, 1235, 1031, 970, 758 cm$^{-1}$.

Purity (HPLC): 100%.

Characterisation $^1$H NMR (400 MHz, MeOD) δ: 7.89 (d, J=8.3 Hz, 1H); 7.61 (t, J=7.4 Hz, 1H); 7.53-4.45 (m, 1H); 7.34 (m, 1H); 7.24-7.23 (m, 3H); 6.87 (m, 3H); 6.67 (d, J=15.9 Hz, 1H); 6.17-6.04 (m, 1H); 3.81 (s, 3H); 3.48 (s, 4H); 2.46 (dd, J=13.5; 6.7 Hz, 2H); 2.28-2.16 (m, 2H).

Characterisation $^{13}$C NMR (101 MHz, MeOD) δ: 172.04; 156.07; 155.65; 150.60; 144.35; 134.94; 131.31; 131.22; 130.31; 129.22; 127.66; 126.91; 126.25; 125.32; 123.70; 123.63; 118.85; 113.20; 111.66; 56.24; 44.45; 33.52; 30.33.

Melting point=177-182° C.

Example 4: Preparation of 5-(5-((2-cyanoquinolin-4-yl)(methyl)amino)-2-methoxyphenyl)-N-hydroxypent-4-ynamide 4.1 Preparation of N-((tetrahydro-2H-pyran-2-yl)oxy)pent-4-ynamide

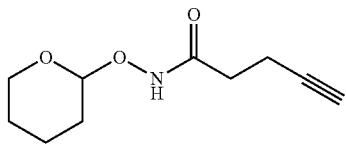

One equivalent of carboxylic acid is mixed with one equivalent of NHTHP in DCM. One equivalent of (Dicyclohexylcarbodiimide) DCC is subsequently added. The mixture is agitated overnight at ambient temperature and then washed with a saturated bicarbonate solution and water. The residue is purified by means of chromatography on silica gel (cyclohexane:ethyl acetate 1:1).

The N-((tetrahydro-2H-pyran-2-yl)oxy)pent-4-ynamide in the form of a white solid is obtained with a yield of 76%.

Characterisation $^1$H RMN (300 MHz, DMSO) δ: 11.04 (s, 1H); 4.80 (s, 1H); 3.91 (s, 1H); 3.50 (d, J=11.6 Hz, 1H); 2.80 (s, 1H); 2.35 (d, J=6.2 Hz, 2H); 2.18 (t, J=7.0 Hz, 2H); 1.58 (m, 6H).

4.2 Preparation of 5-(5-((2-cyanoquinolin-4-yl)(methyl)amino)-2-methoxyphenyl)-N-hydroxypent-4-ynamide

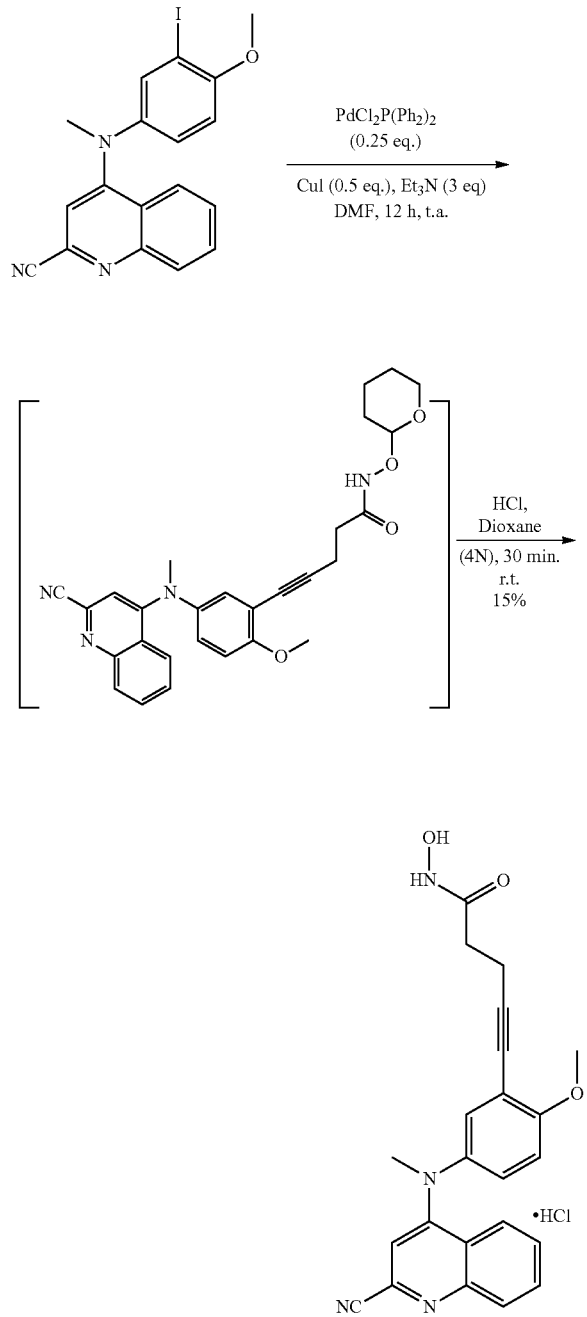

In a sealed tube purged with argon, the following are added: 4-((3-iodo-4-methoxyphenyl)(methyl)amino)quinoline-2-carbonitrile as prepared in Example 2 above (30.0 mg, 0.072 mmol), N-((tetrahydro-2H-pyran-2-yl)oxy)pent-4-ynamide (28.0 mg, 0.144 mmol), PdCl$_2$P(Ph$_3$)$_2$ (12 mg, 0.017 mmol), CuI (7 mg, 0.036 mmol), Et$_3$N (21.0 mg, 0.22 mmol) and DMF (1 mL).

The mixture is degassed and agitated overnight at ambient temperature. The reaction mixture is diluted with DCM and thereafter filtered through celite, the filtrate is then evaporated. The formation of the intermediate compound (see scheme above) is confirmed by Liquid Chromatography/Mass Spectrometry (LC/MS), and the compound is used in the subsequent step without purification.

A solution of 4N HCl in dioxane (0.5 mL) is added to a solution of the intermediate compound (see schematic above) (29.0 mg, 0.06 mmol) in anhydrous dioxane (1 mL). The mixture is agitated for a period of 30 minutes at ambient temperature and subsequently evaporated at ambient temperature and then purified by high performance liquid chromatography (HPLC) using a gradient of acetonitrile in water.

After lyophilisation, the compound 5-(5-((2-cyanoquinolin-4-yl)(methyl)amino)-2-methoxyphenyl)-N-hydroxypent-4-ynamide is obtained in the form of a yellow solid with a yield of 15%.

Characterisation $^1$H NMR (400 MHz, MeOD) δ: 8.54 (s, 1H); 7.93 (d, J=8.3 Hz, 1H); 7.72-7.49 (m, 2H); 7.30-7.27 (m, 2H); 7.18-6.85 (m, 3H); 3.83 (s, 3H); 3.47 (s, 3H); 2.70 (s, 2H); 2.34 (s, 2H).

Characterisation $^{13}$C NMR (101 MHz, DMSO) δ: 167.20; 156.84; 153.86; 149.09; 142.69; 133.65; 130.27; 129.92; 128.30; 127.21; 125.14; 125.05; 122.31; 118.06; 113.16; 112.43; 112.11; 94.05; 76.58; 55.84; 43.65; 40.15; 39.94; 39.73; 39.52; 39.31; 39.10; 38.89; 31.49; 15.41.

Characterisation (ESI$^+$) HRMS: m/z C$_{23}$H$_{21}$N$_4$O$_3$ [M+H]$^+$ 403.1614 (calculated); 403.1621 (found).

Characterisation IR (neat): 2987, 1644, 1496, 1066, 766 cm$^{-1}$.

Purity (HPLC): 100%.

Melting point=170-175° C.

Example 5: Preparation of (E)-3-(5-((2-cyanoquinolin-4-yl)(methyl) amino)-2-methoxyphenyl)-N-hydroxyacrylamide

5.1 Preparation of N-((tetrahydro-2H-pyran-2-yl)oxy)acrylamide

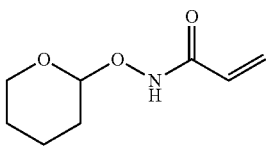

One equivalent of carboxylic acid is mixed with one equivalent of NHTHP in DCM. One equivalent of (Dicyclohexylcarbodiimide) DCC is subsequently added. The mixture is agitated overnight at ambient temperature and then washed with a saturated bicarbonate solution and water. The residue is purified by chromatography on silica gel (cyclohexane:ethyl acetate 1:1).

The N-((tetrahydro-2H-pyran-2-yl)oxy)acrylamide is obtained in the form of a white solid with a yield of 61%.

Characterisation $^1$H NMR (200 MHz, CDCL) δ: 9.41 (s, 1H); 6.40 (d, J=16.7 Hz, 1H); 6.15 (s, 1H); 5.69 (d, J=10.4 Hz, 1H); 4.97 (s, 1H); 3.96 (t, J=8.1 Hz, 1H); 3.59 (dd, J=11.3; 4.0 Hz, 1H); 1.77 (d, J=10.9 Hz, 3H); 1.58 (s, 3H).

5.2 Preparation of (E)-3-(5-((2-cyanoquinolin-4-yl)(methyl)amino)-2-methoxyphenyl)-N-hydroxyacrylamide

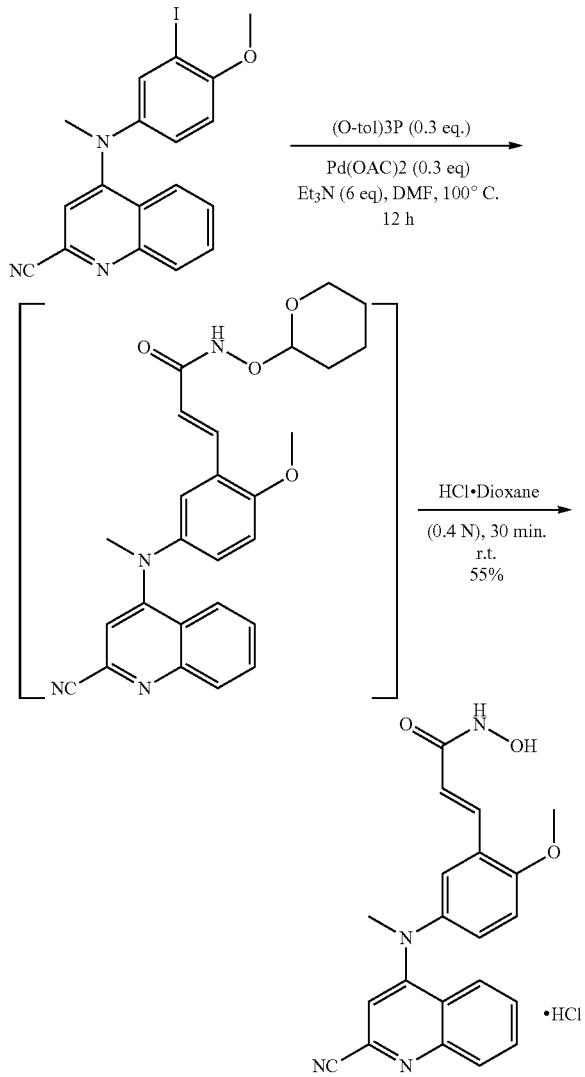

In a sealed tube purged with argon, the following are added: 4-((3-iodo-4-methoxyphenyl)(methyl)amino)quinoline-2-carbonitrile as prepared in Example 2 above (30.0 mg, 0.072 mmol), N-((tetrahydro-2H-pyran-2-yl)oxy)acrylamide (34.0 mg, 0.20 mmol), tri(o-tolyl)phosphine (7.20 mg, 0.023 mmol), Pd(OAC)$_2$ (6.0 mg, 0.026 mmol), EtN$_3$ (49.0 mg, 0.48 mmol) and DMF (1 mL). The mixture is degassed and heated overnight at 100° C.

The reaction medium is brought to ambient temperature, diluted with DCM and thereafter filtered through celite, the filtrate is then evaporated. The formation of the intermediate compound (see schematic above) is confirmed by Liquid Chromatography/Mass Spectrometry (LC/MS), and the compound is used in the subsequent step without purification A solution of 4N HCl in dioxane (0.5 mL) is added to a solution of the intermediate compound (see schematic above) in anhydrous dioxane (1 mL). The mixture is agitated for a period of 30 minutes at ambient temperature and subsequently evaporated at ambient temperature and then purified by high performance liquid chromatography (HPLC) using a gradient of acetonitrile in water.

After lyophilisation, the compound (E)-3-(5-((2-cyanoquinolin-4-yl)(methyl) amino)-2-methoxyphenyl)-N-hydroxyacrylamide is obtained in the form of a yellow solid with a yield of 55%.

Characterisation $^1$H NMR (300 MHz, MeOD) δ: 7.94 (d, J=8.2 Hz, 1H); 7.82-7.48 (m, 3H); 7.44 (s, 1H); 7.29 (s, 2H); 7.07 (dd, J=29.0; 8.9 Hz, 2H); 6.42 (d, J=17.0 Hz, 1H); 4.85 (peak corresponding to hydrochloride salt overlapped with water), 3.90 (s, 3H); 3.53 (s, 3H).

Characterisation $^{13}$C NMR (75 MHz, MeOD) δ: 165.03; 155.74; 154.66; 149.31; 143.14; 134.58; 133.72; 130.06; 129.10; 126.58; 125.39; 124.73; 123.80; 122.40; 118.50; 117.41; 112.46; 110.98; 55.02; 42.86. Characterisation (ESI$^+$) HRMS: m/z C$_{21}$H$_{19}$N$_4$O$_3$ [M+H]$^+$ 375.1457 (calculated); 375.1455 (found).

Characterisation IR (neat): 3213, 1567, 1492, 1427, 1241, 1105, 977, 762 cm$^{-1}$.

Purity (HPLC): 100%.

Melting point=215-210° C.

Example 6: Comparison of the Antiproliferative Activity of Compounds of the Invention (Referenced as "ICQN") in Free, Unconjugated Format on Cancer Cell Lines The IC$_{50}$ (as per accepted terminology) activities of the compounds according to the invention 4-((3-amino-4-methoxyphenyl)(methyl)amino) quinoline-2-carbonitrile (ICQN-1); 5-(5-((2-cyanoquinolin-4-yl)(methyl)amino)-2-methoxyphenyl)-N-hydroxypent-4-ynamide (ICQN-2); and (E)-3-(5-((2-cyanoquinolin-4-yl)(methyl)amino)-2-methoxyphenyl)-N-hydroxyacrylamide (ICQN-3) were compared with compounds of the prior art and with a commercial and clinical reference compound, in particular MMAE (monomethylauristatin E). The IC$_{50}$ activities were measured on various different cancer cell lines HCT116 (colorectal tumour), A549 (non-small cell lung cancer), NCI-N87 (gastric tumour), Mia-Paca-2 (pancreatic tumour), K562R (chronic myeloid leukemia), SKOV3 (ovarian tumour), SKBr3 (breast tumour, Her2 overexpression), MCF7 (breast tumour) and MDA-MB231 (breast tumour).

The cancer cell lines were obtained from the American Culture Collection (ATCC, Rockville, MD) or from the German collection of microorganisms and cell cultures of the Leibniz Institute (DSMZ, Braunschweig-Germany) or from the European collection of cell cultures (ECACC, England). The cancer cell lines were cultured according to the supplier's instructions.

The HCT-116 human colorectal carcinoma, SK-BR3 breast carcinoma, and SK-OV-3 ovarian carcinoma cells were cultured in Gibco McCoy's 5A medium supplemented with 10% foetal calf serum (FCS) and 1% glutamine.

The A549 lung carcinoma cells, K562R myeloid leukemia cells, and the NCI-N87 gastric carcinoma cells were cultured in Gibco Roswell Park Memorial Institute (RPMI) 1640 medium supplemented with 10% foetal calf serum (FCS) and 1% glutamine. The Mia-Paca2 carcinoma cells were cultured in Gibco Dulbecco's Modified Eagle Medium (DMEM) supplemented with 10% foetal calf serum (FCS) and 1% glutamine.

The breast adenocarcinoma cells MDA-MB231 and MCF7 were cultured in Gibco RPMI 1640 culture medium supplemented with 10% foetal calf serum (FCS) and 1% glutamine.

The cells were counted using a Vi-cell XR (Beckman Coulter) and the cell viability was assessed by using 0.25% trypan blue dye exclusion assay. The cells were tested for the presence of mycoplasmas prior to the experiments with the Mycoplasma PCR detection kit (Applied Biological Materials Inc., Canada) according to the manufacturer's instructions, and only mycoplasma-free cells were used for the study. The cell lines were maintained at 37° C. in a humidified atmosphere containing 5% $CO_2$.

For the determination of $IC_{50}$, the cells were seeded in 96-well plates ($3 \times 10^3$ cells/well) containing 100 µl of growth medium. After 24 hours of culturing, the cells were treated with the tested compounds at 10 different final concentrations. Each concentration was obtained from serial dilutions in culture medium starting from the stock solution. The control cells were treated with the carrier. The experiments were carried out in triplicate.

The measurements were performed after 72 hours of treatment using the CellTiter Glo assay (Promega) which makes it possible to measure through bioluminescence (quantification of adenosine triphosphate—ATP) the number of living cells, by using a PolarStar Omega microplate reader (BMG-Labtech).

The dose-response curves were plotted with the Graph Prism software application and the $IC_{50}$ values were calculated using the Graph Prism software based on polynomial curves (four or five parameter logistic equations).

The results are shown in Table 1 below.

As these results show, the compounds according to the invention exhibit very good inhibitory activity against a number of cancer cell lines.

TABLE 1

| Cell Lines | HCT116 $IC_{50}$ (nM) | A549 $IC_{50}$ (nM) | NIC-N87 $IC_{50}$ (nM) | Mia-Paca-2 $IC_{50}$ (nM) | K562R $IC_{50}$ (nM) | SKOV3 $IC_{50}$ (nM) | SKBr3 $IC_{50}$ (nM) | MCF7 $CI_{50}$ (nM) | MDA-MB231 $CI_{50}$ (nM) |
|---|---|---|---|---|---|---|---|---|---|
| 4-((3-amino-4-methoxyphenyl)(methyl)amino)quinoline-2-carbonitrile ICQN-1 | 0.23 | 0.72 | 0.30 | 0.49 | 0.47 | 0.44 | 0.36 | 0.17 | 0.34 |
| MMAE (GOLD STANDARD) | 1.52 | 4.12 | 6.58 | 3.02 | 19.70 | 0.08 | 0.06 | 0.58 | 1.25 |
| 4-((3-amino-4-ethoxyphenyl)(methyl)amino)quinoline-2-carbonitrile ICQN-2 | / | / | 0.93 | 0.29 | 0.36 | 0.59 | 0.38 | / | / |
| (E)-3-(5-((2-cyanoquinolin-4-yl)(methyl)amino)-2-methoxyphenyl)-N-hydroxyacrylamide ICQN-3 | / | / | 0.10 | 0.94 | 0.56 | 2.64 | 1.78 | 0.78 | 0.44 |

The results of $IC_{50}$ over the cell lines HCT116, A549, NCI-N87, Mia-Paca-2, K562R, MCF7 and MDA-MB231 are overall far better than those obtained with the commercial and clinical reference compound MMAE. It should be reiterated that the selection of cell lines is based on a broad spectrum of solid and liquid cancer indications representing a medical need that remains unmet in which context the conjugated antibodies would be relevant. This cytotoxicity observed over a broad panel is also a criterion of commercial success for payloads.

Example 7: Comparative Analysis of the Antiproliferative Activity of the Compounds of the Invention with the Commercial and Clinical Reference Compound MMAE (in Unconjugated Format)

The $IC_{50}$ ratio was established between a compound of the invention (ICQN-1) and MMAE. The higher the $IC_{50}$ ratio, the greater the potential for therapeutic improvement and thus greater the potential for commercial success.

TABLE 2

| Cell Lines | HCT116 | A549 | NCI-N87 | Mia-Paca-2 | MCF7 | MDA-MB231 |
|---|---|---|---|---|---|---|
| $IC_{50}$ Ratio ICQN1/MMAE | 7 | 6 | 22 | 6 | 3 | 4 |

Thus, the compounds according to the invention demonstrate a very significant advantage over MMAE. For example, in the context of the NCI-N87 (gastric cancer) cell line, ICQN1 is 22 times more efficacious than MMAE.

Example 8: Antiproliferative Activity as Compared to the Compounds of the Prior Art Having a Quinoline Nucleus and an Aromatic Ring Linked to Each Other by an N-Me Group (L. Chen et al. Eur. J. Med. Chem. 2017, 138, 1114)

In the context of the work published by Chen et al. cited above, among the molecules mentioned, the compound 13b has the following structure:

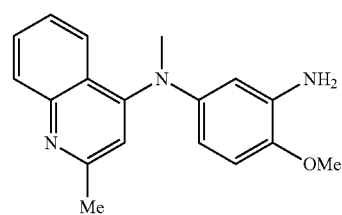

13b $IC_{50}$(MDA-MB-231) = 3.2 nM

This compound 13b shows an $IC_{50}$ of 3.2 nM over the MDA-MB-231 cell line.

Table 3 below presents the collective comparative data over 7 cell lines for a compound according to the invention (ICQN-1 (4-((3-amino-4-methoxyphenyl)(methyl)amino) quinoline-2-carbonitrile)) and for the compound 13b described by L. Chen et al. (Eur. J. Med. Chem. 2017, 138, 1114)

TABLE 3

|  | HCT116 | A549 | NCI-N87 | Mia-Paca2 | K562R | SKOV3 | SKBr3 |
|---|---|---|---|---|---|---|---|
| Prior Art Compound 13b according to L. Chen et al. | 2.15 | 0.68 | 4.36 | 0.92 | 3.59 | 1.28 | 2.17 |
| Compound according to the invention (Compound ICQN1) | 0.23 | 0.72 | 0.30 | 0.49 | 0.47 | 0.44 | 0.36 |
| Ratio of activity 13b vs ICQN-1 | ~10 | 1 | 15 | 2 | 8 | 3 | 6 |

The compounds of the invention, quite surprisingly, have an overall cytotoxic activity that is far greater than that of the compound 13b. The resulting activity obtained following the replacement of the Me group by CN at position 2 of the quinoline is unexpected and could not have been predicted by the person skilled in the art. In fact, according to L. Chen et al as well as the person skilled in the art, the methyl at position 2 of quinoline was considered to be necessary in order to maintain the inhibitory activity. Moreover, according to L. Chen et al, no mention is made of any conjugation or application in the context of an ADC strategy.

Example 9: Antiproliferative Activity as Compared to the Compounds of the Prior Art Having a Diheteroarylmethylamine Type Structure (Alami et al.)

According to Alami et al. *Eur. J. Med. Chem.* 2019, 168, 176-188, by comparison of the molecules Ia and Ib (structures here below), the person skilled in the art noted that replacing Me by CN at position 2 of quinoline led to a drastic drop in cytotoxic activity (by a factor of 170 over the HCT116 cell line).

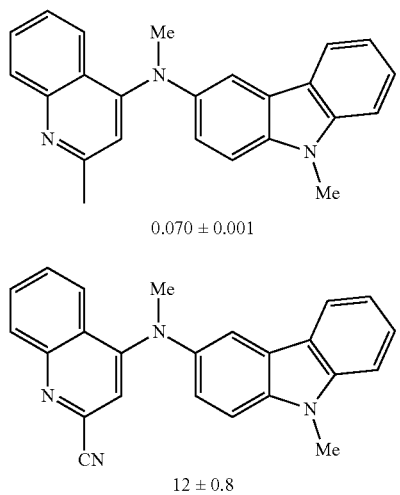

However, as supported by Example 8 here above, the replacement of an Me by CN at position 2 of quinoline induces a surprising improvement in cytotoxicity (by a factor of 10). The person skilled in the art did not expect and could not have foreseen such activity in respect of the compounds according to the present invention.

It should also be noted that the compound 1a according to Alami et al. could not possibly be considered as a payload in the context of an ADC strategy given that it does not have an anchor point for binding to a linker.

Example 10: Antiproliferative Activity as Compared to the Compounds of the Prior Art Having a Di(Heteroaryl)Arylethylene Type Structure According to Alami et al. *J. Med. Chem.* 2019, 62, 1902-1916, by comparing two at a time the molecules 4f/4j and 4g/4k that carry a double bond instead of the N-Me group, the person skilled in the art would have found that replacing Me with CN at position 2 of quinoline did not provide the ability to foresee achieving an improvement in the cytotoxic activity $IC_{50}$ below 1 nM for the cell line HCT116. The person skilled in the art noted a loss in activity when passing from the compound 4f (Me at position 2) to the compound 4j (CN at position 2).

Table 4, which appears in FIG. 1

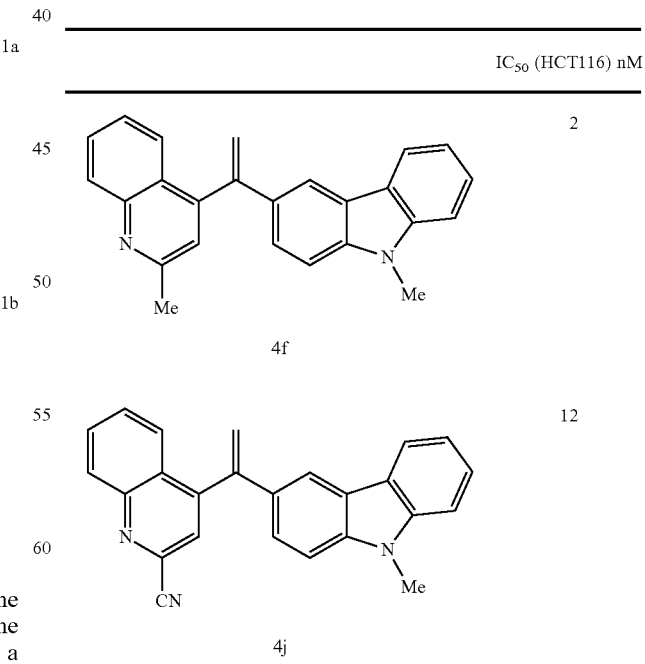

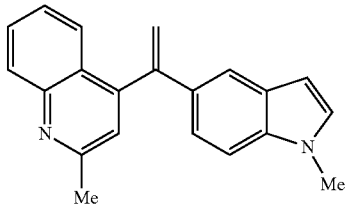

IC$_{50}$ (HCT116) nM: 5.7

4g

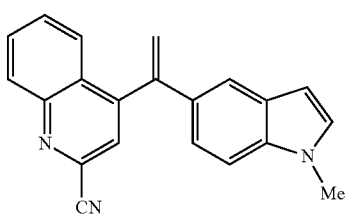

IC$_{50}$ (HCT116) nM: 3.4

4k

Example 11: Comparative Analysis of the Antiproliferative Activity of a Compound of the Invention as Compared to the Payload of the Prior Art ICQO-1

Of all the compounds identified in the prior art, ICQO-1 is the only one to exhibit the characteristic of a payload according to the person skilled in the art. ICQO is a compound disclosed in the international patent application PCT/EP2018/058168 as having the following structure:

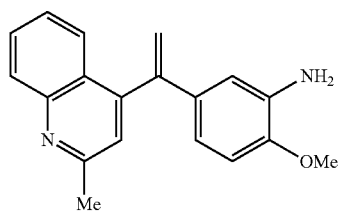 [SMILES: C=C(c1ccc(OC)c(N)c1)c1cc(C)nc2ccccc12]

The IC$_{50}$ ratio was established between a compound of the invention (ICQN-1) and the compound of the prior art ICQO-1. The higher the ratio, the greater the potential therapeutic activity in vivo.

TABLE 5

| Cell lines | HCT-116 | SKOV-3 |
| --- | --- | --- |
| ICQN-1 vs ICQO-1 | 44 | 3 |

The ratios indicate that the compounds of the invention (ICQN) demonstrate a very significant advantage over compounds of the ICQO-1 type. For example, in the context of the HCT-116 (colorectal cancer) cell line, ICQN-1 is 44 times more efficacious than the payload compound ICQO-1. This significant difference was particularly unforeseeable and unexpected for the person skilled in the art.

Example 12: Comparative Analysis of the Antiproliferative Activity of ICQN as Compared to Compounds of the Prior Art of the Quinoline Type (Patent Application US 2006/074187, Example 21)

VB118 is a quinoline compound (patent application US 2006/074187, Example 21) that has been synthesised and described with a view to being compared with the compounds according to the invention.

TABLE 6

| Cell Lines | ICQN2 | ICQN1 | VB118 |
| --- | --- | --- | --- |
| NCI-N87 | 0.93 | 0.30 | >100 nM |
| Mia-Paca-2 | 0.29 | 0.49 | >100 nM |
| K562R | 0.36 | 0.47 | >100 nM |
| SKOV-3 | 0.59 | 0.44 | >100 nM |
| SKBR3 | 0.38 | 0.36 | >100 nM |

The addition of the nitrile function and the amine function —NH2 at position 2 of quinoline on the compounds according to the invention (ICQN), compared with the compounds of the prior art of the VB118 type, induces a surprising increase, greater by at least 2 log of activity, over a broad panel of cell lines and cancer indications.

Example 13: Comparative Analysis of the Antiproliferative Activity of the Compounds of the Invention (ICQN) as Compared to the Commercial Reference Compound MMAE and the Payload ICQO-1 on Resistant Cancer Cells (MDR Profile: Multi Drug Resitance)

The K562R (chronic myeloid leukemia) cells have an MDR profile that allows them to be resistant to several chemotherapeutic compounds including the reference compound MMAE.

TABLE 7

| | K562R (PgP+) | Ratio vs MMAE | Ratio vs ICQO-1 |
| --- | --- | --- | --- |
| MMAE | 35 nM | | |
| ICQO-1 | 1.98 nM | 17 | |
| ICQN-1 | 0.47 nM | 74 | 4.2 |

The person skilled in the art within the payloads and conjugated medicinal products field would note that a payload such as MMAE with an IC$_{50}$ of 35 nM offers lower therapeutic interest than a compound according to the invention. A payload, in order to be efficacious once conjugated, preferably has sub-nanomolar activity on the targeted cancer line. It is found that the compound according to the invention ICQN-1 exhibits a superiority that is not only 74 times greater than the MMAE but also 4.2 times greater than the compound ICQO-1. The compounds according to the invention exhibit a particularly surprising activity while also exhibiting therapeutic differentiation for cancers that have a multi-drug resistance (MDR) profile.

Example 14: Preparation of Conjugated Antibodies

Figure 2B:
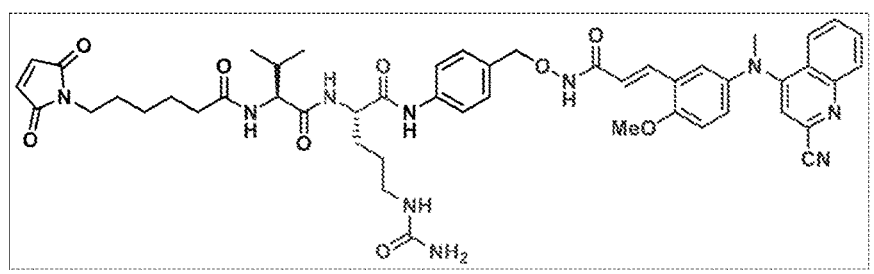
Figure 2B:
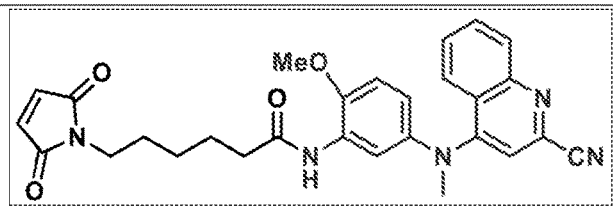
Figure 2B:
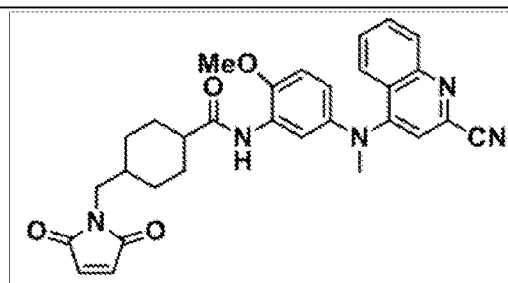

Various different "Toxic-Linker" compounds (based on valine-citrulin), enzyme cleavable (by Cathepsin B enzyme) and non-cleavable, were obtained as illustrated in table 8 below:

Table 8, which appears in FIGS. 2A and 2B

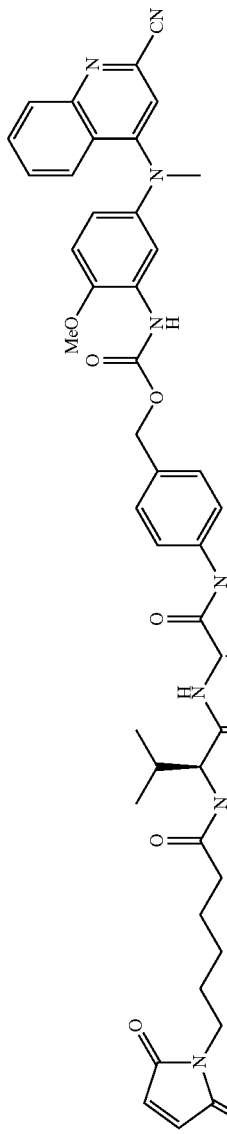
Mal-Val-Cit-
PABC-ICQN-1
(cleavable) (VB179)
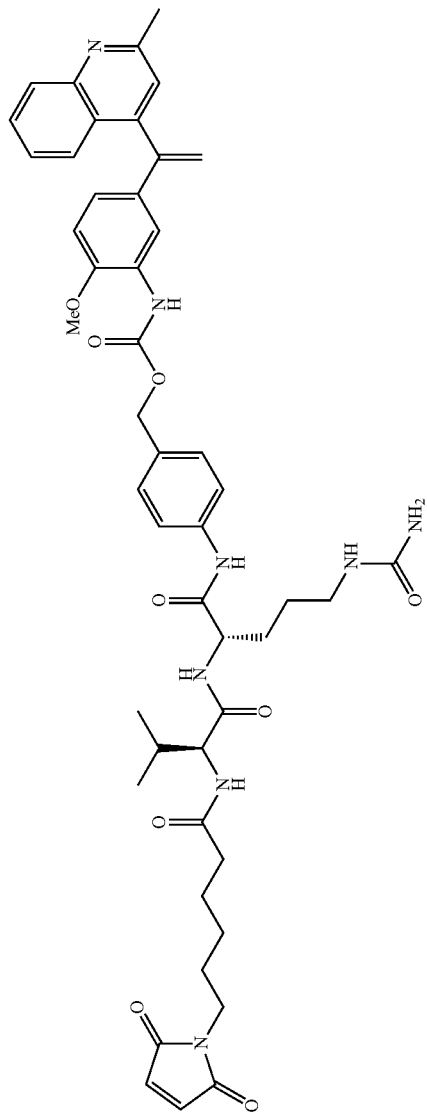
Mal-Val-Cit-
PABC-ICQO-1
(VB185)

-continued
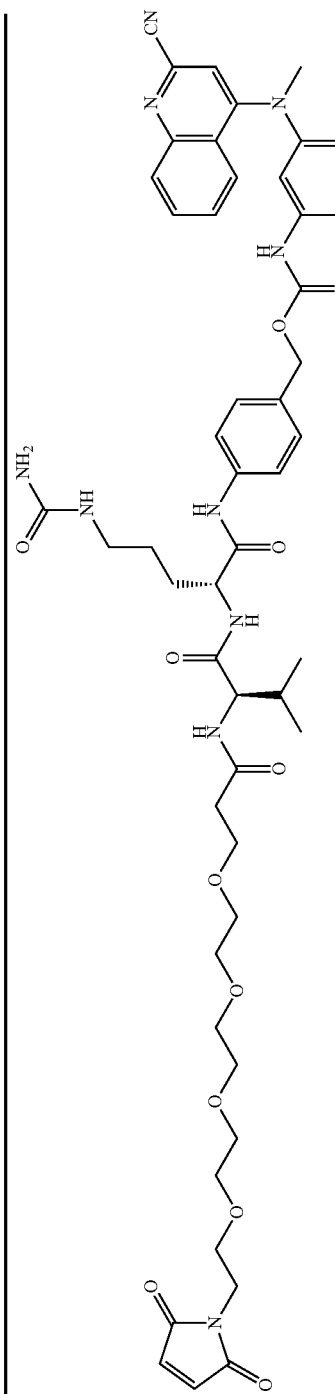
Mal-PEG4-Val-Cit-PABC-ICQN-1 (VB199)
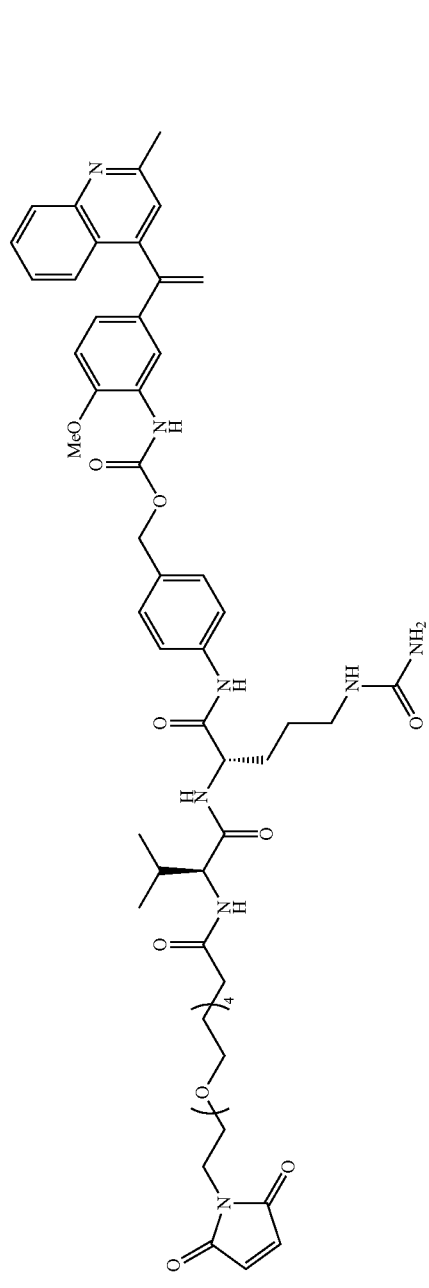
Mal-PEG4-Val-Cit-PABC-ICQO-1 (VB279 & VB288)

-continued
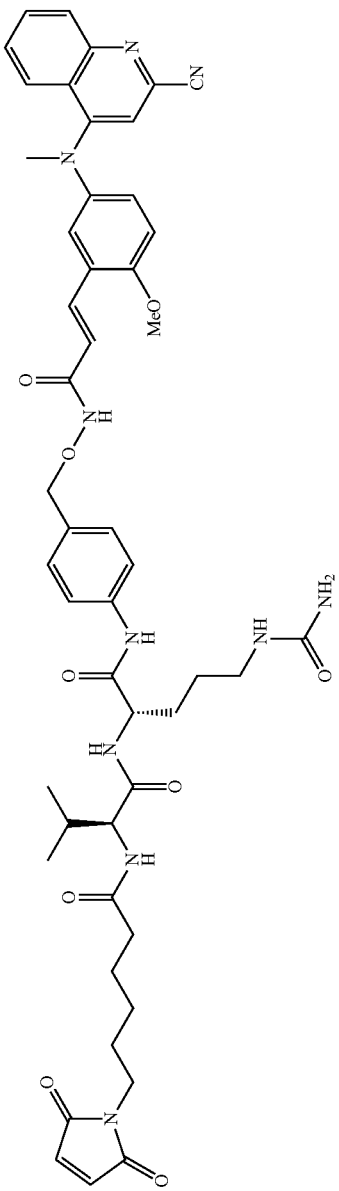
Mal-Val-Cit-PABC-NI313 (VB277)
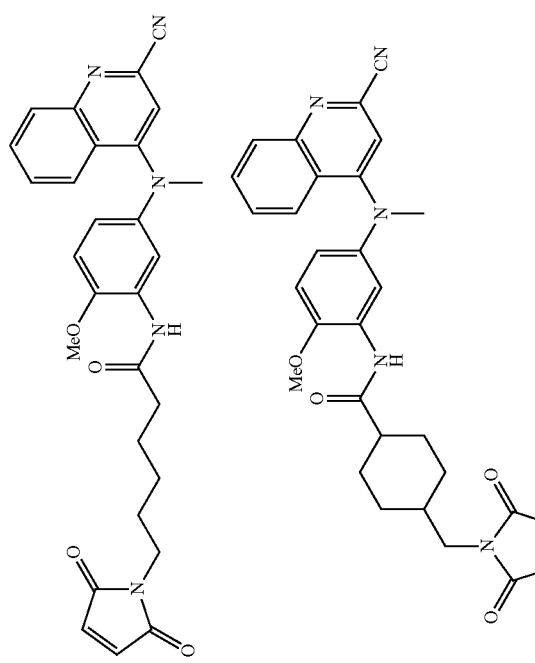
Mal-ICQN-1 (non cleavable) (VB284)
MCC-ICQN-1 (non cleavable) (VB289)

The compounds VB179, VB185, VB199 and VB279 were obtained by activation of the NH2 function of the compounds having the formula (I) according to the invention (ICQN-1) by para-nitrophenyl chloroformate. The intermediary formed then reacts with the benzyl alcohol function of the linker MC-Val-Cit-PABA.

The compound VB277 was prepared by activation of the benzyl alcohol function of the linker MC-Val-Cit-PABA in triflate form and followed by reacting in basic medium with the compound NI313.

The compounds VB284 and VB289 were prepared by peptide coupling between ICQN-1 and an acid function.

VB179:
$^1$H NMR (400 MHz, DMSO-d$_6$) δ:8.58 (s, 1H), 8.06 (d, J=7.3 Hz, 1H), 7.96 (d, J=7.8 Hz, 1H), 7.79 (d, J=8.4 Hz, 1H), 7.67 (t, J=7.6 Hz, 1H), 7.60 (s, 1H), 7.58 (s, 2H), 7.56 (s, 1H), 7.49 (dd, J=8.6, 1.1 Hz, 1H), 7.34 (m, 1H), 7.31 (s, 1H), 6.98 (s, 2H), 6.94 (d, J=8.8 Hz, 1H), 6.74 (dd, J=8.7, 2.7 Hz, 1H), 5.97 (t, J=5.8 Hz, 1H), 5.40 (s, 2H), 5.00 (s, 2H), 4.38 (td, J=8.2, 5.5 Hz, 1H), 4.18 (dd, J=8.3, 7.1 Hz, 1H), 3.77 (s, 3H), 3.43 (s, 3H), 2.97 (m, 2H), 2.15 (m, 2H), 1.97 (dq, J=13.5, 6.7 Hz, 1H), 1.70 (m, 1H), 1.57 (m, 1H), 1.52-1.47 (m, 2H), 1.45 (d, J=7.3 Hz, 2H), 1.42-1.30 (m, 2H), 1.23-1.14 (m, 2H), 0.85 (d, J=6.7 Hz, 3H), 0.82 (d, J=6.7 Hz, 3H). HRMS (ESI): m/z [M+H] calcd. for $C_{47}H_{55}N_{10}O_9$: 903,4153 Found: 903,4156. Purity: 98.2%

VB 199:
$^1$H NMR (400 MHz, DMSO-d$_6$) δ:8.58 (s, 1H), 8.06 (d, J=7.3 Hz, 1H), 7.96 (d, J=7.8 Hz, 1H), 7.79 (d, J=8.4 Hz, 1H), 7.67 (t, J=7.6 Hz, 1H), 7.60 (s, 1H), 7.58 (s, 2H), 7.56 (s, 1H), 7.49 (dd, J=8.6, 1.1 Hz, 1H), 7.34 (m, 1H), 7.31 (s, 1H), 6.98 (s, 2H), 6.94 (d, J=8.8 Hz, 1H), 6.74 (dd, J=8.7, 2.7 Hz, 1H), 5.97 (t, J=5.8 Hz, 1H), 5.40 (s, 2H), 5.00 (s, 2H), 4.38 (td, J=8.2, 5.5 Hz, 1H), 4.18 (dd, J=8.3, 7.1 Hz, 1H), 3.77 (s, 3H), 3.62-3.47 (m, 10 2H), 3.43 (s, 3H), 2.97 (m, 2H), 1.97 (dq, J=13.5, 6.7 Hz, 1H), 1.70 (m, 1H), 1.57 (m, 1H), 1.42-1.30 (m, 2H), 0.85 (d, J=6.7 Hz, 3H), 0.82 (d, J=6.7 Hz, 3H). HRMS (ESI): m/z [M+H] calcd. for $C_{52}H_{65}N_{10}O_{13}$: 1037.4733 Found: 1037.4727. Purity: 96.0%

VB277
HRMS (ESI): m/z [M+H] calcd. for $C_{49}H_{57}N_{10}O_9$: 929.4310 Found: 929.4312.

VB284
$^1$H NMR (300 MHz, CDCl$_3$) δ:8.48 (d, J=1.9 Hz, 1H), 8.04 (d, J=9.1 Hz, 1H), 7.83 (s, 1H), 7.73-7.55 (m, 2H), 7.21 (s, 1H), 6.74 (d, J=8.7 Hz, 1H), 6.71 (s, 2H), 6.53 (d, J=9.6 Hz, 1H), 3.90 (s, 2H), 3.57 (m, 2H), 3.53 (s, 3H), 2.43 (t, J=7.3 Hz, 2H), 1.76 (m, 4H), 1.42 (m, 2H). HRMS (ESI): m/z [M+H] calcd. for $C_{28}H_{28}N_5O_4$: 498.2141 Found: 498.2140. Purity: 100%

VB289 $^1$H NMR (300 MHz, CDCl$_3$) δ:8.46 (d, J=2.3 Hz, 1H), 8.02 (d, J=8.8 Hz, 1H), 7.86 (s, 1H), 7.70-7.54 (m, 2H), 7.34-7.23 (m, 1H), 7.18 (s, 1H), 6.71 (s, 2H), 6.45 (dd, J=8.6, 2.5 Hz, 1H), 3.87 (s, 3H), 3.46 (s, 3H), 3.40 (d, J=6.6 Hz, 2H), 2.30-2.16 (m, 1H), 2.10-1.97 (m, 2H), 1.87-1.76 (m, 2H), 1.54 (ddd, J=25.0, 13.1, 3.0 Hz, 2H), 1.16-0.98 (m, 2H), 0.88 (m, 1H). HRMS (ESI): m/z [M+H] calcd. for 524.2298 $C_{30}H_{30}N_5O_4$: Found: 524.2300. Purity: 93%

The conjugated antibodies are obtained according to the protocol described in Example 9 of the international patent application PCT/EP2018/058168, incorporated herein by reference (in particular paragraph 158), if necessary adapted to the reading of the present invention and the general knowledge of the person skilled in the art.

Example 15: Evaluation of the Activity of the Conjugated Antibodies Obtained

A compound according to the invention (ICQN-1) was coupled to different linkers and subsequently the toxic linkers were conjugated to the antibody Trastuzumab with a view to obtaining different ADCs. Among the ADCs prepared, the following ADC Trastuzumab-Mal-PEG4-Val-Cit-PABC-ICQN-1 with DAR 4 showed in vitro nanomolar activity on the gastric carcinoma cell line NCI-N87 (IC$_{50}$=9 nM). By way of comparison, the reference ADC with the reference payload MMAE: Trastuzumab-Mal-Val-Cit-PABC-MMAE showed almost equivalent cytotoxic activity (IC$_{50}$ of 6 nM).

The invention claimed is:

1. A compound having the formula (I):

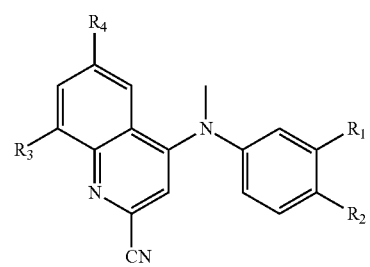

(I)

wherein:
R$_1$ represents a group: —NH$_2$, —NHCOR$_a$, —NHCO-OR$_b$, —(C$_2$-C$_6$)alkenylene-CO—NH—OH, —(C$_2$-C$_6$)alkynylene-CO—NH—OH or —OH;
R$_2$ represents a group: —OCH$_3$, —OCH$_2$CH$_3$, —SCH$_3$, —SCH$_2$CH$_3$ or —OCHF$_2$;
R$_3$ represents a hydrogen atom or a group: —CH$_3$, —CN, —F, —Cl or —OR$_c$;
R$_4$ represents a hydrogen atom or a group: —CH$_3$, —CN, —F, —Cl or —OR$_d$;
R$_a$ represents a group: —(C$_1$-C$_5$)alkyl or —CF$_3$;
R$_b$ represents a group: —(C$_1$-C$_5$)alkyl or —CF$_3$;
R$_c$ represents a group: —(C$_1$-C$_5$)alkyl or —CF$_3$; and
R$_d$ represents a group: —(C$_1$-C$_5$)alkyl or —CF$_3$;
in the following state: base or acid, or salts of acids or salts of bases; or in the form of a hydrate or a solvate.

2. The compound according to claim 1, wherein R$_3$ represents a hydrogen atom.

3. The compound according to claim 1, wherein R$_4$ represents a hydrogen atom.

4. The compound according to claim 1, having the formula (Ia):

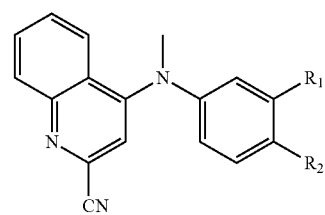

(Ia)

wherein:
R$_1$ represents a group: —NH$_2$, —NHCOR$_a$, —NHCOOR$_b$, —(C$_2$-C$_6$)alkenylene-CO—NH—OH, —(C$_2$-C$_6$)alkynylene-CO—NH—OH or —OH;
R$_2$ represents a group: —OCH$_3$, —OCH$_2$CH$_3$, —SCH$_3$, —SCH$_2$CH$_3$ or —OCHF$_2$;
R$_a$ represents a group: —(C$_1$-C$_5$)alkyl or —CF$_3$; and
R$_b$ represents a group: —(C$_1$-C$_5$)alkyl or —CF$_3$;
in the following state: base or acid, or salts of acids or salts of bases; or in the form of a hydrate or a solvate.

5. The compound according to claim 1, wherein R$_2$ represents a group: —OCH$_3$, —OCH$_2$CH$_3$, or —OCHF$_2$.

6. The compound according to claim 1, wherein R$_1$ represents a group: —NH$_2$, —NHCOR$_a$, —NHCOOR$_b$, or —OH.

7. The compound according to claim 1, selected from:

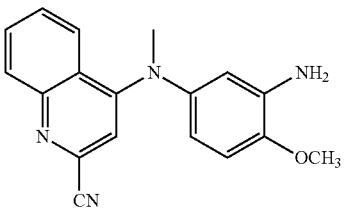

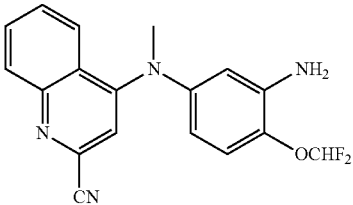

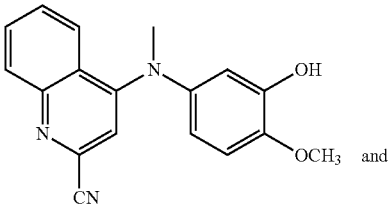

and

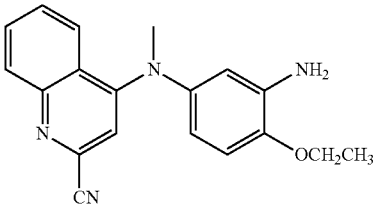

8. The compound according to claim 1, having the formula (Ib):

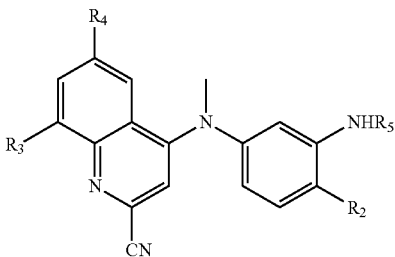

(Ib)

wherein:
R$_5$ represents a hydrogen atom, a group: —COR$_a$, or —COOR$_b$;
R$_2$ represents a group: —OCH$_3$, —OCH$_2$CH$_3$, —SCH$_3$, —SCH$_2$CH$_3$ or —OCHF$_2$;
R$_3$ represents a hydrogen atom or a group: —CH$_3$, —CN, —F, —Cl or —OR$_c$;
R$_4$ represents a hydrogen atom or a group: —CH$_3$, —CN, —F, —Cl or —OR$_d$;
R$_a$ represents a group: —(C$_1$-C$_5$)alkyl or —CF$_3$;
R$_b$ represents a group: —(C$_1$-C$_5$)alkyl or —CF$_3$;
R$_c$ represents a group: —(C$_1$-C$_5$)alkyl or —CF$_3$; and
R$_d$ represents a group: —(C$_1$-C$_5$)alkyl or —CF$_3$;
in the following state: base or acid, or salts of acids or salts of bases; or in the form of a hydrate or a solvate.

9. The compound according to claim 1, wherein R$_1$ represents a group: —(C$_2$-C$_6$)alkenylene-CO—NH—OH or —(C$_2$-C$_6$)alkynylene-CO—NH—OH.

10. The compound according to claim 1, having the formula (Ic):

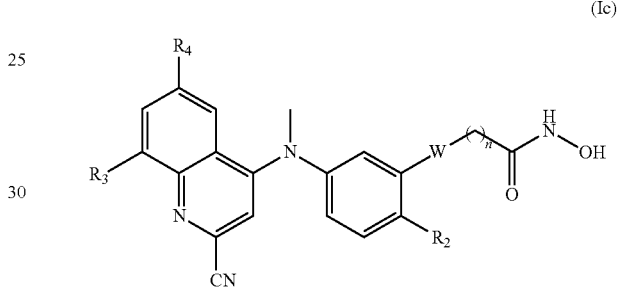

(Ic)

wherein:
W represents —CH═CH— or —C≡C—;
n is 0, 1, 2, 3 or 4;
R$_2$ represents a group: —OCH$_3$, —OCH$_2$CH$_3$, —SCH$_3$, —SCH$_2$CH$_3$ or —OCHF$_2$;
R$_3$ represents a hydrogen atom or a group: —CH$_3$, —CN, —F, —Cl or —OR$_c$;
R$_4$ represents a hydrogen atom or a group: —CH$_3$, —CN, —F, —Cl or —OR$_d$;
R$_c$ represents a group: —(C$_1$-C$_5$)alkyl or —CF$_3$; and
R$_d$ represents a group: —(C$_1$-C$_5$)alkyl or —CF$_3$;
in the following state: base or acid, or salts of acids or salts of bases; or in the form of a hydrate or a solvate.

11. The compound according to claim 10, selected from:

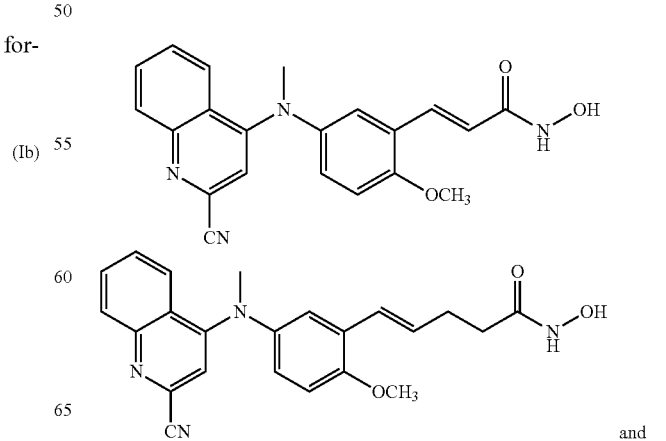

and

-continued

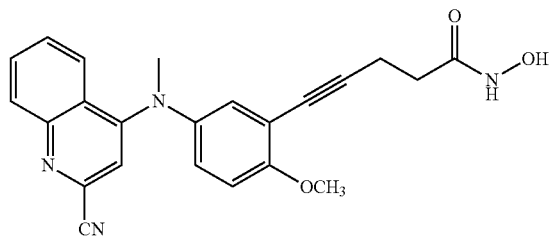

12. A preparation method for preparing a compound according to claim 1, wherein $R_1$ represents an —$NH_2$ or —OH group, wherein:

a compound having the formula (B):

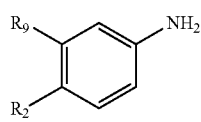
(B)

wherein $R_2$ is as defined according to claim 1 and $R_9$ represents a —$NO_2$ or —O-Benzoyl group; is brought into contact with a compound having the formula (D):

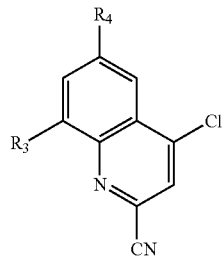
(D)

wherein $R_3$ and $R_4$ are as defined according to claim 1; so as to form, by an aromatic nucleophilic substitution reaction, or by a coupling reaction in the presence of a catalyst, the compound having the formula (E):

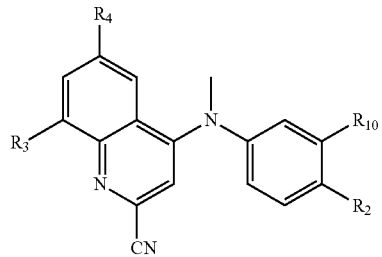
(E)

wherein $R_3$, $R_4$ and $R_2$ are as defined according to claim 1, and $R_{10}$ represents a —$NO_2$ or —O-Benzoyl group;

the compound having the formula (E) is subjected to a methylation reaction, then to a reduction or deprotection reaction so as to form the compound having the formula (I):

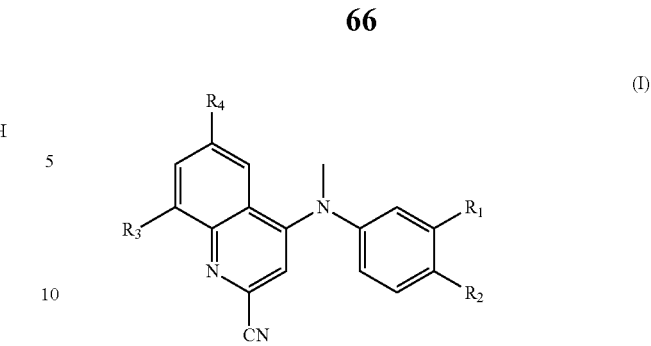
(I)

wherein $R_3$, $R_4$ and $R_2$ are as defined according to claim 1, and $R_1$ represents an —$NH_2$ or —OH group, with $R_a$ and $R_b$ being as defined according to claim 1.

13. A preparation method for preparing the compound (Ic) according to claim 10, wherein:

the compound having the formula (N):

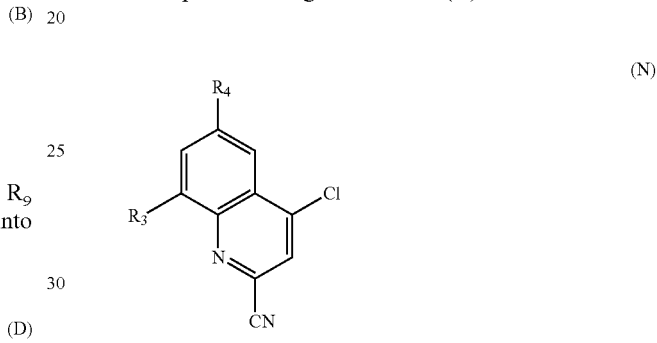
(N)

wherein $R_3$ and $R_4$ are as defined according to claim 10; is brought into contact with a compound having the formula (O):

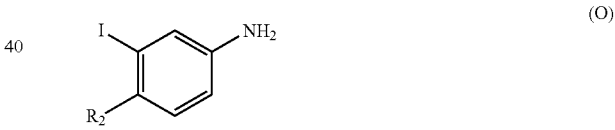
(O)

wherein $R_2$ is as defined according to claim 10, so as to form, by an aromatic nucleophilic substitution reaction, followed by a methylation reaction, the compound having the formula (P):

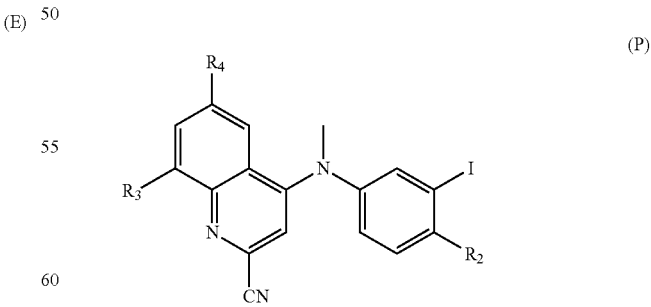
(P)

wherein $R_3$, $R_4$ and $R_2$ are as defined according to claim 10; the compound having the formula (P) is subjected to an organometallic coupling reaction with a group: —($C_2$-$C_6$)alkenylene-CO—NH—O-(2-tetrahydropyranyl) or —$C_2$-$C_6$-alkynylene-CO—NH—O-(2-tetrahydropyranyl), then to a deprotection reaction, so as to form the compound having the formula (Ic):

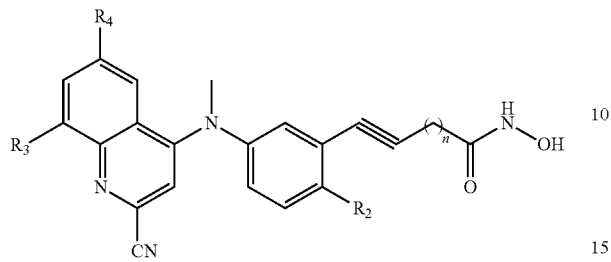
(Ic)

wherein,

, n·$R_3$, $R_4$, and $R_2$ are as defined according to claim 10.

14. An intermediate compound, selected from:

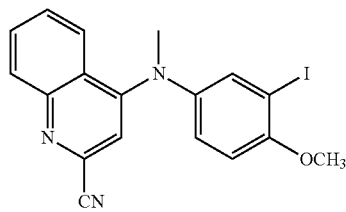

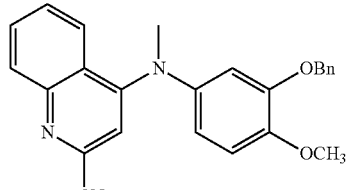

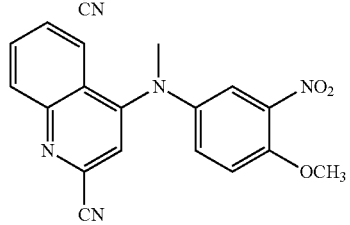
and

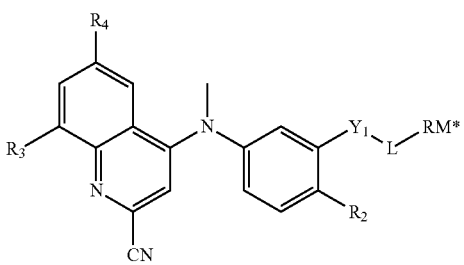

15. A compound having the formula (II):

(II)

wherein:
- $Y_1$ represents —O—, —NH—, —NHCO—, —NHCOR$_a$—, —NHCOO—, —NHCOOR$_b$—, —($C_2$-$C_6$)alkenylene-CO—NH—O— or —($C_2$-$C_6$)alkenylene-CO—NH—O—;
- $R_2$ represents a group: —OCH$_3$, —OCH$_2$CH$_3$, —SCH$_3$, —SCH$_2$CH$_3$ or —OCHF$_2$;
- $R_3$ represents a hydrogen atom or a group: —CH$_3$, —CN, —F, —Cl or —OR$_c$;
- $R_4$ represents a hydrogen atom or a group: —CH$_3$, —CN, —F, —Cl or —OR$_d$;
- $R_a$ represents a group: —($C_1$-$C_5$)alkylene- or —CF$_2$—;
- $R_b$ represents a group: —($C_1$-$C_5$)alkylene- or —CF$_2$—;
- $R_c$ represents a group: —($C_1$-$C_5$)alkyl or —CF$_3$;
- $R_d$ represents a group: —($C_1$-$C_5$)alkyl or —CF$_3$;
- L represents a linking agent (linker);
- RM* is selected from RM and RM', wherein RM is a reactive functional group that is able to form a covalent bond with a targeting agent moiety, and wherein RM' is an RM moiety carrying at least one protecting group;

in the following state: base or salts of bases; or in the form of a hydrate or a solvate.

16. The compound according to claim 15, wherein the L-RM* group is selected from among:

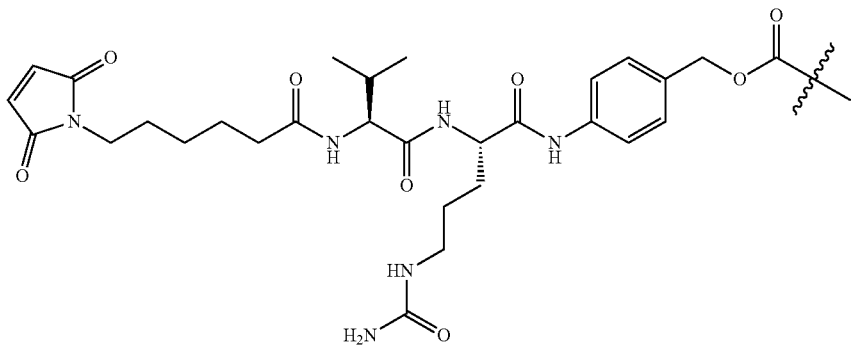

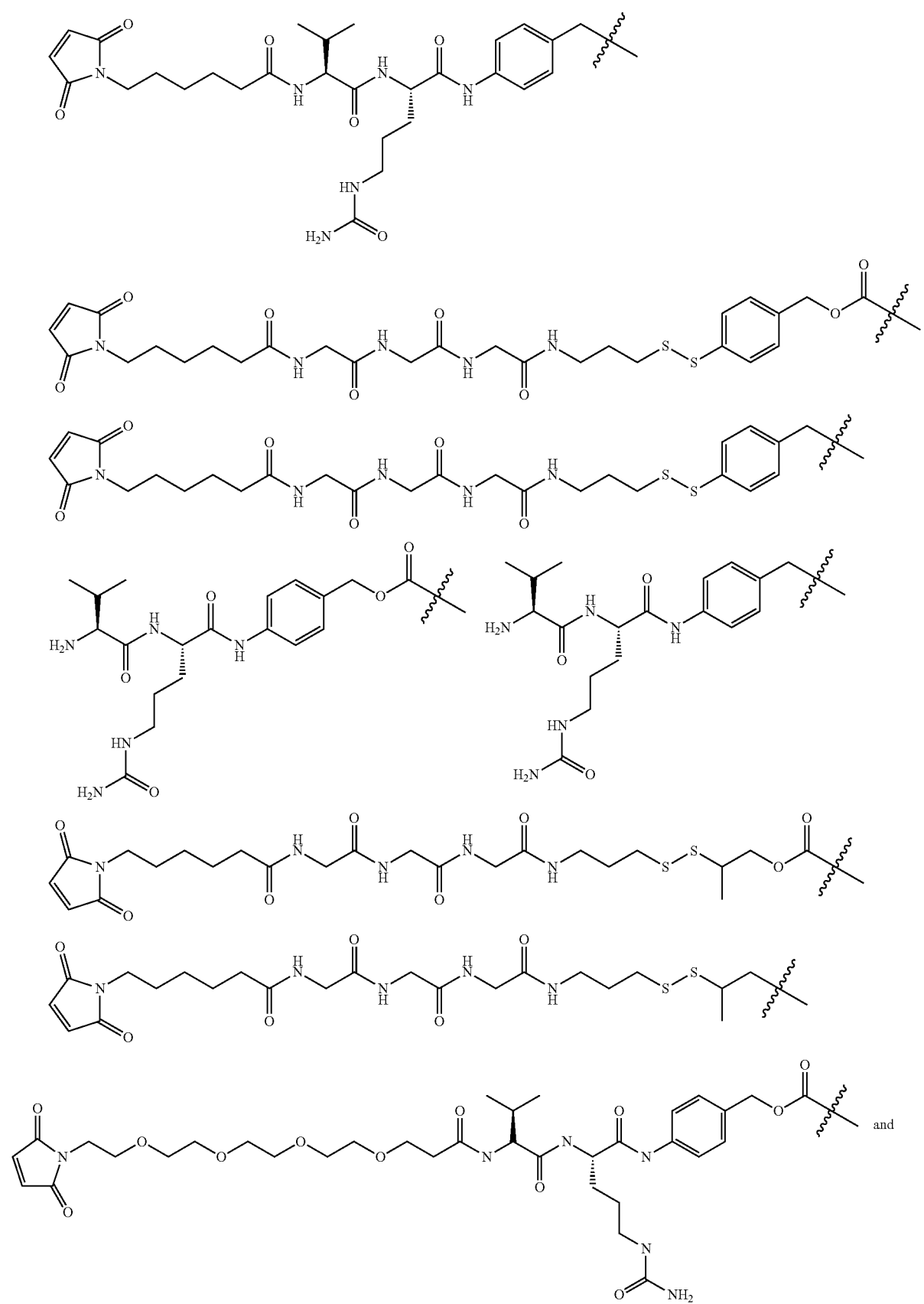

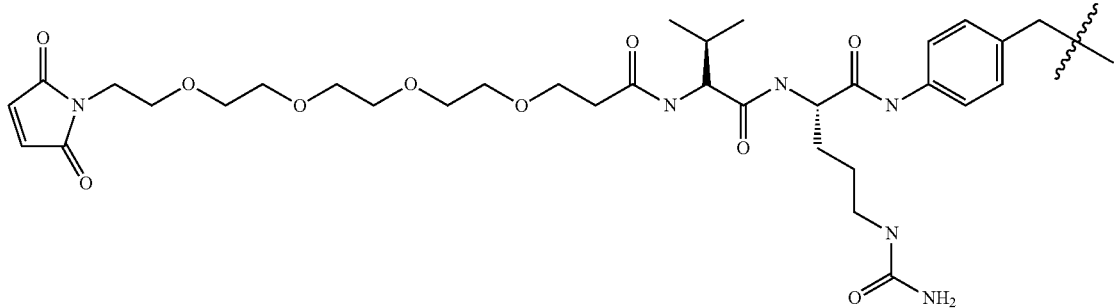
17. The compound according to claim 15, selected from among:
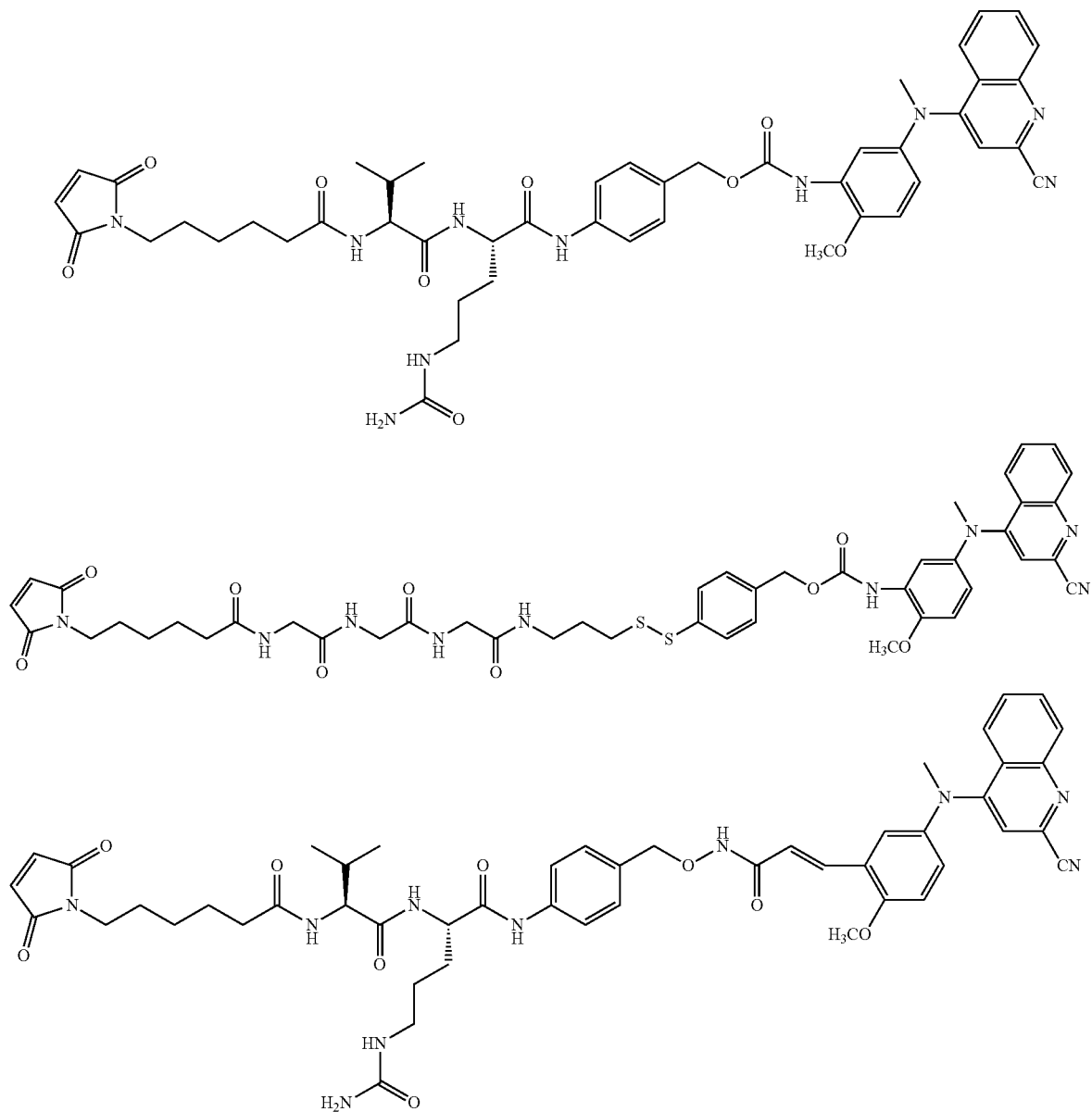

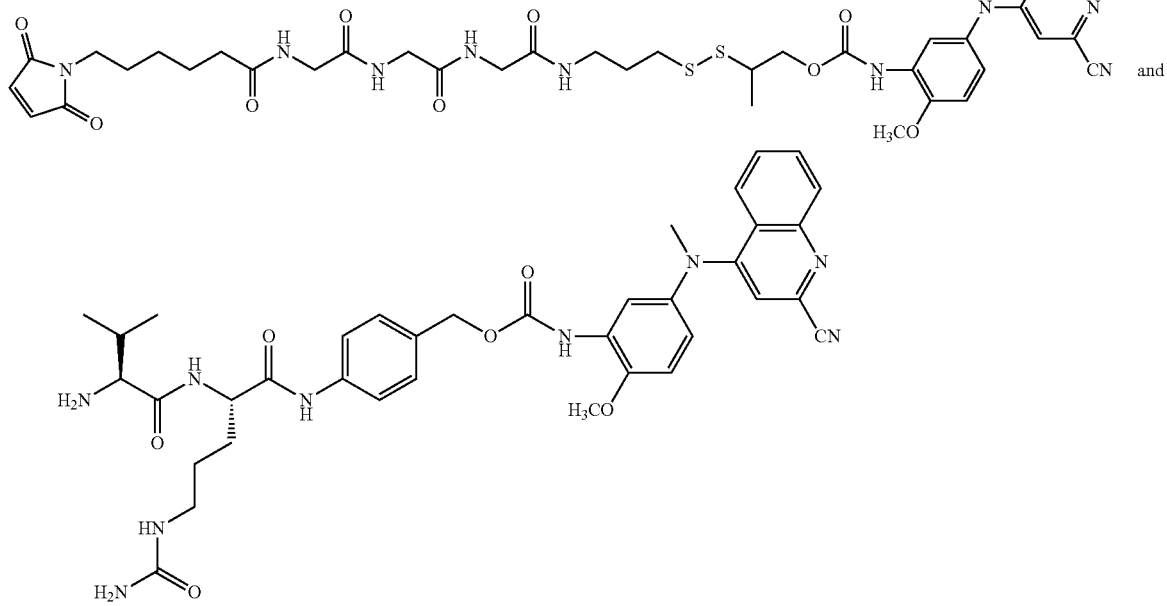

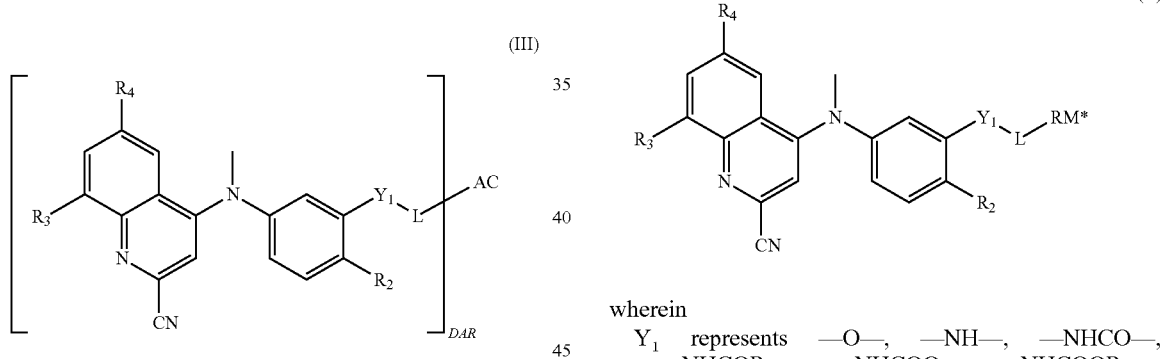

18. An antibody-drug conjugate having the formula (III):

$$\left[ \begin{array}{c} \text{structure with } R_4, R_3, \text{N-CH}_3, Y_1, L, R_2, \text{CN} \end{array} \right]_{DAR} AC \quad (III)$$

wherein:
- $Y_1$ represents —O—, —NH—, —NHCO—, —NHCOR$_a$—, —NHCOO—, —NHCOOR$_b$—, —(C$_2$-C$_6$)alkylene-CO—NH—O— or —(C$_2$-C$_6$)alkylene-CO—NH—O—;
- $R_2$ represents a group: —OCH$_3$, —OCH$_2$CH$_3$, —SCH$_3$, —SCH$_2$CH$_3$ or —OCHF$_2$;
- $R_3$ represents a hydrogen atom or a group: —CH$_3$, —CN, —F, —Cl or —OR$_c$;
- $R_4$ represents a hydrogen atom or a group: —CH$_3$, —CN, —F, —Cl or —OR$_d$;
- $R_a$ represents a group: —(C$_1$-C$_5$)alkylene- or —CF$_2$—;
- $R_b$ represents a group: —(C$_1$-C$_5$)alkylene- or —CF$_2$—;
- $R_c$ represents a group: —(C$_1$-C$_5$)alkyl or —CF$_3$;
- $R_d$ represents a group: —(C$_1$-C$_5$)alkyl or —CF$_3$;
- L represents a linking agent (linker);
- AC represents a targeting agent moiety; and
- wherein the DAR (drug-to-antibody [targeting agent] ratio) varies between 1 and 8.

19. A preparation method for preparing a compound having the formula (II)

$$\text{(II)}$$

wherein
- $Y_1$ represents —O—, —NH—, —NHCO—, —NHCOR$_a$—, —NHCOO—, —NHCOOR$_b$—, —(C$_2$-C$_6$)alkylene-CO—NH—O— or —(C$_2$-C$_6$)alkylene-CO—NH—O—;
- $R_2$ represents a group: —OCH$_3$, —OCH$_2$CH$_3$, —SCH$_3$, —SCH$_2$CH$_3$ or —OCHF$_2$;
- $R_3$ represents a hydrogen atom or a group: —CH$_3$, —CN, —F, —Cl or —OR$_c$;
- $R_4$ represents a hydrogen atom or a group: —CH$_3$, —CN, —F, —Cl or —OR$_d$;
- $R_a$ represents a group: —(C$_1$-C$_5$)alkylene- or —CF$_2$—;
- $R_b$ represents a group: —(C$_1$-C$_5$)alkylene- or —CF$_2$—;
- $R_c$ represents a group: —(C$_1$-C$_5$)alkyl or —CF$_3$;
- $R_d$ represents a group: —(C$_1$-C$_5$)alkyl or —CF$_3$;
- L represents a linking agent (linker);
- RM* is selected from RM and RM', wherein RM is a reactive functional group that is able to form a covalent bond with a targeting agent moiety, and wherein RM' is an RM moiety carrying at least one protecting group;
- in the following state: base or salts of bases: or in the form of a hydrate or a solvate;

the method comprising a reaction step of reacting a compound having the formula (I) according to claim 1, with a compound having the formula X-L"-RM* wherein:

X represents a group that is capable of reacting with an $R_1$ group as defined according to claim 1;

L represents a linking agent (linker);

RM* is selected from RM and RM', wherein RM is a reactive functional group that is able to form a covalent bond with a targeting agent moiety, and wherein RM' is an RM moiety carrying at least one protecting group;

wherein the reaction between the $-R_1$ moiety of the compound having the formula (I) and the compound having the formula X-L"-RM* results in the formation of a $-Y_1$-L-RM* moiety.

20. The A preparation method according to claim 19, wherein RM* is RM, the method further comprising a deprotection step of deprotecting an RM' moiety resulting in an RM group.

21. A pharmaceutical composition comprising an antibody-drug conjugate according to claim 18, in association with a pharmaceutically acceptable carrier.

22. A method of therapeutic treatment, wherein said method comprises administering to a subject in need thereof an antibody-drug conjugate according to claim 18.

23. The method according to claim 22, wherein the therapeutic treatment is killing or inhibiting cell growth.

24. The method according to claim 22, wherein the therapeutic treatment is treatment of cancer.

* * * * *